(12) United States Patent
Alexander et al.

(10) Patent No.: US 10,585,097 B2
(45) Date of Patent: Mar. 10, 2020

(54) BACTERIAL ENDOTOXIN TEST FOR THE DETERMINATION OF ENDOTOXINS

(71) Applicants: Forschungszentrum Borstel Leibniz Lungenzentrum, Borstel (DE); Hoffmann-La Roche Inc., Little Falls, NJ (US)

(72) Inventors: Christian Alexander, Borstel (DE); Sven Deutschmann, Weilheim (DE); Pierre Lang, Blotzheim (FR); Friedrich Von Wintzingerode, Penzberg (DE); Ulrich Zaehringer, Ahrensburg (DE)

(73) Assignees: Forschungszentrum Borstel Leibniz Lungerzentrum, Borstel (DE); Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 15/739,503

(22) PCT Filed: Jul. 27, 2016

(86) PCT No.: PCT/EP2016/067896
§ 371 (c)(1),
(2) Date: Dec. 22, 2017

(87) PCT Pub. No.: WO2017/017135
PCT Pub. Date: Feb. 2, 2017

(65) Prior Publication Data
US 2018/0188249 A1  Jul. 5, 2018

(30) Foreign Application Priority Data
Jul. 28, 2015 (EP) .................................... 15178683

(51) Int. Cl.
*G01N 33/579* (2006.01)
*G01N 33/569* (2006.01)
*G01N 1/38* (2006.01)

(52) U.S. Cl.
CPC ......... *G01N 33/56911* (2013.01); *G01N 1/38* (2013.01); *G01N 33/579* (2013.01)

(58) Field of Classification Search
None
See application file for complete search history.

(56) References Cited

U.S. PATENT DOCUMENTS

| 2,123,198 | A | * | 7/1938 | Parfentjev | .............. | C07K 16/06 424/130.1 |
| 4,096,091 | A | | 6/1978 | Hopkins, II | | |
| 4,124,509 | A | * | 11/1978 | Iijima | ..................... | B01D 61/28 210/321.79 |
| 4,680,177 | A | * | 7/1987 | Gray | ..................... | A61K 35/28 424/529 |

FOREIGN PATENT DOCUMENTS

| CN | 102841205 A | 12/2012 |
| CN | 102901726 A | 1/2013 |
| EP | 0513361 A1 | 11/1922 |

OTHER PUBLICATIONS

Sofer, Gail.Biotechnology 2, 1035-1038 (1984).*
Blood Function and Composition. https://www.myvmc.com/anatomy/blood-function-and-composition (Jan. 1, 2008) retrieved Dec. 10, 2018.*
Thermo Fisher Scientific Pierce High-Performance Dialysis, Desalting and Detergent Removal Technical Handbook Featuring Thermo Scientific Slide-A-Lyzer Dialysis Cassettes. Version 2. Thermo Scientific. pp. 1-29, 2009.*
Piotrowicz, B. The Chromogenic Limulus Amoebocyte Lysate LAL assay for endotoxin: Developments and Applications. Dissertation Thesis. University of Glasgow, 1986.*
The extended European Search Report, dated Jan. 14, 2016, in the related European Application No. 15178683.7.
The International Search Report and Written Opinion, dated Oct. 10, 2016, in the related PCT Application No. PCT/EP2016/067896.
Sourek et al: "Effects of certain cations(Fe, Zn, Mg, and Ca) on bacterial endotoxins", Infection and Immunity, vol. 21, No. 2, Aug. 1, 1978, pp. 648-654, XP55239041.
Sun et al: "Monoclonal anti-double-stranded DNA autoantibody stimulates the expression and release of IL-Ib, IL-6, IL-8, IL-10 and TNF-a from normal human mononuclear cells involving in the lupus pathogenesis", Immunology, vol. 99, No. 3, Mar. 1, 2000, pp. 352-360, XP55239052.
Tsuji K et al: "Use of magnesium to increase sensitivity of Limulus amoebocyte lysate for detection of endotoxin", Applied and Environmental Microbiology, American Society for Microbiology, vol. 45, No. 4, Apr. 1, 1983, pp. 1342-1350, XP008142470.
Williams: "Endotoxin Test Concerns of Biologics", American Pharmaceutical Review, vol. 16, No. 6, Oct. 28, 2013, XP56238826.
Petsch et al., "Proteinase K Digestion of Proteins Improves Detection of Bacterial Endotoxins by the Limulus Amebocyte Lysate Assay: Application for Endotoxin Removal from Cationic Proteins," 1998 Anal. Biochem. 259:42-47.
Chen and Vinther, "Low Endotoxin Recovery (LER) in Common Biologics Products," 2013 PDA Annual Meeting, Orlando Florida, Apr. 17, 2013.
Hughes et al., "Low Endotoxin Recovery: An FDA Perspective," 2015, BioPHarma Asia Mar./Apr. 14-25.
The Chinese Office Action, dated Oct. 16, 2019, in the related Chinese Patent Appl. No. 201680044156.7.
Yang et al., "Assay of Bacterial Endotoxin in dialysis solution for artificial kidney", Chin. Hosp. Pham. J., Nov. 2002, vol. 22, No. 11. The English abstract included.
Liu et al., "Limulus Reagent and application thereof", Chin J Mod Drug Appl, May 2008, vol. 2, No. 9. The English included.
Pei et al., "Progress on new methods of bacterial endotoxin test," Chin J. Pharm Anal, 2014, 34(3). The English included.

* cited by examiner

*Primary Examiner* — Oluwatosin A Ogunbiyi

(57) ABSTRACT

Herein is reported a method for determining bacterial endotoxin at low concentrations in a sample of an antibody (that has been produced using bacterial cells) comprising the following steps in the following order: i) adding magnesium ions to the sample, ii) diluting the sample, iii) dialyzing the sample having a pH-value of 5.7-8.0 against an endotoxin-free aqueous solution, and iv) determining bacterial endotoxin in the sample using a bacterial endotoxin test, particularly the *limulus* amoebocyte lysate assay.

52 Claims, 29 Drawing Sheets

Specification includes a Sequence Listing.

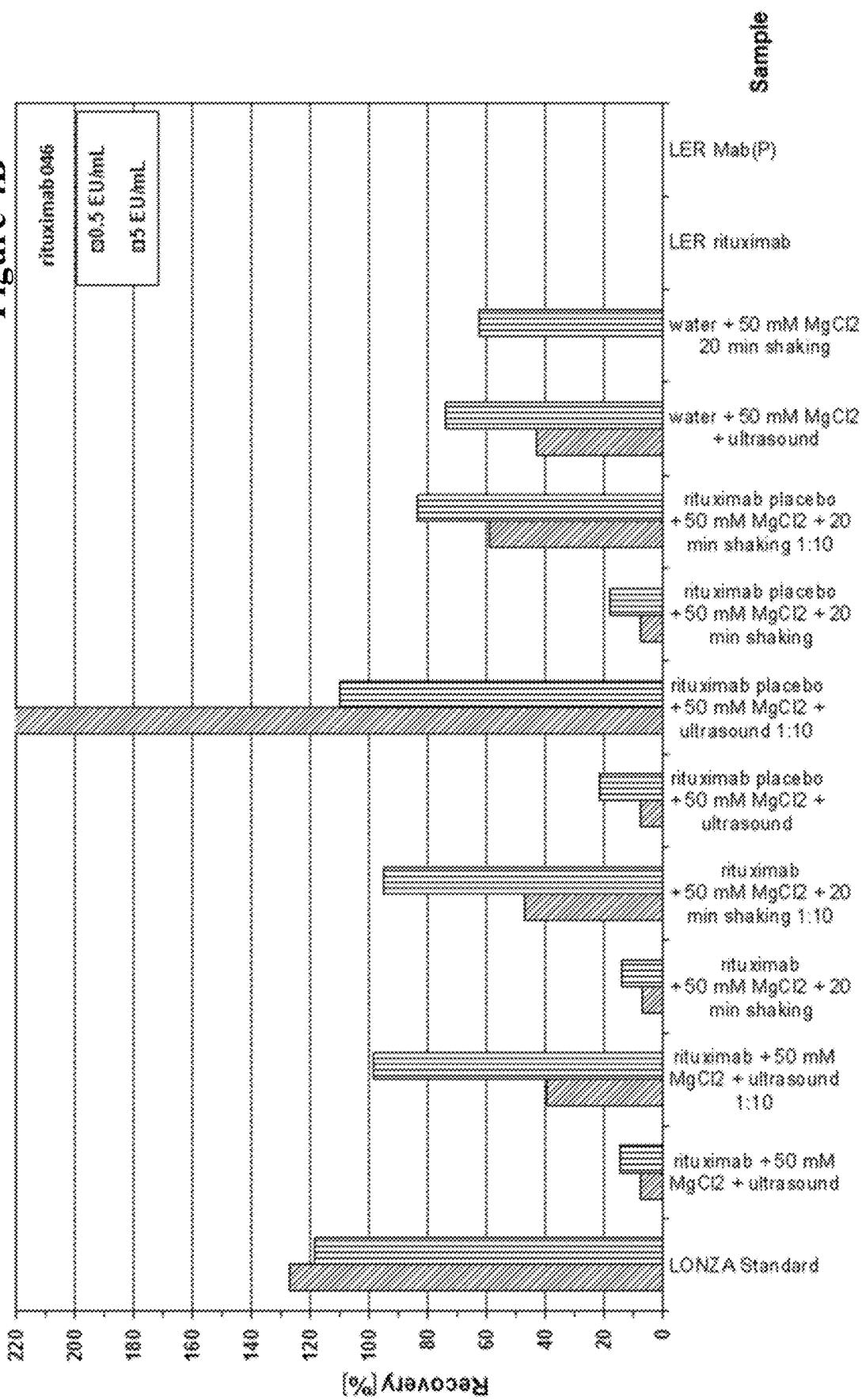

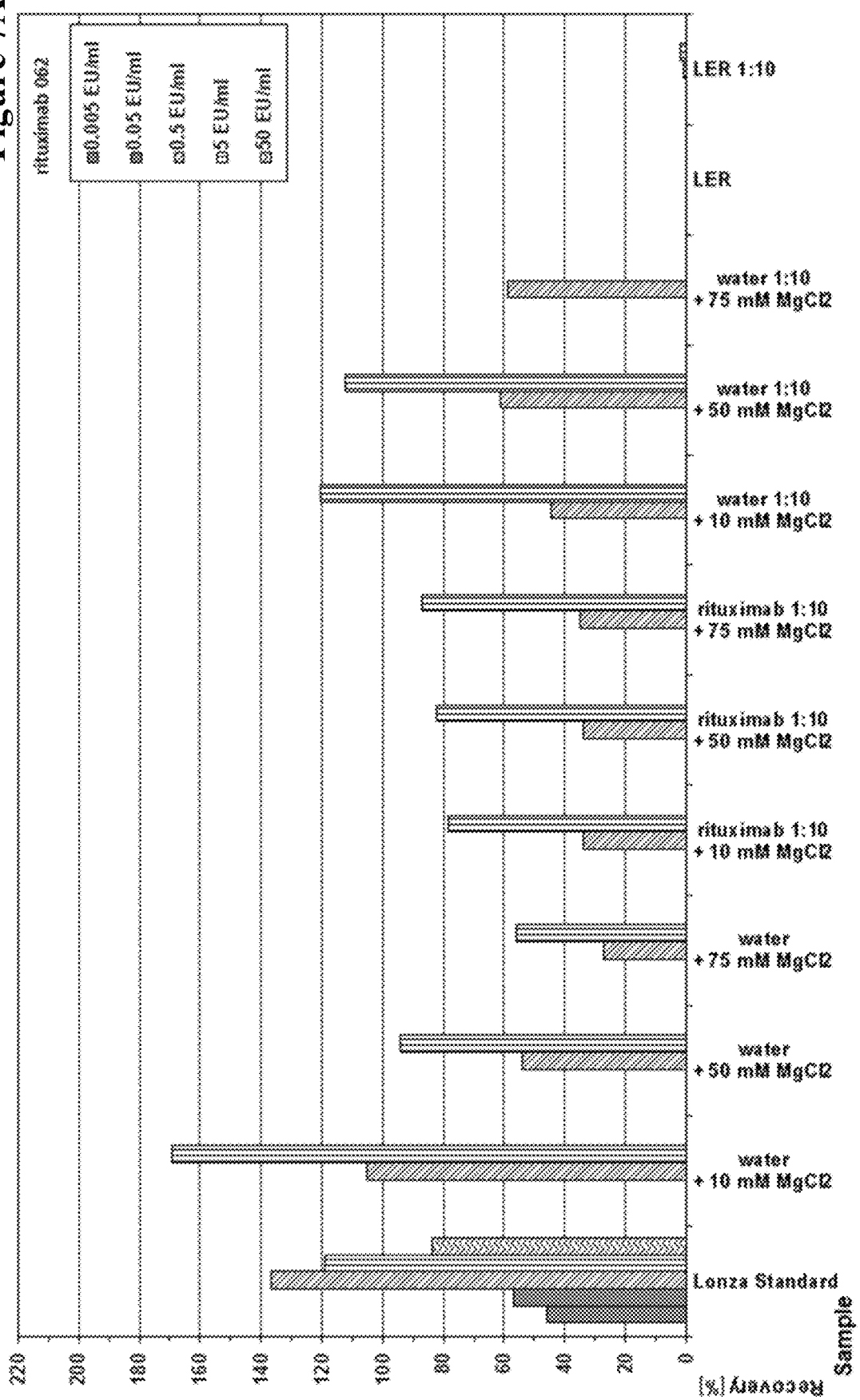

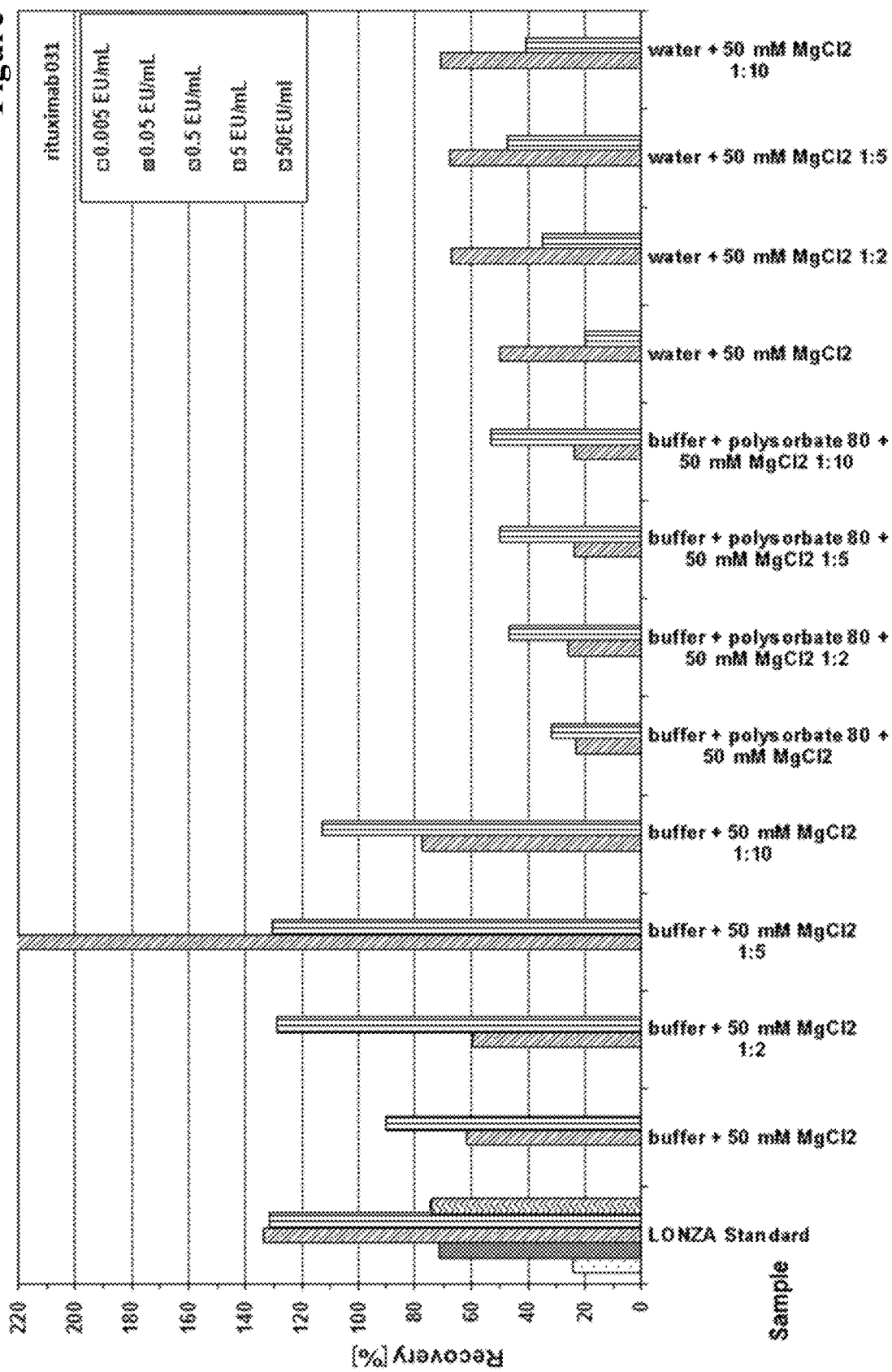

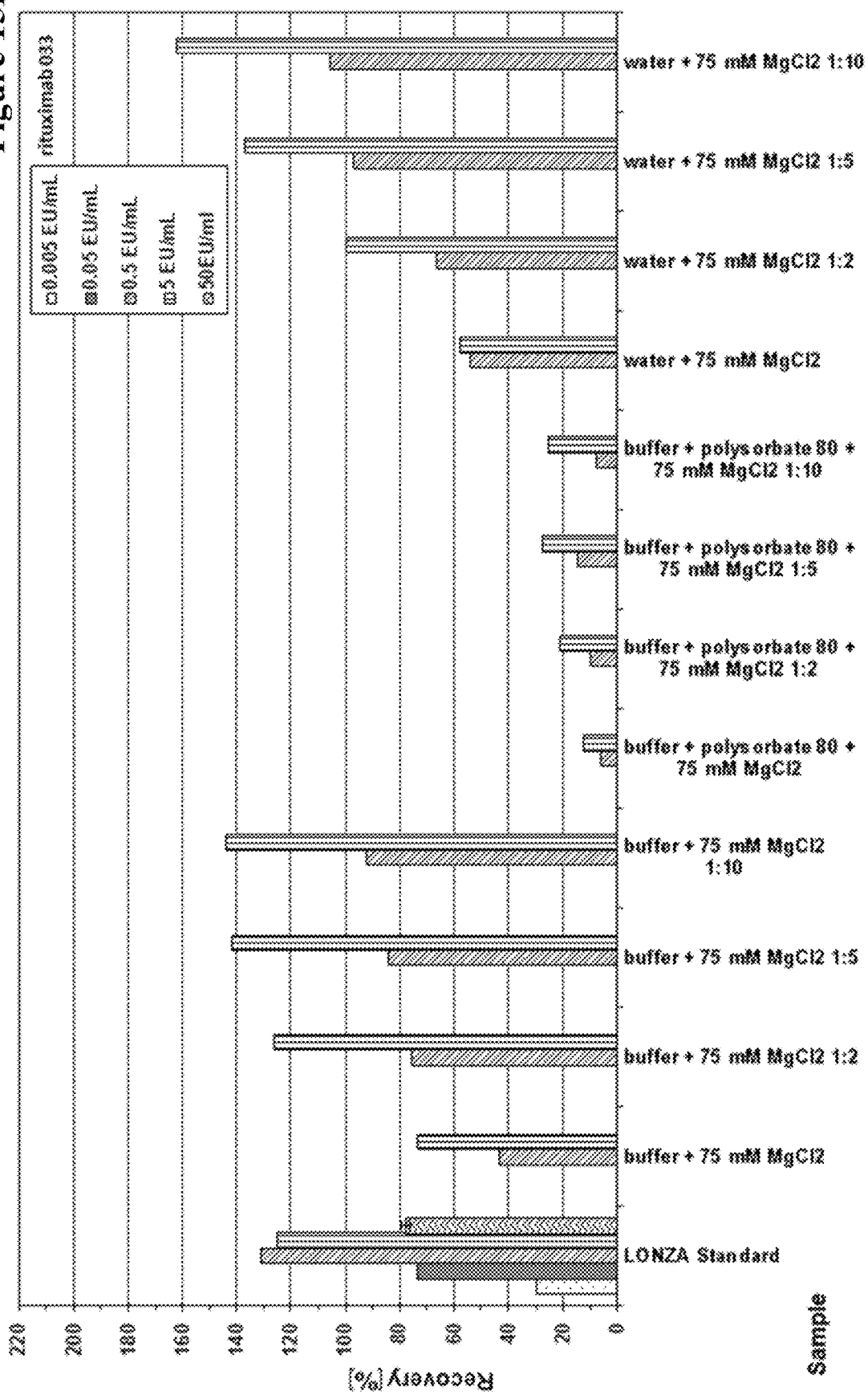

BACTERIAL ENDOTOXIN TEST FOR THE DETERMINATION OF ENDOTOXINS

This application is a National Stage Application of PCT/EP2016/067896 filed Jul. 27, 2016, which claims priority from European Patent Application No. 15178683.7, filed on Jul. 28, 2015. The priority of both said PCT and European Patent Application are claimed. Each of prior mentioned applications is hereby incorporated by reference herein in its entirety.

Herein reported is a bacterial endotoxin test (BET) sample preparation method that overcomes the low endotoxin recovery (LER) effect that is due to endotoxin masking.

Protein therapeutics (such as monoclonal antibodies) are often generated using genetically transformed eukaryotic and prokaryotic cells, such as e.g. bacteria. Used for bacterial productions are fast growing bacteria such as *Escherichia coli*. However, during growth and cultivation of the recombinant protein highly toxic lipopolysaccharides (LPS) are secreted into the medium. These components are denoted as bacterial endotoxins (short endotoxins). Gram-negative bacteria possess LPS as an essential component of their cell wall. A Gram-negative bacteria cell contains approximately $3.5 \times 10^5$ LPS molecules, which occupy an overall area of approximately 4.9 µm$^2$ (Rietschel, 1994, FASEB J. 8:217-225). In the case of *E. coli*, it means that LPS represent about three-quarters of the total bacterial cell surface. Approximately 10,000 CFU (colony forming units) of a Gram-negative bacterium species correspond to 1 Endotoxin Unit (EU) (Rietschel, 1994, FASEB J. 8:217-225). EU refers to endotoxin/LPS; 1 EU≈100 pg LPS, depending on the LPS used. However, even if products are not produced by recombinant means, most employed reagents are contaminated with endotoxin, as their production is rarely done under aseptic or even sterile conditions. Therefore, LPS are ubiquitous potential contaminants in case sterile and/or aseptic conditions, during production of pharmaceuticals, cannot be kept. Among all known bacterial compounds, endotoxin is one of the most toxic natural compounds for mammals. LPS as present in the cell wall of Gram-negative bacteria are known to cause profound immunoactivation including the induction of fever when entering the human bloodstream. It causes delirious effects at extreme low concentrations (picogram-range) when entering the cardiovascular and lymphatic system, respectively. Unfortunately bacterial endotoxins are heat stable and their toxicity is not linked to the presence of the bacterial cell at all. It is also generally known that all protein therapeutics, irrespective of the method of their production, must be expected or considered to be contaminated with low traces of bacterial endotoxins (so called "natural occurring endotoxin", NOE). Therefore, endotoxin contamination remains a continuous challenge for the production of pharmaceuticals such as therapeutic monoclonal antibodies. This has been outlined with emphasis very clearly in the "*Guidance for Industry, pyrogen and endotoxin testing*", issued by the Food and Drug Administration (FDA) in June 2012.

To ensure that injectable protein therapeutics (such as monoclonal antibodies) are safe for human use, endotoxin testing has to be done. Endotoxin testing is commonly performed using the compendial methods of US Pharmacopeia <85>, European Pharmacopeia 2.6.14 or Japanese Pharmacopeia 4.01 with gel-clot, chromogenic or turbidimetric *Limulus* amoebocyte lysate (LAL) techniques (also designated as LAL assay or LAL test). The compendial name for the LAL assay is bacterial endotoxin(s) test (BET). The BET is used for detecting the presence of unsafe levels of endotoxin, in particular of Gram-negative bacterial endotoxin, in a given sample or substance.

The LAL assay is routinely performed with a diluted test sample along with a positive control, which is a sample with a known amount of spiked control standard endotoxin (CSE). CSE is a defined form of endotoxin commercially available (supplied, e.g., by Lonza, Associates of Cape Cod, Inc. (ACC), or Charles River Laboratories International, Inc.). According to the compendial LAL assay method qualification, CSE is spiked to a diluted sample at a non-interfering concentration (NIC) to achieve an acceptable recovery rate of 50-200%. This approach fails to recognize that components of the sample matrix of pharmaceutical formulations as well as storage conditions potentially impact the LAL reactivity of endotoxins present in undiluted product samples. When undiluted product samples are spiked with endotoxins such as CSE followed by LAL assay, low endotoxin recovery (<50%) was observed for certain biologic products. Such low endotoxin recovery was particularly observed if the formulation of the product contained amphiphilic compounds such as detergents. Detergents are added to the product in order to solubilize the therapeutic protein. This masking of endotoxin results in the significantly reduced detection of endotoxin, especially in case the LPS contamination is low. This phenomenon is called "endotoxin masking" if endotoxin recovery cannot be increased by sample dilution after spiking.

Different sample pre-treatments for the LAL assay to overcome assay inhibition and/or enhancement are known. However, at present these sample pre-treatments do not lead to satisfactory results. Therefore, there is still a risk that endotoxin contaminations occur during manufacturing of pharmaceuticals that cannot be detected by the LAL assay due to endotoxin masking. Based on current knowledge there are two different types of endotoxin masking:

1) Endotoxin masking caused by endotoxin-binding proteins present in the sample ("protein masking", Petsch, Anal. Biochem. 259, 1998, 42-47). For example the formation of protein-endotoxin aggregates, e.g. with human lipoproteins Apo A1, lysozyme, ribonuclease A or human IgG, is well known to reduce LAL reactivity of endotoxins (Emancipator, 1992; Petsch, Anal. Biochem. 259, 1998, 42-47).
2) Endotoxin masking caused by certain formulation ingredients or buffer components often present in pharmaceutical products. For example, endotoxin masking specifically caused by a combination of polysorbate plus either citrate or phosphate is termed "Low Endotoxin Recovery" or LER (Chen, J. and Williams, K. L., PDA Letter 10, 2013, 14-16, Williams, American Pharmaceutical Review, Oct. 28, 2013: Endotoxin Test Concerns of Biologics). Endotoxin masking may also be caused by any other buffer component and non-ionic detergent or combinations thereof.

Due to the LER effect, potential endotoxin contaminations occurring during manufacturing remain underestimated or undetected when a conventional LAL assay is used. The LER effect represents a continuous challenge for pharmaceutical products (Hughes, BioPharm. Asia Mar./Apr. 2015, 14-25).

Accordingly, the technical problem underlying the present invention is the provision of means and methods for overcoming the LER effect.

The technical problem has been overcome by the methods of the present invention as detailed below.

Herein is reported an improved LAL assay for quantification of endotoxin. This improved LAL assay is particularly useful when amphiphilic matrices mask endotoxin determination (Low-Endotoxin-Recovery; LER).

In particular, in context of the present invention it was surprisingly found that by the sequence of adding magnesium ions, e.g. in form of $MgCl_2$, to a sample; diluting the sample; and dialyzing the sample having a pH-value of 5.7-8.0, the LER effect can successfully be overcome. Or, in other words, the sample preparation method as reported herein is suitable for overcoming the LER effect in a LAL assay.

More specifically, in context of the present invention, a sample preparation method for samples comprising an antibody (e.g. a sample of a therapeutic monoclonal antibody) has been found. This inventive sample preparation method has the advantage that it surprisingly and unexpectedly obviates the LER effect if a LAL assay is performed. More specifically, the present invention relates to a method for the preparation of a sample comprising an antibody for BET (preferably for a LAL assay), wherein the method comprises the following steps in the following order:
  (a) adding magnesium ions, preferably in form of $MgCl_2$, to the sample,
  (b) diluting the sample, and
  (c) dialyzing the sample having a pH-value of 5.7-9.0, preferably of 5.7-8.0, against an endotoxin-free aqueous solution.

Thus, according to the present invention, a sample comprising an antibody (e.g. a sample of a therapeutic monoclonal antibody) is processed by performing the steps (a) to (c) of the inventive sample preparation method. These steps and their combination surprisingly lead to the provision of a sample, which does not suffer from the LER effect if a LAL assay is performed. Or, in other words, after performing the steps (a) to (c) of the herein provided sample preparation method, the sample comprising an antibody is reactive to factor C in the LAL enzymatic cascade. Thus, the inventive sample preparation method is advantageously performed before determining bacterial endotoxin via the LAL assay. Accordingly, the present invention also relates to a method for determining (i.e. detecting and/or quantifying) endotoxin in a sample. In particular, the herein provided endotoxin determination method allows the determination (i.e. the detection and/or quantification) of endotoxin in a sample comprising an antibody (e.g. a therapeutic monoclonal antibody). In particular, the present invention relates to a method for determining bacterial endotoxin in a sample (that preferably exhibits a LER effect) comprising an antibody, wherein the method comprises the following steps in the following order:
  (a) adding magnesium ions, preferably in form of $MgCl_2$, to the sample (i.e. to the sample comprising an antibody),
  (b) diluting the sample,
  (c) dialyzing the sample having a pH-value of 5.7-8.0 against an endotoxin-free aqueous solution, and
  (d) determining bacterial endotoxin in the sample by using a LAL assay.

Preferably, in the sample preparation method or the endotoxin determination method of the present invention, 1.5-5 ml clear glass, crimp neck, flat bottom vessels are used. Most preferably, the vessels are screw neck glass vials of Macherey-Nagel GmbH (1.5 ml or 4 ml).

Endotoxin contamination represents a high risk in the production of pharmaceuticals such as monoclonal antibodies. In the prior art endotoxin testing, in particular for therapeutic antibodies, is performed by using a conventional LAL assay. However, as demonstrated in the appended Examples, the LAL assay fails to detect/underestimates endotoxin contamination in antibody formulations that exhibit the LER effect. Undetected/underestimated endotoxin represents an extreme safety risk for any pharmaceutical sample, particularly for pharmaceuticals that are administered intramuscularly or intravenously. However, despite of its tremendous practical importance, nothing is known about the physico-chemical mechanisms of the LER effect. Hence, the prior art fails to provide methods for the correct determination of endotoxin in therapeutic products that exhibit the LER effect.

In context of the present invention a robust physico-chemical set-up, which obviates the LER effect and results in satisfactory recovery rates from CSE-spiked samples has been found. In particular, as demonstrated in the illustrative appended Examples, the methods as reported herein allow the recovery of the CSE spiked to a given sample at a defined concentration (0.5 or 5.0 EU/ml). Importantly, the herein provided methods lead to recovery rates ranging between 50% and 200%, this way fulfilling the requirements of the FDA. Thus, the present invention advantageously provides methods, which are able to unmask endotoxins and to overcome the LER effect. More specifically, in context of the present invention it has surprisingly been found that the specific combination and sequence of the steps (a) to (c) (i.e. (a) adding magnesium ions to the sample to be tested; (b) diluting the sample to be tested; and (c) dialyzing the sample to be tested (wherein the sample has a pH-value of 5.7-8.0), obviates the LER effect of the sample to be tested for endotoxin. Or, in other words, performing the steps (a) to (c) unmasks the endotoxin in the sample, and thus, makes the endotoxin detectable with the LAL assay. The appended Examples show that the herein provided methods overcome the LER effect e.g. in formulated rituximab. By contrast, the same protocol could not reveal satisfactory results for Neo-Recormon® (which does not comprise an antibody but epoetin-beta). This indicates that the herein provided methods are particularly useful for obviating the LER effect in antibody formulations, preferably in formulations with a monoclonal antibody, citrate buffer and polysorbate 80.

Thus, the herein provided sample preparation method and the herein provided endotoxin determination method advantageously obviate the LER effect. Therefore these methods improve the detection of endotoxin in pharmaceuticals. This leads to the production of pharmaceutical products with less adverse effects. Consequently, the herein provided methods will improve the state of health of the consumer and may save the lives of critically ill patients.

In the herein provided methods, the antibody that is comprised in the sample may have been produced in and/or purified from bacterial or eukaryotic cells. For example, the antibody may have been produced and purified from Chinese hamster ovary (CHO) cells. In one aspect of the invention, the sample (i.e. the sample comprising an antibody) is a dissolved solid sample. In another aspect of the invention, the sample (i.e. the sample comprising an antibody) is a liquid sample. In the herein provided sample preparation method and endotoxin determination method, it is envisaged that the antibody (i.e. the antibody that is comprised in the sample) is a therapeutic antibody. Preferably, the antibody (i.e. the antibody that is comprised in the sample) is a monoclonal antibody. However, in the herein provided methods the antibody (that is comprised in the sample) may also be a polyclonal antibody. Herein, also multispecific antibodies (e.g., bispecific antibodies), or antibody fragments are comprised by the term "antibody", so long as they exhibit the desired biological activity. The antibody may be human, humanized, or camelized.

The herein provided methods advantageously render LER-prone samples of a pharmaceutical formulation reactive to factor C in the LAL enzymatic cascade. The LER effect has been reported in biologic products, which are formulated with amphiphilic compounds such as non-ionic detergents, in particular if they are combined with citrate or phosphate as buffer. The appended Examples demonstrate that the herein provided methods reliably obviate the LER effect in such therapeutic formulations. Therefore, it is envisaged in context of the herein provided sample preparation method and endotoxin determination method that said therapeutic antibody (i.e. the therapeutic antibody that is comprised in the sample) is formulated with at least one detergent (preferably a polysorbate).

However, it is envisaged that said therapeutic antibody is formulated with a polysorbate that does not comprise a structural motif for the lipid A cavity in the C reactive protein of the LAL cascade. More specifically, straight chain fatty acids such as lauric acid may mimic the fatty acids in the lipid A molecule of the LAL cascade, as this molecule also contains fatty acids with 12 carbon atoms and no double bonds (i.e. C:D is 12:0). Such straight fatty acids may negatively interfere with the LAL cascade. Therefore, in the herein provided methods, it is envisaged that said therapeutic antibody is not formulated with a detergent that comprises straight fatty acids such as lauric acid. Polysorbate 20 comprises lauric acid. Thus, it is envisaged in the herein provided methods that the sample (in particular the sample of a therapeutic antibody) is not formulated with polysorbate 20. Also phosphate buffer, particularly sodium phosphate buffer, may interfere with the LAL cascade. Therefore, these buffers are less useful for the herein provided sample preparation methods. Accordingly, the invention relates to the herein provided sample preparation method or endotoxin determination method, wherein the (therapeutic) antibody that is comprised in the sample is not diluted with a phosphate buffer. In one aspect of the present invention the sample does not comprise more than 0.1 mM phosphate buffer and does not comprise a concentration of polysorbate 20 that is higher than $\frac{1}{100}$ of its critical micellar concentration (CMC). In a preferred aspect of the present invention, the sample does either not comprise phosphate buffer and polysorbate 20, or comprises an amount of phosphate buffer and/or polysorbate 20 that is blow the detection limit when using standard detection methods.

As demonstrated in the appended Examples by using the methods of the invention, the LER effect can be overcome in formulated rituximab samples as well as in rituximab placebo samples. Rituximab placebo samples only differ from rituximab samples in that the antibody is absent. Beside this difference, rituximab placebo samples contain all the other components of the formulation of rituximab such as detergent and buffer. This indicates that the herein provided methods do not depend on a formulation comprising a particular monoclonal antibody but can be used, e.g., to obviate the LER effect in every formulation exhibiting this effect. Such formulations include formulations comprising polysorbate 80 and a chelating buffer (such as sodium citrate). This formulation is typical for antibodies, in particular monoclonal antibodies. Thus, the above described method is expected to be useful to overcome the LER effect in every monoclonal antibody formulation. Rituximab is formulated with a mixture of polysorbate 80 and sodium citrate buffer (i.e. 25 mM sodium citrate buffer, pH 6.5; 700 mg/l polysorbate 80, and 154 mM NaCl). It is envisaged in context of the present invention, that the sample comprising an antibody has this formulation.

The appended Examples demonstrate that in exemplary samples of therapeutic antibodies that are formulated with polysorbate 80 and citrate buffer, the LER effect can be overcome by using the herein provided methods. Therefore, in the herein provided sample preparation method or endotoxin determination method it is preferred that the sample (i.e. the sample comprising an antibody) is formulated with polysorbate 80. Accordingly, in the herein provided methods, it is envisaged that the sample (i.e. the sample comprising an antibody) comprises polysorbate 80. Preferably, the sample comprises 500-1000 mg/l polysorbate 80, more preferably about 700 mg/l polysorbate 80. It is further envisaged in the herein provided methods that the sample (i.e. the sample comprising an antibody) is formulated with a chelating buffer (such as citrate buffer). Said citrate buffer may be a 5-50 mM citrate buffer, pH 6.0-7.0; preferably a 25 mM citrate buffer, pH 6.5. Preferably, the citrate buffer is a sodium citrate butter. For example, in the herein provided methods, the sample (i.e. the sample comprising an antibody) may comprise 5-50 mM Na-citrate, preferably 25 mM Na-citrate. Most preferably, the sample comprises polysorbate 80 and sodium citrate buffer. For example, the sample may comprise about 700 mg/l polysorbate 80 and 5-50 mM, preferably about 25 mM sodium citrate buffer. Most preferably, in the herein provided methods the sample is a sample of an antibody, which is formulated with an about 25 mM Na-citrate buffer and about 700 mg/l polysorbate 80 and has a pH value of about 6.5.

In the herein provided sample preparation method or endotoxin determination method it is preferred that said antibody (i.e. the antibody that is comprised in the sample) is an anti-CD20 antibody. More preferably, the antibody is the anti-CD20 antibody rituximab. The amino acid sequences of the heavy and light chain of rituximab are shown herein as SEQ ID NOs: 1 and 2, respectively. The person skilled in the art readily knows how to obtain a coding nucleic acid sequence from a given amino acid sequence. Thus, with the knowledge of SEQ ID NOs: 1 and 2, a coding nucleic acid sequence of rituximab can easily be obtained. Rituximab is commercially available, e.g., as Rituxan® and MabThera®, or Zytux®.

In step (a) of the herein provided sample preparation method or endotoxin determination method, magnesium ions ($Mg^{2+}$), e.g. in form of $MgCl_2$, are added to the sample (i.e. to the sample comprising an antibody). Herein, the term "magnesium chloride" or "$MgCl_2$" refers to the chemical compounds with the formula $MgCl_2$ as well as its various hydrates $MgCl_2 (H_2O)_x$ (i.e. $MgCl_2.x\, H_2O$). For example, in step (a) of the herein provided methods $MgCl_2$ hexahydrate (i.e. $MgCl_2.6H_2O$) may be added to the sample. The illustrative appended Examples demonstrate that in step (a) addition of magnesium ions to a final concentration of 10-100 mM $Mg^{2+}$ markedly reduces the LER effect. Moreover, the appended Examples also show that a concentration of $Mg^{2+}$ that is twice the concentration of the buffer of the sample results in best endotoxin recovery rates. For example, when rituximab was used as a sample, best endotoxin recovery rates were obtained when in step (a) the addition of the magnesium salt $MgCl_2$ results in a final concentration of $Mg^{2+}$ that is twice of the sodium citrate concentration (i.e. 50 mM $Mg^{2+}$). Therefore, in step (a) of the herein provided methods it is envisaged that magnesium ions in form of a salt (e.g. $MgCl_2$) are added to result in a final $Mg^{2+}$ concentration that is twice the concentration of the buffer (e.g. the sodium citrate buffer). For example, in the methods provided herein, preferably magnesium ions are added to the sample so that the final concentration of $Mg^{2+}$ [in step (a)] is 10-100 mM $Mg^{2+}$, more preferably 25-75 mM $Mg^{2+}$, even more preferably 40-75 mM $Mg^{2+}$, and most preferably about 50 mM $Mg^{2+}$ (i.e. 45-55 mM $Mg^{2+}$). Or, if the sample already comprises magnesium ions, then the added amount of $Mg^{2+}$ is adjusted so that the resulting final concentration of $Mg^{2+}$ [in step (a)] is preferably 10-100 mM, more preferably 25-75 mM, even more preferably 40-75 mM, and most preferably of about 50 mM $Mg^{2+}$ (i.e. 45-55 mM $Mg^{2+}$). After step (a), i.e. in step (b), the sample is diluted. However, in step (a), the term "adding magnesium ions to a concentration of . . . " or grammatical variations thereof and the term "adding magnesium ions to a final concentration of . . . " or grammatical variations thereof, refer to the final concentration of $Mg^{2+}$ in step (a). For example, adding in step (a) $MgCl_2$ to a (final) concentration of 45-55 mM $MgCl_2$ means that after addition of $MgCl_2$ in step (a) the concentration of $MgCl_2$ is 45-55 mM. Accordingly, if, e.g., in step (b) the sample is diluted at a ratio of 1:10 (sample:buffer/water), the concentration of the magnesium ions and likewise that of $MgCl_2$ is 4.5-5.5 mM.

The appended Examples demonstrate that an incubation step after addition of magnesium ions further improves the recovery rates in the LAL assay. Therefore, in the herein provided methods, after addition of magnesium ions the sample is preferably incubated for 30 min to 6 hours, more preferably for 1-4 hours, most preferably for about 1 hour. In one prioritized aspect of step (a) of the herein provided methods the sample is incubated for about 1 hour at room temperature after addition of the magnesium ions. Before and after said incubation step, the sample may be shaken [e.g. in the Heidolph Multi Reax shaker, high speed (2,037 rpm)]. For example, before and after the incubation step the sample may be shaken for 30 sec to 10 min, preferably for 1 min.

In step (b) of the herein provided sample preparation method or endotoxin determination method, the sample (i.e. the sample comprising an antibody) is diluted. The sample may be diluted with endotoxin-free water. The appended Examples demonstrate that good recovery rates can be obtained if during dialysis the sample has a pH-value of 5.7-8.0. Even better recovery rates were obtained if during dialysis the sample had a pH-value of 6.0-8.0. Best recovery rates were obtained if during dialysis the sample had a pH-value of 6.5-7.5. Thus, one aspect of the invention relates to the herein provided methods, wherein in step (b) the sample is diluted with endotoxin-free water, and wherein after dilution and prior to dialysis the pH-value of the sample is adjusted to 5.7-8.0, more preferably to 6.0-8.0, most preferably to 6.5-7.5. Thus, in one aspect of the invention, in step (b) of the herein provided methods the pH-value of the sample is adjusted to pH 5.7-8.0, more preferably to pH 6.0-8.0. Most preferably, in step (b) of the herein provided methods the pH-value of the sample is adjusted to pH 6.5-7.5. For example, the pH-value of the sample may be adjusted to pH 5.7, pH 5.8, pH 5.9, pH 6.0, pH 6.1, pH 6.2, pH 6.3, pH 6.4, pH 6.5, pH 6.6, pH 6.7, pH 6.8, pH 6.9, or pH 7.0. However, it is preferred herein that the pH-value of the sample is adjusted in step (b) by diluting the sample with 10-50 mM buffer, e.g. Tris/HCl-buffer, pH 6.0-9.0, more preferably with 10-50 mM buffer, e.g. Tris/HCl buffer, pH 6.0-8.0. Therefore, it is envisaged in a preferred aspect of the herein provided methods that in step (c) the pH-value of the sample is adjusted by diluting the sample with 10-50 mM Tris/HCl buffer, pH 6.0-9.0. More preferably, the pH-value of the sample is adjusted by diluting the sample with a 10-50 mM Tris/HCl buffer, pH 6.0-8.0. Most preferably, the pH-value of the sample is adjusted by diluting the sample (in step (b)) with 50 mM Tris/HCl pH ~7.0. Thus, in the herein provided methods, during dialysis in step (c) the sample has a pH-value of 5.7-8.0, preferably of 6.0-8.0, more preferably 6.5-7.5.

As indicated above, the sample can comprises a detergent such as polysorbate 80. The appended illustrative Examples demonstrate that inter alia dilution of a sample comprising a detergent (e.g. polysorbate 80) renders the endotoxin molecules accessible in the LAL assay. Without being bound by theory it is believed that dilution of a sample comprising a detergent to near-CMC concentrations reduces the micellar compartmentalization of the sample, and therefore reduces the LER effect.

The appended Examples show that a dilution of 1:5 to 1:20 considerably influences the recovery rate in a LAL assay. Thus, the invention relates to the herein provided sample preparation method and endotoxin determination method, wherein in step (b) the sample is diluted at a ratio of 1:5 to 1:20 (sample:buffer/water), preferably of 1:10 (sample:buffer/water). In the herein provided methods the antibody is preferably formulated with an about 25 mM sodium citrate buffer and about 700 mg/l polysorbate 80. Thus, in the herein provided methods, the sample may be diluted in step (b) such that the concentration of the buffer decreases to 5-1.25 mM, preferably to 2.5 mM. In addition, the sample may be diluted in step (b) such that the concentration of the detergent decreases to 140-35 mg/l, preferably to 70 mg/l. In the appended Examples, the samples were antibody formulations having a concentration of the antibody of about 10 mg/ml. These samples were diluted in step (b) of the inventive methods to result in an antibody concentration of 2-0.5 mg/ml. Thus, in the herein provided methods, the sample may be diluted in step (b) such that the concentration of the antibody decreases to 2-0.5 mg/ml, preferably to 1 mg/ml. In the herein provided methods also an undiluted control may be prepared. Said undiluted control is treated in the same way as the sample to be tested, with the exception that the undiluted control is not diluted (in step (b)). Herein, "buffer/water" means "buffer or water".

In step (c) of the herein provided sample preparation method and endotoxin determination method, the sample is dialyzed against an endotoxin-free aqueous solution. The endotoxin-free aqueous solution may be endotoxin-free water. However, said endotoxin-free aqueous solution may also be an endotoxin-free aqueous solution that comprises magnesium ions, e.g. added in form of the salt $MgCl_2$. Accordingly, one aspect of the invention relates to the herein provided methods, wherein in step (c) the endotoxin-free aqueous solution contains magnesium ions, e.g. 2.5-10 mM $MgCl_2$.

Before starting the dialysis, the samples may be shaken [e.g. in a Heidolph Multi Reax shaker, high speed (2,037 rpm) at room temperature], e.g. for 30 sec to 10 min, preferably for 1 min. Preferably, the dialysis in step (c) is for 1-48 hours, more preferably for 4-24 hours, most preferably for about 24 hours. Thus, it is preferred that in step (c) the dialysis is for about 24 hours. The dialysis may be performed at 15-30° C., preferably at room temperature (i.e. 21±2° C.). After dialysis, the sample may be shaken [e.g. in a Heidolph Multi Reax shaker, high speed (2,037 rpm) at room temperature, e.g. for 20 min to 1 hour, preferably for (at least) 20 min.

The dialysis may be performed by using a Spin Dialyzer (e.g. the Harvard SpinDIALYZER, catalogue Nb. 74-0314) or a Fast Spin Dialyzer (e.g. the Harvard Fast Spin Dialyzer, catalogue Nb. 74-0412). It is preferred (especially if a Fast Spin Dialyzer is used) that the rotation frequency of the stirrer is high, meaning that the frequency of the stirrer is 50 to 300 rpm, preferably 200 to 300 rpm. The stirrer has preferably a length of 20-60 mm and a diameter (i.e. cross-section dimension) of 5-25 mm. More preferably, the stirrer has a length of about 40 mm and a diameter of about 14 mm. The stirrer is most preferably a heat-sterilized (e.g. 4 hours at 250° C.) magnetic stirrer having a length of about 40 mm and a diameter of about 14 mm. Such stirrers are available from OMNILAB. Indeed dialysis is usually done with a high frequency of the stirrer, as this facilitates diffusion through the dialysis membrane. Accordingly, dialyzing with a high frequency of the stirrer is the standard dialysis procedure. The vessel that is used for dialysis has preferably a volume of 500-5000 ml, more preferably 1000-3000 ml, most preferably 1500-2500 ml. This vessel may have a diameter of 120 mm and a height of 240 mm. For example, the vessel that is used for dialysis may be a DURAN® beaker, tall form, 2000 ml (e.g. available from OMNILAB, Germany, P/N: 5013163). Using a Fast Spin Dialyzer is preferred as it has the double area of dialysis membrane, and thus is believed to be suitable for a more efficient and quicker dialysis.

It is envisaged that for the dialysis in step (c) a membrane with a molecular-weight cut-off of 100 Da to 16 kDa, preferably of 500 Da to 10 kDa, most preferably of 10 kDa is used. For the dialysis in step (c) a cellulose ester or a cellulose acetate membrane may be used. Preferably, for the dialysis in step (c) a cellulose acetate membrane is used. Most preferably, a cellulose acetate membrane with a molecular-weight-cut-off of 10 kDa is used during the dialysis.

Thus, in step (c) of the herein provided methods, the dialysis is preferably performed for about 24 hours by using a cellulose acetate membrane with a molecular-weight cut-off of 10 kDa. Before the dialysis, the dialysis membrane may be washed, preferably in endotoxin-free water. In particular, the dialysis membrane may be shaked (e.g. with the Shaker SG 20. IDL GmbH, Germany or equivalent, 50 to 300 rpm, preferably 100 rpm) in endotoxin-free water. For example, the dialysis membrane may be washed by shaking it for 10 min to 3 hours, preferably for 1 hour in endotoxin-free water. After this washing step, the dialysis membrane is preferably transferred in fresh endotoxin-free water and again washed by shaking it for 10 in to 3 hours, preferably for 1 hour.

The dialysis may be performed in 1 ml chambers, e.g. in 1 ml spin dialyzer (Harvard) chambers equipped with a membrane (such as cellulose acetate membrane) having a molecular-weight cut-off ranging from 500 Da to 10 kDa (e.g. a molecular-weight cut-off of 10 kDa). During dialysis the water is preferably changed, more preferably the water is changed twice. For example, the water may be changed after 2 and 20 hours of dialysis or after 18 and 22 hours of dialysis. Preferably, the water is changed after 2 and 4 hours of dialysis.

It is preferred in context of the herein provided methods that after the dialysis in step (c) the sample is shaked [e.g. in a Heidolph Multi Reax shaker, high speed (2,037 rpm) at room temperature. Preferably, the sample (i.e. the sample comprising an antibody) is shaked after dialysis for 10 min to 1 hour, more preferably for 20 min. In addition or alternatively to shaking, the sample may be treated with ultrasound after dialysis. Thus, one aspect of the invention relates to the herein provided methods, wherein in step (c) the sample is treated with ultrasound after dialysis.

If the herein provided sample preparation method is combined with a LAL assay, then this combined method advantageously reaches the FDA requirements for the quantitative and reproductive detection of a defined amount of CSE spiked to a sample. Preferably, the LAL assay of the herein provided methods is a LAL assay as described below.

The appended Examples indicate that addition of $Mg^{2+}$ (i.e. magnesium ions) has the further advantage that it retains the endotoxin in the inner compartment of the dialysis chamber. Thus, the dialysis in step (c) leads only to the removal of the buffer (e.g. the sodium citrate buffer) and not of the endotoxin. The dilution step may reduce the concentration of the detergent (e.g. polysorbate 80) so as to abolish the inhibition of the LAL cascade by the detergent. The appended Examples demonstrate that the LER effect can in particular reproducibly be overcome if the steps of the inventive methods are performed in the order: (1) addition of $Mg^{2+}$; (2) dilution; and (3) dialysis. Accordingly, the combination of the steps (1), (2) and (3), or the combination of the claimed steps (a), (b) and (c) reproducibly overcomes the LER effect. The preferred amount of $Mg^{2+}$ that is to be added, the preferred degree of dilution and the preferred parameters for dialysis are detailed herein above and below.

In a preferred aspect, the invention relates to the herein provided method for the preparation of a sample comprising an antibody for a LAL assay, wherein the method comprises the following steps in the following order:
  (a) adding magnesium ions, e.g. in form of $MgCl_2$, to the sample to a final concentration of 10-100 mM, preferably 40-75 mM, most preferably 45-55 mM,
  (b) diluting the sample at a ratio of 1:5 (sample:buffer) to 1:20 (sample:buffer), preferably 1:10 (sample:buffer) with 10-50 mM Tris/HCl buffer, pH 6.0-8.0; preferably with 50 mM Tris/HCl-buffer, pH ~7.0,
  (c) dialyzing the sample having a pH-value of 5.7-8.0 (preferably 6.5-7.5) against endotoxin-free water for 1-48 hours, preferably for 4-24 hours, most preferably for 24 hours. Preferably a cellulose acetate membrane with a molecular weight cut-off of 10 kDa is used and the water is changed after 2 and 4 hours. Most preferably, a Fast Spin Dialyzer is used and the frequency of the stirrer is 50 to 300 rpm preferably 200 rpm.

As mentioned above, the antibody is preferably a monoclonal antibody. More preferably, the antibody is rituximab. Most preferably, in the herein provided methods the sample is a sample of an antibody, which is formulated with an about 25 mM sodium citrate buffer (7.35 mg/ml) and about 700 mg/l polysorbate 80 and has a pH value of about 6.

The term "about" and the symbol "~" are used interchangeably herein and specify that the specific value provided may vary to a certain extent. For example, "about" or "~" (e.g. in the context of about/~25 mM sodium citrate buffer) means that variations in the range of ±10%, preferably ±5%, most preferably ±2% are included in the given value.

As indicated, it is envisaged in context of the present invention that the herein provided sample preparation method is combined with a LAL assay. The LAL assay has the advantage that it detects endotoxin at low concentration.

As given by the CSE standard curve the validated lower limit of endotoxin detection is 0.005 EU/mL in kinetic chromogenic LAL techniques. The LAL reagent of these techniques comprises the complete enzymatic amplification cascade of serine proteases purified from the *Limulus* crab.

The lower limit of endotoxin (CSE) detection in the more recently developed EndoLISA® assay (Hyglos GmbH, Germany) is indicated by the manufacturer to be 0.05 EU/mL (Advertisment of Hyglos: Grallert, et al, in: *Nature Methods*, October 2011). This EndoLISA® assay employs a recombinant form of only the initial enzyme of the *Limulus* cascade, i.e. factor C. Distinct from certified LAL tests the EndoLISA® assay additionally includes an initial endotoxin adsorption step provided by a pre-coating of the micotiter plate by a bacteriophage-encoded protein that yet has not been proven to bind the broad spectrum of bacterial endotoxins well known to be detected by the LAL method.

In particular, in a preferred aspect the present invention relates to a method for determining bacterial endotoxin in a sample comprising a polypeptide, wherein the method comprises the following steps in the following order:

(a) adding magnesium ions, preferably in form of $MgCl_2$, to the sample to a final concentration of 10-100 mM, preferably 40-75 mM, most preferably 45-55 mM, (b) diluting the sample at a ratio of 1:5 (sample:buffer) to 1:20 (sample:buffer), preferably 1:10 (sample:buffer) with 10-50 mM Tris/HCl buffer, pH 6.0-8.0; preferably with 50 mM Tris/HCl-buffer, pH ~7.0, (c) dialyzing the sample having a pH-value of 5.7-8.0 (preferably 6.5-7.5) against endotoxin-free water for 1-48 hours, preferably for 4-24 hours, most preferably for 24 hours. Preferably a cellulose acetate membrane with a molecular weight cut-off of 10 kDa is used and the water is changed after 2 and 4 hours. Most preferably, a Fast Spin Dialyzer is used and the frequency of the stirrer is 50 to 300 rpm preferably 200 rpm.

(d) Determining bacterial endotoxin in the sample by using a LAL assay.

As mentioned above, the antibody is preferably a monoclonal antibody. More preferably, the antibody is rituximab. Most preferably, in the herein provided methods the sample is a sample of an antibody, which is formulated with an about 25 mM sodium citrate buffer and about 700 mg/l polysorbate 80 and has a pH value of about 6.5.

As indicated in the appended Examples, a "LER positive control" (also designated as "positive LER control") may be used in the LAL assay of step (d) of the herein provided endotoxin determination method. Said "LER positive control" is an indicator to demonstrate that the sample to be tested (i.e. the sample comprising an antibody) would exhibit the LER effect if the steps (a) to (c) of the herein described methods would not have been performed. Or, in other words, the "LER positive control" is used in a LAL assay as a positive control to show that a known spiked amount of endotoxin (within the sample to be tested) cannot be recovered by using a LAL assay only (i.e. without performing steps (a) to (c) of the herein provided methods). In context of the present invention it has surprisingly and unexpectedly been found that a positive LER effect can only be obtained if, after spiking the sample with CSE, the sample is shaked for 45 min to 2 hours, preferably for about 60 min to 2 hours, most preferably for about 60 min.

Thus, in context of the present invention the "LER positive control" is prepared by spiking a known amount of endotoxin into an aliquot of the sample to be tested for endotoxin (e.g. into an aliquot of the sample comprising an antibody) and shaking the spiked sample for 45 min to 2 hours, preferably for about 60 min to 2 hours, most preferably for about 60 min. Thus, the invention relates to the herein provided endotoxin determination method, further comprising producing a LER positive control by spiking a known amount of endotoxin into an aliquot of the sample and shaking the endotoxin spiked aliquot of the sample for ≥60 min (more preferably for 60 min to 2 hours).

Preferably, in the herein provided method for determining bacterial endotoxin the "LER positive control" is prepared by spiking CSE to a final concentration of 5.0 EU/ml to an aliquot of the sample to be tested. Afterwards, the spiked aliquot is shaked [e.g. in a Heidolph Multi Reax shaker, high speed (2,037 rpm) at room temperature] for ≥60 min, most preferably for 60 min. After shaking, the endotoxin spiked aliquot is preferably diluted to the same extend as the sample to be tested in step (b) of the herein provided methods. Preferably, the spiked aliquot is diluted with endotoxin-free water. After dilution, the spiked aliquot is preferably shaked [e.g. in a Heidolph Multi Reax shaker, high speed (2,037 rpm) at room temperature], e.g. for 1 min.

Thus, the "LER positive control" is preferably prepared by the following procedure in the following order:

Spiking CSE to a final concentration of 5.0 EU/ml to an aliquot of the sample to be tested. Preferably, the "LER positive control" is prepared in a 1.5-5 ml clear glass, crimp neck, flat bottom vessel, more preferably in a screw neck glass vial of Macherey-Nagel GmbH (1.5 ml or 4 ml)

Shaking the spiked aliquot for ≥60 min (more preferably for 60 min to 2 hours), most preferably for 60 min. Preferably, the spiked aliquot is shaked at high speed (2,037 rpm) at room temperature (i.e. 21±2° C.). Most preferably the spiked aliquot is shaked at high speed (2,037 rpm) in a Heidolph Multi Reax shaker at room temperature.

Diluting the spiked aliquot with endotoxin-free water. The spiked aliquot is diluted to the same extend as the sample to be tested in step (b) of the herein provided methods (i.e. if the sample to be tested is diluted in step (b) at a ratio of 1:10, then also the spiked aliquot is diluted at a ratio of 1:10).

Shaking the spiked aliquot (e.g. for 1 min).

As described above, during preparation of the "LER positive control", a dilution is performed. However, it is envisaged in context of the present invention that, beside said dilution, the "LER positive control" is not treated as described in steps (a) to (c) of the herein provided methods. However, said "LER positive control" is used in step (d) of the method for determining bacterial endotoxin to show that the sample to be tested (i.e. the sample comprising an antibody) would exhibit the LER effect if the steps (a) to (c) of the herein described methods would not be performed. The "LER positive control" may be prepared during the time of any one of steps (a) to (c) (e.g. during dialysis-time) so that it is ready for use when the LAL assay is performed.

To identify that a given material (e.g. a buffer or a sample of a therapeutic antibody) exhibits the LER effect, endotoxin contents can be monitored over time, e.g. in an endotoxin hold time study. Endotoxin hold time studies require endotoxin spiking of an undiluted sample and storage of the endotoxin spiked sample over time. For example, the sample may be stored up to several months. Preferably, in a hold time study the endotoxin spiked sample is stored for several (e.g. 7 for up to 28) days and at defined time points a LAL assay is performed. Recovery rates that are lower than 50% of the amount of the spiked endotoxin indicate that the sample exhibits a LER effect.

As mentioned above, the LAL assay is routinely performed with a diluted test sample along with a diluted positive control (PPC), which is a sample with a known amount of spiked CSE. Thus, in the LAL assay, which is performed in step (d) of the herein provided endotoxin determination method, it is envisaged that every sample is measured each time in duplicate with a spiked control standard endotoxin (PPC) and without spiked endotoxin. Consequently, with every given sample, it can easily be tested whether the herein provided sample preparation method or the herein provided endotoxin determination method has the favorable effect that the endotoxin present in the sample (or at least 50-200% thereof as required by the FDA) can be detected by using the LAL assay. Thus, it is envisaged that the LAL assay in step (d) of the herein provided endotoxin determination method comprises that a positive control (PPC) is tested along with the sample to be tested (i.e. the sample comprising an antibody to be tested). Said positive control is identical to the sample to be tested with the exception that the PPC is spiked with a known amount of CSE. Or, in other words, steps (a) to (c) of the herein provided methods have to be performed with the PPC in the same way as with the sample to be tested. Accordingly, the PPC is prepared before step (a) of the herein provided methods.

In context of the present invention it has surprisingly and unexpectedly been found that a positive LER effect can only be obtained if, after spiking the sample with CSE, the sample is shaked for 45 min to 2 hours, preferably for about 60 min to 2 hours, most preferably for about 60 min. Thus, in context of the present invention the PPC is shaked [e.g. in a Heidolph Multi Reax shaker, high speed (2,037 rpm)] after spiking for 45 min to 2 hours, preferably for about 60 min to 2 hours, most preferably for about 60 min. More preferably, the PPC is shaked [e.g. in a Heidolph Multi Reax shaker, high speed (2,037 rpm)] after spiking for about 60 min at room temperature.

Thus, a preferred aspect of the invention relates to the herein provided method for determining bacterial endotoxin in a sample comprising an antibody, wherein the method comprises the following steps in the following order:
(a0) preparing a PPC by
spiking a known amount of endotoxin into a first aliquot of the sample comprising an antibody, and
shaking the endotoxin spiked aliquot for 60 min to 2 hours (preferably for about 60 min at room temperature),
(a) adding magnesium ions to a second aliquot of the sample to be tested as well as to the PPC,
(b) diluting the second aliquot of the sample to be tested as well as the PPC,
(c) dialyzing the second aliquot of the sample having a pH-value of 5.7-8.0 (preferably 5.8-7.0) to be tested as well as the PPC against an endotoxin-free aqueous solution, wherein the sample to be tested as well as the PPC have a pH-value of 5.7-9.0, and
(d) determining bacterial endotoxin in the second aliquot of the sample to be tested as well as in the PPC by using a LAL assay.

In one aspect of the invention, the PPC is spiked with endotoxin such that a final endotoxin concentration of 5.0 EU/ml is obtained.

All the aspects and definitions disclosed in connection with the herein provided method for determining bacterial endotoxin apply, mutatis mutandis, to said method if a PPC is applied. Thus, a preferred aspect of the invention relates to the herein provided method for determining bacterial endotoxin in a sample comprising an antibody, wherein the method comprises the following steps in the following order:
(a0) preparing a PPC by
spiking a known amount of endotoxin into a first aliquot of the sample comprising an antibody, and
shaking the endotoxin spiked aliquot for ≥60 min (preferably for 60 min at room temperature),
(a) adding magnesium ions, preferably in form of $MgCl_2$, to a second aliquot of the sample to a final concentration of 10-100 mM, preferably 40-75 mM, most preferably 45-55 mM,
(b) diluting the second aliquot of the sample at a ratio of 1:5 (sample:buffer) to 1:20 (sample:buffer), preferably 1:10 (sample:buffer) with 10-50 mM Tris/HCl-buffer, pH 6.0-8.0, preferably with 50 mM Tris/HCl-buffer, pH ~7.0,
(c) dialyzing the sample having a pH-value of 5.7-8.0 (preferably 6.5-7.5) against endotoxin-free water for 1-48 hours, preferably 4-24 hours, most preferably 24 hours. Preferably a cellulose acetate membrane with a molecular weight cut-off of 10 kDa is used and the water is changed after 2 and 4 hours. More preferably, a Fast Spin Dialyzer is used and the frequency of the stirrer is high.
(d) Determining bacterial endotoxin in the sample by using a LAL assay.

Additionally water controls can be applied in the herein provided endotoxin determination method. Preferably, at least two water controls are used; wherein one consisting of endotoxin-free water and the other of endotoxin-free water, which is spiked with a known amount of endotoxin (e.g. resulting in a final concentration of 5.0 EU/ml CSE). The water controls are treated in the same manner as the sample to be tested.

As indicated above, in the herein provided sample preparation method as well as in the herein provided endotoxin determination method, it is envisaged that in step (a), the sample is incubated for 30 min to 6 hours, preferably for 1-4 hours, most preferably for 1. Moreover, it is also envisaged that after dialysis the sample is shaked [e.g. in a Heidolph Multi Reax shaker, high speed (2,037 rpm) at room temperature], e.g. for 10 min to 1 hour, preferably for 20 min. Thus, one aspect of the invention relates to the herein provided method for the preparation of a sample comprising an antibody for a LAL assay, wherein the method comprises the following steps in the following order:
(a) adding magnesium ions, preferably in form of $MgCl_2$, to the sample to a final concentration of 10-100 mM, preferably 40-75 mM, most preferably 45-55 mM; and incubating the sample for 30 min to 6 hours, preferably for 1-4 hours, most preferably for 1 hour,
(b) diluting the sample at a ratio of 1:5 (sample:buffer) to 1:20 (sample:buffer), preferably 1:10 (sample:buffer) with 10-50 mM Tris/HCl-buffer, pH 6.0-8.0, preferably with 50 mM Tris/HCl-buffer, pH ~7.0,
(c) dialyzing the sample having a pH-value of 5.7-8.0 (preferably 6.5-7.5) against endotoxin-free water for 1-48 hours, preferably for 4-24 hours, most preferably for 24 hours. (Preferably, a cellulose acetate membrane with a molecular weight cut-off of 10 kDa is used and the water is changed after 2 and 4 hours. Most preferably, a Fast Spin Dialyzer is used and the frequency of the stirrer is high.) After dialysis, the samples are shaked for 10 min to 1 hour, preferably for 20 min.

Analogously, a further aspect of the invention relates to the herein provided method for determining bacterial endotoxin in a sample comprising an antibody exhibiting a LER effect, wherein the method comprises the following steps in the following order:
(a) adding magnesium ions, preferably in form of $MgCl_2$, to the sample to a final concentration of 10-100 mM, preferably 40-75 mM, most preferably 45-55 mM; and incubating the sample for 30 min to 6 hours, preferably for 1-4 hours, most preferably for 1 hour (wherein the sample may be shaked before and after the incubation), (b) diluting the sample at a ratio of 1:5 (sample:buffer) to 1:20 (sample:buffer), preferably 1:10 (sample:buffer) with 10-50 mM Tris/HCl-buffer, pH 6.0-8.0, preferably with 50 mM Tris/HCl-buffer, pH ~7.0, (c) dialyzing the sample having a pH-value of 5.7-8.0 (preferably 6.5-7.5) against endotoxin-free water for 1-48 hours, preferably for 4-24 hours, most preferably for 24 hours. (Preferably, a cellulose acetate membrane with a molecular weight cut-off of 10 kDa is used and the water is changed after 2 and 4 hours. Most preferably, a Fast Spin Dialyzer is used and the frequency of the stirrer is high.) After dialysis, the samples are shaked for 10 min to 1 hour, preferably for 20 min.

(d) Determining bacterial endotoxin in the sample by using a LAL assay.

Moreover, as mentioned above, in herein provided endotoxin determination method it is envisaged that a PPC is prepared and that the PPC is shaked for 60 min to 2 hours after spiking. Thus, the present invention relates to the herein provided method for determining bacterial endotoxin in a sample comprising an antibody exhibiting a LER effect, wherein the method comprises the following steps in the following order:

(a0) preparing a PPC by
spiking a known amount of endotoxin (e.g. to a final concentration of 5.0 EU/ml) into a first aliquot of the sample comprising an antibody, and
shaking the endotoxin spiked aliquot for 60 min to 2 hours (preferably for 60 min at room temperature), (a) adding magnesium ions, preferably in form of $MgCl_2$, to a second aliquot of the sample as well as to the PPC to a final concentration of 10-100 mM, preferably 40-75 mM, most preferably 45-55 $MgCl_2$; (and preferably incubating the sample and the PPC for 30 min to 6 hours, more preferably for 1-4 hours, most preferably for 1 hour, (wherein the sample may be shaked before and after the incubation)), (b) diluting the sample and the PPC at a ratio of 1:5 (sample/PPC:buffer) to 1:20 (sample/PPC:buffer), preferably 1:10 (sample/PPC:buffer) with 10-50 mM Tris/HCl-buffer, pH 6.0-8.0, preferably with 50 mM Tris/HCl-buffer, pH ~7.0, (c) dialyzing the sample having a pH-value of 5.7-8.0 (preferably 6.5-7.5) and the PPC against endotoxin-free water for 1-48 hours, preferably for 4-24 hours, most preferably for 24 hours. (Preferably, a cellulose acetate membrane with a molecular weight cut-off of 10 kDa is used and the water is changed after 2 and 4 hours. Most preferably, a Fast Spin Dialyzer is used and the frequency of the stirrer is high.) After dialysis, the samples and the PPC are shaked for 10 min to 1 hour, preferably for 20 min.

(d) determining bacterial endotoxin in the sample and the PPC by using a LAL assay.

In addition, as indicated above, it is envisaged in the herein provided endotoxin determination method that a "LER positive control" is prepared and used in step (d) to show the LER effect. Thus, a preferred aspect of the invention relates to the herein provided method for determining bacterial endotoxin in a sample comprising an antibody exhibiting a LER effect, wherein the method comprises the following steps in the following order:

(a0) preparing a PPC by
spiking a known amount of endotoxin (e.g. to a final concentration of 5.0 EU/ml) into a first aliquot of the sample comprising an antibody, and
shaking the endotoxin spiked aliquot for 60 min to 2 hours (preferably for 60 min at room temperature), (a) adding magnesium ions, preferably in form of $MgCl_2$, to a second aliquot of the sample as well as to the PPC to a final concentration of 10-100 mM, preferably 40-75 mM, most preferably 45-55 mM; (and preferably incubating the sample and the PPC for 30 min to 6 hours, more preferably for 1-4 hours, most preferably for 1 hour, (wherein the sample may be shaked before and after the incubation)), (b) diluting the sample and the PPC at a ratio of 1:5 (sample/PPC:buffer) to 1:20 (sample/PPC:buffer), preferably 1:10 (sample/PPC:buffer) with 10-50 mM Tris/HCl-buffer, pH 6.0-8.0, preferably with 50 mM Tris/HCl-buffer, pH ~7.0, (c) dialyzing the sample having a pH-value of 5.7-8.0 (preferably 6.5-7.5) and the PPC against endotoxin-free water for 1-48 hours, preferably for 4-24 hours, most preferably for 24 hours. (Preferably, a cellulose acetate membrane with a molecular weight cut-off of 10 kDa is used and the water is changed after 2 and 4 hours. Most preferably, a Fast Spin Dialyzer is used and the frequency of the stirrer is high.) After dialysis, the samples and the PPC are shaked for 10 min to 1 hour, preferably for 20 min.

(d) Determining bacterial endotoxin in the sample and the PPC by using a LAL assay, wherein in the LAL assay a "LER positive control" is used, which is prepared by:
spiking CSE to a final concentration of 5.0 EU/ml to a third aliquot of the sample to be tested;
shaking the spiked aliquot for ≥60 min, most preferably for 60 min;
diluting the spiked aliquot with endotoxin-free water (the spiked aliquot is diluted to the same extend as the sample to be tested in step (b) of the herein provided methods);
shaking the spiked aliquot (e.g. for 1 min).

Thus, a preferred aspect of the invention relates to the herein provided method for determining bacterial endotoxin in a sample comprising an antibody exhibiting a LER effect, wherein the method comprises the following steps in the following order:

(a0) preparing a PPC by
spiking a known amount of endotoxin to a final concentration of 5.0 EU/ml into a first aliquot of the sample comprising an antibody, and
shaking the endotoxin spiked aliquot for about 60 min at room temperature, (a) adding magnesium ions, preferably in form of $MgCl_2$, to a second aliquot of the sample and the PPC to a final concentration of 45-55 mM, shaking the sample and the PPC for 1 min, incubating the sample and the PPC for 1 hour, and shaking the sample and the PPC again after the incubation, (b) diluting the sample and the PPC 1:10 (sample/PPC:buffer) with 50 mM Tris/HCl-buffer, pH ~7.0, (c) dialyzing the sample having a pH-value of 5.7-8.0 (preferably 6.5-7.5) and the PPC against endotoxin-free water for 24 hours by using a cellulose acetate membrane with a molecular weight cut-off of 10 kDa; wherein the water is changed after 2 and 4 hours (preferably, a Fast Spin Dialyzer is used and the frequency of the stirrer is high), and shaking the sample and the PPC for 20 min, and (d) determining bacterial endotoxin in the sample and the PPC by using a LAL assay, wherein in the LAL assay a "LER positive control" is used, which is prepared by spiking CSE to a final concentration of 5.0 EU/ml to a third aliquot of the sample to be tested,
shaking the spiked aliquot for 60 min,
diluting the spiked aliquot at a ratio of 1:10 with endotoxin-free water,
shaking the spiked aliquot (e.g. for 1 min).

In addition, as mentioned above, it is envisaged that water controls are applied in the LAL assay. For example, a water control that consists of endotoxin-free water may be applied in the LAL assay of step (d) of the herein provided endotoxin determination method. Another water control may consist of endotoxin spiked endotoxin-free water. After endotoxin spiking, the water is preferably shaked [e.g. in a Heidolph Multi Reax shaker, high speed (2,037 rpm)] for ≥60 min (e.g. for 60 min at room temperature). In addition, in a LAL assay a standard is normally prepared according to the instructions of the used kit.

Steps (a0), (a), (b), (c) and (d) are to be conducted in the order (a0)→(a)→(b)→(c)→(d). However, washing of the dialysis membrane can be performed at any time, provided that the step is executed when the dialysis starts. Similarly, preparation of the LER positive control can be performed at any time provided that the step is executed when the LAL assay starts. In a preferred aspect of the invention, the herein provided endotoxin determination method comprises the following steps.

Step (a00): Preparation of the Samples
    Adapting the concentration of the sample to be tested to the PPC (e.g. antibody 900 µl+100 µl endotoxin-free water)
    Spiking an aliquot of the sample to be tested with endotoxin for the production of the PPC (e.g. antibody 900 µl+100 µl CSE conc. 50 EU/ml=final conc. 5.0 EU/ml)
    Preparing a water control (e.g. endotoxin-free water 1000 µl)
    Preparing another water control (e.g. endotoxin-free water 900 µl+100 µl CSE conc. 50 EU/ml=final conc. 5.0 EU/ml)
    Shake the samples about 60 min at room temperature [e.g. in a Heidolph Multi Reax shaker, high speed (2,037 rpm)], Step (a01): Washing of the Dialysis Membrane
    For example, use 10 kDa cellulose acetate (CA) membranes and put them into a crystallizing dish with endotoxin-free water (e.g. 300 ml of distilled water of the manufacturer B. Braun, Melsungen)
    Shake them carefully for 1 h (Shaker SG 20. IDL GmbH, Germany or equivalent, 50 to 300 rpm, preferably 100 rpm)
    Transfer the membranes into an new crystallizing dish with fresh endotoxin-free water (e.g. 300 ml of distilled water of the manufacturer B. Braun, Melsungen)
    Shake (Shaker SG 20. IDL GmbH, Germany or equivalent, 50 to 300 rpm, preferably 100 rpm) them for 1 h Step (a): Addition of 25-100 mM, Preferably 50-100 mM, Magnesium Ions ($Mg^2$)
    Add $Mg^{2+}$, e.g. in form of $MgCl_2$, to the samples of step (a0) to a final concentration of 25-100 mM, preferably 50-100 mM (e.g. add 50 µl of an 1 M $MgCl_2$ stock solution to the samples of step (a0))
    Shake [e.g. in a Heidolph Multi Reax shaker, high speed (2,037 rpm) at room temperature] for 2-5 min, e.g. for 1 min
    Incubate the samples for 45 to 75 minutes, preferably for 60 min, at room temperature
    Shake [e.g. in a Heidolph Multi Reax shaker, high speed (2,037 rpm) at room temperature] for 1 min Step (b): Dilution
    Take one of the samples of step (a) and dilute it 1:10 with buffer pH ~7.0 (e.g. 50 mM Tris/HCl buffer pH ~7.0) (e.g. 895 µl 50 mM Tris-buffer+105 µl sample)
    Preferably prepare two diluted samples
    For example:
        2×antibody 1:10 with Tris-buffer (sample)
        2×antibody spiked with 5.0 EU/ml 1:10 with Tris-buffer (PPC)
        2×LAL water 1:10 with Tris-buffer (background)
        2×LAL water 5.0 EU/ml 1:10 with Tris-buffer (standard)
        LAL-water=please add Step (c): Dialysis
    Shake [e.g. in a Heidolph Multi Reax shaker, high speed (2,037 rpm) at room temperature, all diluted samples for 1 min
    Transfer them into the dialyzer (preferably a FastSpinDIALYZER)
    Put one dialyzer per beaker on a stirrer
    Fill the beaker with endotoxin-free water (e.g. 200 ml of distilled water of the manufacturer B. Braun, Melsungen)
    Dialyze 24 h at room temperature and exchange the endotoxin-free water after 2 h and 4 h
    The frequency of the stirrer is preferably 50 to 300 rpm, more preferably 200 rpm (especially if a FastSpinDIALYZER is used). The stirrer has preferably a length of 20-60 mm and a diameter of 5-25 mm. More preferably, the stirrer is a magnetic stirrer having a length of about 40 mm and a diameter of about 14 mm.

Step (d): Shaking
    After dialysis transfer the samples into new vessels (e.g. into 1.5 ml screw vials) and shake [e.g. in a Heidolph Multi Reax shaker, high speed (2,037 rpm) at room temperature] for 20-60 min Step (d00): Preparation of the "LER Positive Control" and of Further Water Controls
1. (Step (d00) not necessarily has to be performed after step (d). Step (d00) can be performed at any time provided that the "LER positive control" and the further water controls are ready when the LAL assay starts.) Prepare the "LER positive control" (i.e. the "positive LER control") preferably 1 h before the dialysis ends [e.g. antibody 900 µl+100 µl CSE conc. 50 EU/ml=final conc. 5.0 EU/ml]
Prepare further water controls, for example:
    1. antibody 900 µl+100 µl LAL water
    2. LAL water 1000 µl
LAL water 900 µl+100 µl CSE conc. 50 EU/ml=final conc. 5.0 EU/ml
Shake 1 h [e.g. in a Heidolph Multi Reax shaker, high speed (2,037 rpm) at room temperature]
Dilute samples 1:10 with endotoxin-free water
Shake for 1 min [e.g. in a Heidolph Multi Reax shaker, high speed (2,037 rpm) at room temperature]

Step (e): LAL Assay
    Prepare the standard (i.e. the standard that is comprised in the used LAL assay kit) according to the instructions of the manufacturer and start the measurement as follows;
(1) Preparation of LAL Reagent (Kinetic-QCL™ Reagent):
    Reconstitute the co-lyophilized mixture of lysate prepared from the amoebocytes of the horseshoe crab, *Limulus polyphemus*, and chromogenic substrate with 2.6 ml of LAL Reagent Water per vial immediately before use.

(2) Preparation of CSE Stock Solution (50 EU/Ml, i.e. Equivalent to Standard S1):
   Reconstitute the CSE preparation (*E. coli* O55:B5-LPS, each vial contains 50-200 EU lyophilized endotoxin) in the volume of LAL Reagent Water stated on the Certificate of Analysis and calculated to yield a solution containing 50 EU (or IU)/ml.
   Shake the CSE Stock solution vigorously for at least 15 minutes at high speed on a shaker.
   Prior to use, let the solution warm up to room temperature and shake again vigorously at high speed on a shaker for 15 minutes.
(3) Preparation of CSE Standard Series:
   Dilute the CSE stock solution/standard S1 (step 1) with LAL Reagent Water at room temperature in a 1:10 scheme to yield the complete series of CSE standards (50, 5, 0.5, 0.05 and 0.005 EU/ml
(4) LAL Analysis in a 96-Well Microplate ELISA Reader Format:
   Carefully dispense 100 µl of the LAL Reagent Water blank, endotoxin standards, product samples, positive product controls. into the appropriate wells of the microplate.
   Place filled plate in the microplate reader, close the lid. Pre-incubate the plate for ≥10 minutes at 37° C.±1° C.
   Using an 8-channel multipipettor dispense 100 µl of the Kinetic-QCL™ Reagent into all wells of the microplate beginning with the first column (A1-H1) and proceeding in sequence to the last column used. Add reagent as quickly as possible (avoid air bubbles).
   Immediately click on the OK button on the computer keyboard to initiate the test. (Note: The Kinetic-QCL™ assay is performed with the microplate cover removed)
Herein, "spiking" means "adding" or "providing with". For example, "spiking a sample with a known amount of CSE" means "adding a known amount of CSE to a sample" or "providing a sample with a known amount of CSE".

Endotoxins, also known as lipopolysaccharides (LPS), are large molecules found in the outer membrane of Gram-negative bacteria, and elicit strong immune responses in animals, e.g. in humans. As mentioned, the invention provides for a method for determining (i.e. detecting and quantifying) bacterial endotoxin in a sample comprising an antibody, wherein the method comprises the herein described steps (a) to (d) (preferably also including the steps (a00), (a01) and (d00)).

In one embodiment the endotoxin may be *Eschericha coli* endotoxin. Accordingly, the endotoxin that is determined (i.e. detected and/or quantified) in step (d) of the herein provided endotoxin determination method may be *E. coli* endotoxin. For example, the endotoxin that is spiked in the sample during the LAL assay may be *E. coli* endotoxin (i.e. endotoxin purified from *E. coli*). Preferably, the endotoxin is a commercially available *E. coli* endotoxin (e.g. control standard endotoxin, CSE).

The WHO International Standard Endotoxin (I.S.) is an endotoxin preparation from *E. coli* O113:H10:K—that is internationally recognized as the ultimate calibrant for the bacterial endotoxins test. The current lot of the International Standard is termed "WHO International Standard, 3rd I.S. for endotoxin".

An Reference Standard Endotoxin (RSE) is an endotoxin preparation that has been calibrated against the WHO International Standard Endotoxin. RSEs are established by national agencies (like USP, EP, JP, ChP) and provided to calibrate CSEs (see below) for use in the LAL assays.

A Control Standard Endotoxin (CSE) is an endotoxin preparation other than RSE that has been calibrated against an RSE. CSEs are vendor-specific, highly-purified preparations of endotoxins that are produced from *E. coli* O113: H10:K—(e.g. Associates of Cape Cod, Inc.) or other *E. coli* strains like *E. coli* O55:B5 (e.g. Charles River, Lonza). Vendors might add stabilizers like human serum albumin, PEG, or starch at their own discretion. CSEs are supplied in various concentrations, depending on their intended use.

The herein provided method for determining (i.e. detecting and/or quantifying) endotoxin in a sample comprising an antibody; or the herein provided method for the preparation of a sample comprising an antibody have the advantageous effect that they obviate the LER effect in the LAL assay. Thus, one aspect of the invention relates to the use of the herein provided sample preparation method or the herein provided endotoxin determination method for overcoming the LER effect in the determination of bacterial endotoxin in a LAL assay.

More specifically, the herein provided sample preparation method or the herein provided endotoxin determination method have the advantageous effect that these methods render the sample comprising an antibody that exhibits a LER effect reactive to factor C in the LAL enzymatic cascade. Thus, one aspect of the invention relates to the use of the herein provided sample preparation method or the herein provided endotoxin determination method for rendering the sample comprising an antibody exhibiting a LER effect reactive to factor C in the LAL enzymatic cascade.

Herein the term "determining", in particular in the context of "determining bacterial endotoxin" or grammatical variations thereof relates to the detection and/or quantification of endotoxin, preferably to the detection and quantification of endotoxin. In context of the present invention, endotoxin (e.g. *E. coli* endotoxin such as CSE) is preferably determined by a LAL assay.

The term "bacterial endotoxins test" or "bacterial endotoxin test" are used interchangeably herein and relate to a group of tests to detect or quantify endotoxins from Gram-negative bacteria. The BET describes the compendial (i.e. related to a compendium that serves as a standard, such as the European or US Pharmacopeia, or other national or international pharmaceutical standard) LAL assay (limulous amoebocyte lysate assay). Moreover, in context of the invention it is preferred that the pH-value of the sample to be tested during the LAL assay is from 5.7-8.0, preferably 6.0-8.0, more preferably 6.5-7.5.

The term "LAL assay" is commonly known in the art and represents an in vitro endotoxin test for human and animal parenteral drugs, biological products, and medical devices. In particular, the LAL assay is a test to detect and quantify endotoxins from Gram-negative bacteria using the amoebocyte lysate from the horseshoe crab (*Limulus polyphemus* or *Tachypleus tridentatus*). For example, during bacterial cell reproduction, cell division, vegetation dieback and cell lysis, LPS molecules are released from the bacterial cell surface in a rather uncontrolled and unspecific manner. The released LPS represent a potent bacterial toxin and is primarily responsible for the toxic manifestation of severe infections with Gram-negative bacteria and detrimental effects (e.g., high fever, hypotension and irreversible shock) (Rietschel, 1994, FASEB J. 8:217-225). The lipid A component is responsible for this biological activity of LPS. In diluted salt solutions, LPS form macromolecular aggregates (micelles). The formation, size and dynamics of these micelles is correlated to the LPS concentration, various physico-chemical parameters (such as temperature, concentration of the buffer (ionic strength), and pH) as well as the structure of the O-chain, which is the core-oligosaccharide of lipid A (Aurell, 1998, Biochem. Biophys. Res. Comm. 253:119-123). The lipid A moiety of LPS, which is highly conserved among all Gram-negative bacteria, is that part of the LPS molecule that is recognized by the LAL assay, rendering this test a golden standard and a suitable procedure to investigate endotoxin contamination from a broad entity of Gram-negative bacterial sources (Takada (1988) Eur. J. Biochem; 175:573-80).

The principles of the LAL assay are described as follows. In the LAL assay the detection of LPS takes place via gelation of the LAL. This LAL activating activity of LPS is affected by a variety of factors:

- the formation of LPS-LPS aggregates [Akama, 1984, In "Bacterial Endotoxin" (Eds. J. Y. Homma, S. Kanegasaki, O. Lüderitz, T. Shiba and O. Westphal], Publisher Chemie)
- the formation of protein-LPS aggregates, e.g. with human lipoproteins Apo A 1, lysozyme, ribonuclease A or human lgG (Emancipator, 1992, Infect Immun. 60:596-601; Petsch, 1998, Anal. Biochem. 259:42-47)
- the method of extraction of LPS from bacterial cells [Galanos, 1984, In "Bacterial Endotoxin" (Eds. J. Y. Homma, S. Kanegasaki, O. Lüderitz, T. Shiba and O. Westphal), Publisher Chemie]
- the bacteria species; the LAL activating activity within Enterobacteriaceae varies by a factor of 1000 [Niwa, 1984, In "Bacterial Endotoxin" (Eds. J. Y. Homma, S. Kanegasaki, O. Lüderitz, T. Shiba and O. Westphal), Publisher Chemie].

The LAL assay is harmonized among the pharmacopeia in the United States (US), Europe (EP) and Japan (JP). In the harmonized pharmacopeia chapters (USP <85>, Ph. Eur. 2.6.14, and JP 4.01), three techniques for the LAL assay are described:

- gel-clot technique (based on an endotoxin-induced gelling)
- turbidimetric technique (based on the turbidity induced by the gelling)
- chromogenic technique (based on the coloring after splitting of a synthetic peptide-chromogen complex).

These three techniques are in turn applied in 6 different methods:

Method A: gel-clot method, limit test
Method B: gel-clot method, semi-quantitative test
Method C: kinetic turbidimetric method
Method D: kinetic chromogenic method
Method E: chromogenic end-point method
Method F: turbidimetric end-point method Per Ph. Eur./USP/JP these six methods are to be viewed as equivalent.

A prioritized aspect of the present invention relates to the herein provided sample preparation method and the herein provided endotoxin determination method, wherein the kinetic chromogenic method or the kinetic turbidimetric method is used for the determination of bacterial endotoxin in the sample. Most preferably, the kinetic chromogenic method is used in the herein provided sample preparation method and endotoxin determination method. By using this technique endotoxin can be detected photometrically. This technique is an assay to measure the chromophore released from a chromogenic substrate (i.e. a suitable chromogenic peptide) by the reaction of endotoxins with LAL. The kinetic chromogenic assay is a method to measure either the time (onset time) needed to reach a predetermined absorbance of the reaction mixture, or the rate of color development. The test is carried out at the incubation temperature recommended by the lysate manufacturer (which is usually 37±1° C.). For example, for performing the kinetic chromogenic LAL assay, a sample may be mixed with a reagent comprising LAL and a chromogenic substrate (i.e. a suitable chromogenic peptide such as Ac-Ile-Glu-Ala-Arg-pNA and placed in an incubating plate reader. Then, the sample is monitored over time for the appearance of a color (e.g. a yellow color). The time required before the appearance of a color (reaction time) is inversely proportional to the amount of endotoxin present. That is, in the presence of a large amount of endotoxin the reaction occurs rapidly; in the presence of a smaller amount of endotoxin the reaction time is increased. The concentration of endotoxin in unknown samples can be calculated from a standard curve. During the LAL assay, i.e. in step (d) of the herein provided endotoxin determination method, the quantification of endotoxin is preferably carried out via a standard calibration curve, which covers a range of at least two orders of magnitude (in one aspect of the invention 0.005, 0.05, 0.5, 5.0 and 50.0 EU/ml).

For example, during the kinetic chromogenic LAL technique, the following reactions may take place. Gram negative bacterial endotoxin catalyzes the activation of a proenzyme in the LAL. The initial rate of activation is determined by the concentration of endotoxin present. The activated enzyme catalyzes the splitting of p-nitroaniline (pNA) from the colorless substrate Ac-Ile-Glu-Ala-Arg-pNA. The pNA released is measured photometrically, at 405 nm continuously throughout the incubation period. The concentration of endotoxin in a sample is calculated from its reaction time by comparison to the reaction time of solutions containing known amounts of endotoxin standard. For the LAL assay, the kit "*Limulus* Amoebocyte Lysate (LAL) Kinetic-QCL™" from LONZA (Catalog Number: 50-650U, 50-650NV, 50-650H; K50-643L, K50-643U) may be used according to the instructions of the manufacturer. By performing the LAL assay it is envisaged to use the endotoxin, which is comprised in the used kit (e.g. *E. coli* O55:B5 Endotoxin, which is comprised in the kit "*Limulus* Amoebocyte Lysate (LAL) Kinetic-QCL™" from LONZA, Catalog Number: 50-650U, 50-650NV, 50-650H; K50-643L, K50-643U).

In context of the invention it is preferred that the pH-value of the sample to be tested during the LAL assay is from 5.7-9.0. More preferably, the pH-value of the sample to be tested during the LAL assay is from 5.8-8.0, even more preferably from pH 5.8-7.5, even more preferably from pH 5.8-7.0. Most preferably, the pH-value of the sample to be tested during the LAL assay is from 5.8-7.0. For example, the pH-value of the sample to be tested during the LAL assay may be pH 5.7, pH 5.8, pH 5.9, pH 6.0, pH 6.1, pH 6.2, pH 6.3, pH 6.4, pH 6.5, pH 6.6, pH 6.7, pH 6.8, pH 6.9, or pH 7.0. Thus, it is envisaged in context of the invention that before the LAL assay the pH value of the test solution (i.e. a dissolved solid sample or liquid sample) is adjusted to be between pH 5.7-8.0, more preferably between pH 5.8 and pH 7.0. If necessary, the pH value is to be adjusted e.g. by dilution, addition of buffers and/or neutralization.

Several substances (such as β-glucans) interfere with the LAL test to some degree (the obvious exception being water samples). Interference can be inhibition or enhancement of the LAL assay. In particular, interference factors may either enhance or diminish the LPS quantification obtained from the LAL test, and therefore the quantification of the endotoxin. Therefore, if in step (d) of the herein provided endotoxin determination method the recovery of the PPC is not in the acceptable range of 50-200%, the interference factor must be removed. This can be done by sample dilution in step (b) of the herein provided method. In particular, the sample may be diluted with endotoxin-free water or endotoxin-free buffer (preferably with Tris/HCl buffer, pH ~7.0). The lowest sample dilution (highest product concentration) that lacks inhibition/enhancement is called "non-interfering concentration (NIC)". However, during sample dilution, the MVD (Maximum Valid Dilution=maximum possible dilution of a sample in which an endotoxin limit can be determined) may not be exceeded. In particular, based on the test results of the different batches, a sample dilution is chosen that covers all batches (validated sample dilution or sample concentration). Or, in other words, the sample dilution that results in a recovery of 50-200% in the PPC is chosen in step (b) of the herein provided methods. To establish that the treatment chosen effectively eliminates interference without loss of endotoxins (i.e. without showing the LER effect) the "Test for Interfering Factors" can be performed by using a sample that is spiked with a defined concentration of endotoxin (i.e. a PPC).

Accordingly, one aspect of the invention relates to the herein provided endotoxin determination method, wherein a PPC is prepared and tested for endotoxin in step (d) of the herein provided endotoxin determination method. The sample is free of interfering factors if the recovery of the spiked endotoxin control standard amounts to 50-200%.

Due to the fact that the BET per USP/Ph. Eur./JP includes an internal control (PPC) that allows assessment of each test result individually, BET method validation per USP/Ph. Eur./JP is not a prerequisite for correct endotoxins results.

The term "low endotoxin recovery (LER)" or "LER effect" is known in the art and describes endotoxin masking specifically caused by a combination of polysorbate plus either citrate or phosphate (Chen, J. and Williams, K. L., PDA Letter 10, 2013, 14-16). Endotoxin masking may also be caused by any other buffer component or combinations thereof. To identify that a given material (e.g. a buffer or a sample of a therapeutic antibody) exhibits the LER effect, endotoxin contents can be monitored over time, e.g. in an endotoxin hold time study. Endotoxin hold time studies require endotoxin spiking of an undiluted sample and storage of the endotoxin spiked sample over time. For example, the sample may be stored up to several. Preferably, in a hold time study the endotoxin spiked sample is stored for several (e.g. 7 for up to 28) days and at defined time points a LAL assay is performed. Recovery rates that are lower than 50% of the amount of the spiked endotoxin indicate that the sample exhibits a LER effect. If the endotoxin recovery is less than 50% but only occurs in any of the middle time points but not the end time points, the test sample cannot be considered to exhibit a masking effect.

During the last years, FDA has well recognized the LER phenomenon and issued guidance (see Hughes, P., et al., BioPharm. Asia Mar./Apr. 2015, 14-25). These guidance define the acceptable limits of endotoxin recovery in pharmaceutical specimens to range between 50 and 200% once a defined amount of CSE was spiked to the undiluted sample before (e.g. 5.0 EU/ml=100%). In case a sample to be tested exhibits the LER effect, the recovery rate of the spiked endotoxin is below 50% of the total amount of the spiked endotoxin.

In the inventive methods provided herein, the sample comprises an antibody, preferably a monoclonal antibody. Herein the terms "sample", "sample to be tested", "sample comprising an antibody" and "sample comprising an antibody to be tested" are used interchangeably and refer to a certain amount of liquid comprising an antibody that is to be tested for the presence and/or amount of endotoxin. Or, in other words, the terms "sample", "sample to be tested", "sample comprising an antibody" and "sample comprising an antibody to be tested" are used interchangeably herein and relate to a liquid to be tested for the presence and/or amount (preferably for the presence and amount) of endotoxin, wherein said liquid comprises an antibody. Said "sample comprising an antibody to be tested" is preferably a sample of a therapeutic antibody. The term "therapeutic antibody" relates to any antibody preparation that is intended for use in a human being. The antibody (e.g. the therapeutic antibody) is preferably formulated with polysorbate 80 or sodium citrate buffer, more preferably with polysorbate 80 and sodium citrate buffer. Most preferably, the antibody is formulated with an about 25 mM sodium citrate buffer and about 700 mg/L polysorbate 80 and has a pH value of about 6.5. It is preferred in context of the present invention that said antibody (e.g. the therapeutic antibody) is a monoclonal antibody. Most preferably, said antibody (e.g. the therapeutic antibody) is the anti-CD20 antibody rituximab. Thus, in context of the invention, the sample may be a sample of MabThera®/Rituxan®/Zytux®. It is envisaged in context of the invention that the sample to be tested (i.e. the sample comprising an antibody to be tested) shows/exhibits the LER effect.

Herein the term "antibody" is used in the broadest sense and specifically encompasses intact monoclonal antibodies, polyclonal antibodies, multispecific antibodies (e.g., bispecific antibodies) formed from at least two intact antibodies, and antibody fragments, so long as they exhibit the desired biological activity. Also human, humanized, camelized or CDR-grafted antibodies are comprised.

The term "monoclonal antibody" as used herein refers to an antibody obtained from a population of substantially homogeneous antibodies, i.e. the individual antibodies of the population of antibodies are identical except for possible naturally occurring mutations that may be present in minor amounts. Monoclonal antibodies are highly specific, being directed against a single antigenic site. Furthermore, in contrast to polyclonal antibody preparations, which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be constructed as requiring production of the antibody by any particular method. For example, the monoclonal antibodies that are comprised in the sample of the methods of the present invention may be made by the hybridoma method first described by Kohler, G. et al., Nature 256 (1975) 495, or may be made by recombinant DNA methods (see, e.g., U.S. Pat. No. 4,816,567).

The monoclonal antibodies described herein are preferably produced by expression in a host cell, most preferably a Chinese hamster ovary (CHO) cell. For production isolated nucleic acid encoding an the antibody encoding an amino acid sequence comprising the VL and/or an amino acid sequence comprising the VH of the antibody (e.g., the light and/or heavy chains of the antibody) is inserted in one or more vectors (e.g., expression vectors). These are introduced into host cell. The host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. The host cell can be eukaryotic, e.g. a Chinese Hamster Ovary (CHO) cell or lymphoid cell (e.g., Y0, NS0, Sp20 cell).

For recombinant production of antibody, nucleic acid encoding the antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified that may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR– CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

"Antibody fragments" comprise a portion of an intact antibody. The term "antibody fragments" includes antigen-binding portions, i.e., "antigen binding sites" (e.g., fragments, subsequences, complementarity determining regions (CDRs)) that retain capacity to bind an antigen (such as CD20), comprising or alternatively consisting of, for example, (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward; 1989; Nature 341; 544-546), which consists of a VH domain; and (vi) an isolated complementarity determining region (CDR). Antibody fragments or derivatives further comprise F(ab')2, Fv or scFv fragments or single chain antibodies.

Preferably, in the herein provided methods the antibody (i.e. the antibody that is comprised in the sample) is rituximab.

The term "rituximab" (trade names MabThera®, Rituxan®, Zytux®) relates to a chimeric monoclonal antibody against the protein CD20. CD20 is found on the surface of cancerous and normal B-cells. Rituximab destroys B cells and is therefore used, e.g., to treat diseases that are characterized by excessive numbers of B cells, overactive B cells, or dysfunctional B cells. This includes many lymphomas, leukemias, transplant rejection, and autoimmune disorders. For example, rituximab is used in chronic lymphocytic leukemia as a subcutaneous formulation. However, rituximab is usually administered by intravenous infusion. Stem cells in bone marrow do not have the CD20 protein allowing B-cells to repopulate after rituximab treatment. As used herein, the term "rituximab" also encompasses all anti-CD20 antibodies or anti-CD20 antibody fragments that fulfil the requirements necessary for obtaining a marketing authorization in a country or territory selected from the group of countries consisting of the USA, Europe and Japan. Most preferably, the term "rituximab" refers to an antibody having the amino acid sequences of the heavy and light chain as shown in SEQ ID NOs: 1 and 2, respectively. The person skilled in the art readily knows how to obtain a coding nucleic acid sequence from a given amino acid sequence. Thus, with the knowledge of SEQ ID NOs: 1 and 2, coding nucleic acid sequences of rituximab can easily be obtained.

The trade name "NeoRecormon" refers to a pharmaceutical formulation that contains as active ingredient epoetin beta. Epoetin beta is a synthetic version of the naturally-occurring hormone erythropoietin. Erythropoietin is produced by healthy kidneys and stimulates the bone marrow to produce red blood cells, which carry oxygen around the body. Epoetin beta is also used to treat symptomatic anaemia in people with certain types of cancer who are having chemotherapy. One of the side effects of chemotherapy is that it kills healthy blood cells as well as cancer cells. Injections of epoetin increases red blood cell production and helps relieve the symptoms of anaemia. As epoetin increases blood cell production, a larger volume of blood can be taken from people receiving epoetin and this blood can be stored for transfusion during or after the surgery.

In step (d) of the herein provided sample preparation or endotoxin determination method, the sample (i.e. the sample comprising an antibody) is dialyzed against an endotoxin-free aqueous solution, wherein the sample has a pH-value between pH 5.7 and pH 8.0 (preferably between pH 6.0 and 8.0, more preferably between 6.5 and 7.5). In biochemistry, dialysis is a commonly used process of separating molecules in solution by the difference in their rates of diffusion through a semipermeable membrane, such as dialysis tubing. Dialysis is a common laboratory technique that operates on the same principle as medical dialysis. In the context of life science research, the most common application of dialysis is the removal of unwanted small molecules such as salts, reducing agents, or dyes from larger macromolecules such as antibodies. Dialysis is also commonly used for buffer exchange and drug binding studies.

Diffusion is the random, thermal movement of molecules in solution (Brownian motion) that leads to the net movement of molecules from an area of higher concentration to an area of lower concentration until equilibrium is reached. In dialysis, a sample and a buffer solution (called the dialysate) are separated by a semi-permeable membrane that causes differential diffusion patterns, thereby permitting the separation of molecules in both the sample and dialysate. Due to the pore size of the membrane, large molecules in the sample (e.g. antibodies) cannot pass through the membrane, thereby restricting their diffusion from the sample chamber. By contrast, small molecules (e.g. the components of a Na-citrate buffer) will freely diffuse across the membrane and obtain equilibrium across the entire solution volume, thereby changing the overall concentration of these molecules in the sample and dialysate. Once equilibrium is reached, the final concentration of molecules is dependent on the volumes of the solutions involved, and if the equilibrated dialysate is replaced (or exchanged) with fresh dialysate (see procedure below), diffusion will further reduce the concentration of the small molecules in the sample.

For example, the following dialysis procedure for removing Na-citrate buffer from the sample (i.e. from the sample comprising an antibody) may be used:
1. Obtaining and washing a membrane with a molecular weight cut-off of 10 kDa
2. Loading the sample into dialysis tubing, cassette or device
3. Placing the sample into an external chamber with dialysate (with stirring of the buffer)
4. Dialyzing for 24 hours at room temperature; changing water twice during said 24 hours By using the appropriate volume of dialysate and multiple exchanges of the buffer, the concentration of the sodium citrate buffer within the sample can be decreased to negligible levels (i.e. 1-2% of the original content).

The present invention is further described by reference to the following non-limiting figures and examples. In the Figures as well as in the Examples, most of the described experiments are indicated by defined numbers. For example, the designation [rituximab 117] means that the experiment was performed with formulated rituximab and/or with formulated rituximab placebo and has the reference number "117".

Figure 1:
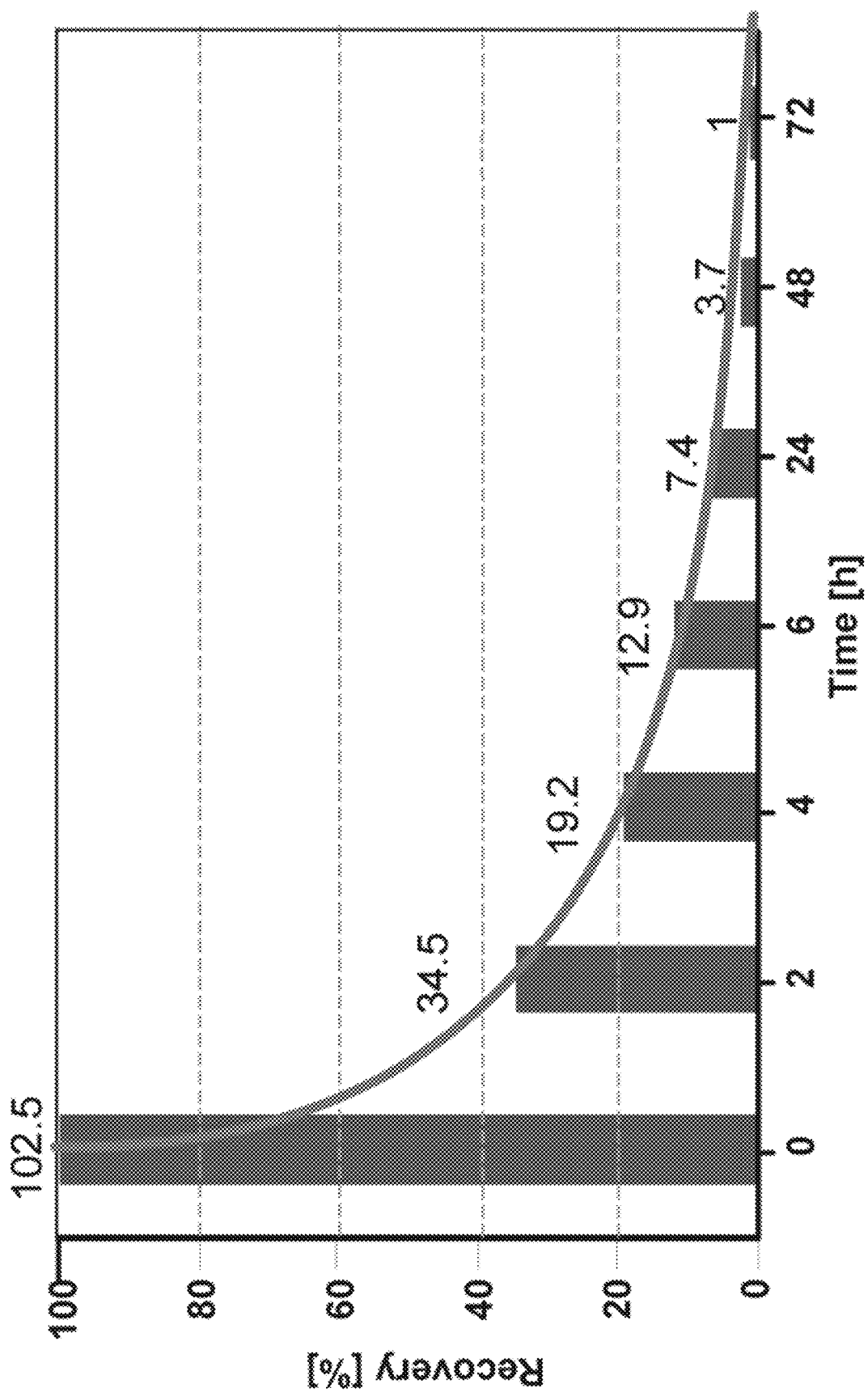
FIG. 1 Time dependency of dialysis of NeoRecormon containing phosphate and polysorbate 20 by using a MWCO of 12-16 kDa. Shown is the weight of the inner dialyzate obtained after the indicated dialysis time at room temperature, lyophilization and weighting. Data on top of gray bars show the average amount of 2 measurements (%).

The following Examples are provided to aid the understanding of the present invention, the true scope of which is set forth in the appended claims. It is understood that modifications can be made in the procedures set forth without departing from the spirit of the invention.

Example 1: Technical Equipment and Reagents

1. Technical Equipment
1.1 Microplate Reader System (Herein Also Designated as "Reader")
   Infinite® 200 PRO, Multimode Microplate Reader; Tecan, Switzerland/Tecan Deutschland GmbH, Germany, P/N: 30050303.
   Magellan V. 7.1 Software
   Costar™ Cell Culture Plates, 96 Wells, Fisher Scientific, P/N: 07-200-89.
1.2 Shaker System and Glass Vials
   Multi Reax; Heidolph, Germany, P/N: 545-10000-00.
   1.5 ml Screw Neck Glass Vials (N8); Macherey-Nagel GmbH & Co. KG, Germany, P/N: 702004 (Qty. of 100).
   N 8 PP screw cap, black, closed top; Macherey-Nagel GmbH & Co. KG, Germany, P/N: 70250 (Qty. of 100).
   4 ml Screw Neck Glass Vials (N13); Macherey-Nagel GmbH & Co. KG, Germany, P/N: 702962 (Qty. of 100).
   N 13 PP screw cap, black, closed top; Macherey-Nagel GmbH & Co. KG, Germany, P/N: 702051 (Qty. of 100).

1.3 Dialysis Equipment
   SpinDIALYZER™, chamber volume 1000 µl; Harvard Apparatus, U.S.A., P/N 740314 (Qty. of 1) and 740306 (Qty. of 5), local distributor: Hugo Sachs Elektronik Harvard Apparatus, GmbH, Germany, P/N SP1 74-0306 (Qty. of 5). Remark: Use of Lot No: 032613.
   The dialyzer is a simple single-sided device for dialysis of biological samples. A broad range of dialyzer sizes are available to accommodate sample volumes ranging from 20 µl to 5 ml. The catalogue Nb. for 1 ml (as used herein) is 74-0314. The MWCO of the membrane ranges from 100 to 300,000 Da. The entire unit is constructed of PTFE, a virtually unreactive material.
   Fast SpinDIALYZER, chamber volume 1000 µl, Harvard Apparatus, U.S.A., P/N 740510 (Qty. of 1) or 740504 (Qty. of 5), Remark: Two-sided membrane system, top plus bottom membrane.
   The dialyzer is a reusable sample chamber made of PTFE for high sample recovery and has been redesigned to provide larger membrane surface areas for an even faster dialysis rate. The Ultra-Fast Dialyzers are of 50 µl to 1500 µl volume and have been used here with 1000 µl. The catalogue Nb. for 1 ml (as used herein) is 74-0412.
   Cellulose acetate membranes, 500 Da MWCO, Harvard Apparatus, U.S.A., P/N: SP1 7425-CA500, local distributor: Hugo Sachs Elektronik Harvard Apparatus GmbH, Germany, P/N: SP1 7425-CA500.
   Cellulose acetate membranes, 10 kDa MWCO, Harvard Apparatus, U.S.A., P/N: SP1 7425-CA10K, local distributor: Hugo Sachs Elektronik Harvard Apparatus GmbH, Germany, P/N: SP1 7425-CA10K.
      Remark: Tested in addition to the 'standard' 500 Da MWCO membranes in LER investigations on Rituximab as well as in the LER experiments on Neo-Recormon®.
   Cellulose acetate membranes, 25 kDa MWCO, Harvard Apparatus, U.S.A., P/N:SP1 7425-CA25K, local distributor: Hugo Sachs Elektronik Harvard Apparatus GmbH, Germany, P/N: SP1 7425-CA25K.
      Remark: Tested in addition to the 'standard' 500 Da MWCO membranes in LER investigations on Rituximab as well as in the LER experiments on Neo-Recormon®.
   Aqua B. Braun, sterile pyrogen-free water, 1 l, B. Braun Melsungen AG, Germany, P/N: 14090586.
   Crystallizing Dishes, 900 ml, OMNILAB, Germany, P/N: 5144008. (Remark: Use for rinsing of dialysis membranes)
   DURAN® Beakers, tall form, 2000 ml, OMNILAB, Germany, P/N: 5013163.
   DURAN® Beakers, tall form, 250 ml, OMNILAB, Germany, P/N: 5013136.
1.4 Routine Laboratory Equipments
   Autoclaving System (Remark: Use for sterilisation of dialyses chambers)
   epT.I.P.S.® LoRetention-Reloads, PCR clean, 0.5-10 µl, Eppendorf, Germany, P/N: 0030072.057
   epT.I.P.S.® LoRetention-Reloads, PCR clean, 2-200 µl, Eppendorf, Germany, P/N: 0030072.022
   epT.I.P.S.® LoRetention-Reloads, PCR clean, 50-1000 µl, Eppendorf, Germany, P/N: 0030072.030
   Stripettes®, Individual, 5 ml, Paper/Plastic Wrap, Fisher Scientific, P/N: 10420201.

2. Reagents
2.1 Kinetic Chromogenic LAL Assays and LAL-Associated Reagents
   Kinetic-QCL™ Kit; Lonza, Switzerland, P/N: 50-650U or 50-650H (i.e. "Lonza kit").
   CHROMO—LAL von Associates of Cape Cod (AAC) Inc., USA, P/N: C0031-5 (i.e. "ACC kit").
   Endotoxin *E. coli* O55:B5 for K-QCL; Lonza, Switzerland, P/N: E50-643.
   Endotoxin *E. coli* O55:B5, 2.5 mg/vial; Lonza, Switzerland, P/N: N185.
   LAL Reagent Water—100 ml; Lonza, Switzerland, P/N: W50-100.
   $MgCl_2$, 10 mM solution for use with LAL, 30 ml vial; Lonza, Switzerland, P/N: S50-641.
   Magnesium chloride hexahydrate for analysis EMSURE® ACS, ISO, Reag. Ph. Eur., 250 g; Merck, Germany, P/N: 1.05833.0250.
   Tris buffer, 50 mM solution for use with LAL, 30 ml vial; Lonza, Switzerland, P/N: S50-642.
2.2 Protein Reagents
   Albumin bovine Fraction V, very low endotoxin, fatty acid free, 25 g; Serva, Germany, P/N: 47299.04.
   Albumin, human serum, fraction V, high purity; 1 g; Merck, Germany, P/N: 126658-1GM.
3. Tested Pharmaceuticals
   For the herein described Examples, Rituximab (which comprises) and NeoRecormon® (which comprises epoetin-beta) were used. In addition, the respective placebos of Rituximab and NeoRecormon® were also applied in the herein described methods.
   The placebo of the respective sample is identical to the sample except for the absence of the active therapeutic ingredient, i.e. rituximab placebo does not contain rituximab but all other component of the formulation.

Example 2: Methods of the Invention for Overcoming the LER Effect

Example 2.1: Protocol for Overcoming the LER Effect

In this Example rituximab and rituximab placebo were used as sample. However, as discussed below, the herein described protocol is useful for overcoming the LER in all typical formulations of pharmaceutical antibodies.
Materials Used for this Example
   Membranes:
   10 kDa cellulose acetate (CA) membranes from Harvard Apparatus, U.S.A., P/N:SP1 7425-CA10K
   Dialyzer:
   FastSpinDIALYZER, chamber volume 1000 µl, Harvard Apparatus, U.S.A., P/N 740510 (Qty. of 1) or 740504 (Qty. of 5)
   Sample Vials:
   1.5 ml Screw Neck Glass Vials (N8); Macherey-Nagel GmbH & Co. KG, Germany, P/N: 702004
   N 8 PP screw cap, black, closed top; Macherey-Nagel GmbH & Co. KG, Germany, P/N: 70250
   Crystallizing Dishes:
   900 ml, Duran, VWR Germany, P/N: 216-1817
   $MgCl_2$ Stock Solution:
   1M $MgCl_2$ dissolved in water (Magnesium chloride hexahydrate for analysis EMSURE® ACS, ISO, Reag. Ph. Eur., 250 g; Merck, Germany, P/N: 1.05833.0250)
   Tris-Buffer, 50 mM solution for use with LAL (i.e. endotoxin-free), 30 ml vial; Lonza, Switzerland, P/N: S50-642
   Samples:
   rituximab placebo and LAL water
Step by Step Protocol:
Step 1: Preparation of the Samples
   1×rituximab placebo 900 µl+100 µl LAL water
   1×rituximab placebo 900 µl+100 µl CSE conc. 50 EU/ml=final conc. 5.0 EU/ml
   1×LAL water 1000 µl
   1×LAL water 900 µl+100 µl CSE conc. 50 EU/ml=final conc. 5.0 EU/ml
   Shake the samples 60 min at RT (room temperature) [i.e. in a Heidolph Multi Reax shaker, high speed (2,037 rpm)],
Step 2: Washing of Dialysis Membrane
   Use ten 10 kDa cellulose acetate (CA) membranes and put them into the crystallizing dish with 300 ml Aqua Braun (i.e. distilled water of the manufacturer B. Braun, Melsungen)
   Shake them for 1 h (Shaker SG 20. IDL GmbH, Germany or equivalent, 50 to 300 rpm, preferably 100 rpm)
   Transfer the membranes into an new crystallizing dish with fresh Aqua Braun (also 300 ml)
   Shake them for 1 h (Shaker SG 20. IDL GmbH, Germany or equivalent, 50 to 300 rpm, preferably 100 rpm)
Step 3: Addition of $MgCl_2$ to a Final $MgCl_2$ Concentration of about 50 mM $MgCl_2$
   Add 50 µl of the 1M $MgCl_2$ stock solution to the samples of step 1
   Shake them 1 min. [i.e. in a Heidolph Multi Reax shaker, high speed (2,037 rpm) at room temperature]
   Incubate the samples for 60 min at room temperature
   Shake them 1 min. [i.e. in a Heidolph Multi Reax shaker, high speed (2,037 rpm) at room temperature]
Step 4: Dilution
   Take one of the samples of step 3 and dilute it 1:10 with buffer, pH ~7 (i.e. 50 mM Tris/HCl buffer pH ~7)
   895 µl 50 mM Tris-buffer+105 µl sample
   Perform it twice for a repeat determination (i.e. determination in duplicates):
   2×rituximab placebo 1:10 with Tris-buffer
   2×rituximab placebo 5.0 EU/ml 1:10 with Tris-buffer
   2×LAL water 1:10 with Tris-buffer
   2×LAL water 5.0 EU/ml 1:10 with Tris-buffer
Step 5: Dialysis
   Shake all diluted samples for 1 min [i.e. in a Heidolph Multi Reax shaker, high speed (2,037 rpm) at room temperature],
   Transfer into the FastSpinDIALYZER
   Put one dialyzer per beaker (i.e. DURAN® baker, tall form, 2000 ml, OMNILAB, Germany, P/N: 5013163) on a magnetic stirrer plate. Adjust the frequency of the stirrer to be high (i.e. "fast spin"). A high frequency of the stirrer means 50-300 rpm, preferably 200-300 rpm. The stirrer is a heat-sterilized (4 hours at 250° C.) magnetic stirrer having a length of about 40 mm and a diameter of about 14 mm.
   Fill the beaker with 200 ml Aqua Braun
   Dialyze 24 h and exchange the Aqua Braun after 2 h and 4 h at room temperature (21±2° C.)
   After dialysis transfer the sample into new 1.5 ml screw vials Step 6: Shaking
Shake the samples for 20 min. [i.e. in a Heidolph Multi Reax shaker, high speed (2,037 rpm) at room temperature]

Step 7: Preparation of the LER Positive Control (i.e. the Positive LER Control) and of Further Water Controls
Prepare the LER positive control 1 h before the dialysis ends
1. rituximab placebo 900 µl+100 µl LAL water
2. rituximab placebo 900 µl+100 µl CSE conc. 50 EU/ml=final conc. 5.0 EU/ml
3. LAL water 1000 µl
4. LAL water 900 µl+100 µl CSE conc. 50 EU/ml=final conc. 5.0 EU/ml
Shake 1 h [i.e. in a Heidolph Multi Reax shaker, high speed (2,037 rpm) at room temperature]
Dilute samples 1:10 (sample:LAL water) with LAL water
Shake [i.e. in a Heidolph Multi Reax shaker, high speed (2,037 rpm) at room temperature] for 1 min Step 8: LAL Assay
Prepare the standard and start the LAL assay according to the instructions of the manufacturer (Kinetic-QCL™ assay; Lonza)

Results and Discussion

Figure 3A:
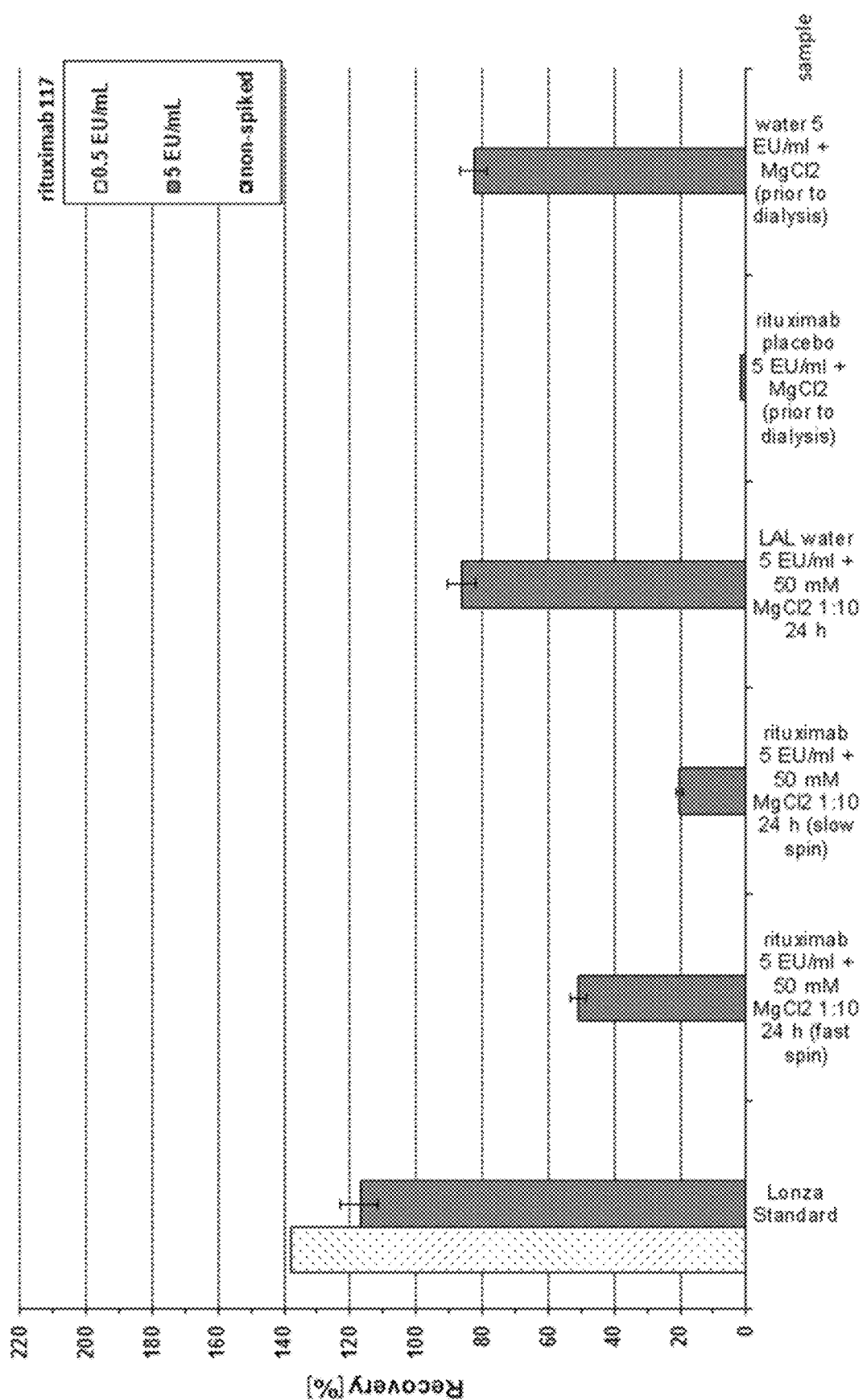
FIG. 3: [Rituximab 115] and [Rituximab 117] Recovery rates (%) obtained by performing the protocol for overcoming the LER effect as described in Example 2.1 by using (A) Rituximab and (B) Rituximab placebo as sample. In the Figures "fast spin" and "slow spin" means the frequency of the stirrer (i.e. "fast spin" means that the frequency of the stirrer is high). This exemplary protocol is also useful for routine quality control of other samples, preferably for specimen containing sodium citrate buffer and polysorbate 80 as detergent.

As can be seen in FIG. 3(A) (i.e. [rituximab 117]) and 3(B) (i.e. [rituximab 115]) the above described method is able to overcome the LER effect. In addition, by using this method, the LER effect can be overcome in rituximab as well as in rituximab placebo. This indicates that the above described protocol in not dependent on a formulation comprising a particular monoclonal antibody but can be used to obviate the LER effect in every formulation comprising polysorbate 80 and a chelating buffer (such as sodium citrate). This formulation is typical for antibodies, in particular monoclonal antibodies. Thus, the above described method is expected to be useful to overcome the LER effect in every antibody formulation.

It has been found that $Mg^{2+}$ is the divalent cation of choice to restore LAL reactivity in formulations containing chelating buffers (such as sodium citrate) and showing the LER effect.

In order to remove the chelating buffer (e.g. the Sodium citrate buffer), a second step (after addition of $Mg^{2+}$) is to perform dialysis. The spinDIALYZER™ of Harvard is the preferred equipment for the dialysis.

The detergent (e.g. polysorbate 80) represents the second reason for the LER effect. In general, the presence of detergents (such as polysorbate 80) in a biological sample leads to micelle formation in case the critical micellar concentration (CMC) of the detergent (usually in the µM range) is reached. Micelles may inhibit the LPS-mediated activation of factor C, a serine protease representing the first enzyme in the LAL-cascade reaction (Nakamura (1988a) J. Biochem. 103: 370-374). In monoclonal antibody preparations, the undiluted sample is usually above the CMC in order to obtain a functional solubilisation of the antibody. In the products which were investigated here, the CMC of the detergents indeed exceeded their CMC (polysorbate 80: 700 mg/l (50 fold excess)) leading to the assumption that polysorbate 80 is present in form of micelles. In the above described protocol the concentration of the detergent is reduced by dilution so that the concentration of the detergent is near/drops below the CMC value (polysorbate 80: 14 mg/l or 10.6 µM). Dilution of the detergent to near-CMC concentrations may eliminate the micellar compartmentalization, and therefore, render the CSE molecules spiked accessible for the LAL enzymes.

Accordingly, the problem of the LER effect, (e.g. in the event sodium citrate and polysorbate 80 are used for the formulation of a pharmaceutical product) can now be considered as being solved. In conclusion, herewith provided is a safe, robust and reproducible testing method for pharmaceutical products.

In summary, in rituximab and rituximab placebo the above described protocol surprisingly overcomes the LER effect. By contrast, the same protocol could not reveal satisfactory results for NeoRecormon® (which does not comprise an antibody but epoetin-beta) indicating that the herein provided methods are particularly useful for antibody formulations, preferably for formulations with monoclonal antibodies, citrate buffer and polysorbate 80.

Example 2.2: Modified Protocol (1) for Overcoming the LER Effect

In this Example a modified protocol has been used which nevertheless overcomes the LER effect. The most important changes compared to Example 2.1 are as follows:
1. In Example 2.2 the Spin Dialyzer has been used. In contrast, in Example 2.1 the FastSpinDIALYZER is used which has more efficient dialysis chambers and increases the efficiency of the dialysis (the membranes are on both sides of the cylinder).
2. In Example 2.2 the MWCO of the dialysis membrane is 500 Da. In contrast, in Example 2.1 the MWCO of the dialysis membrane is 10 kDa.
3. In Example 2.2 the dilution is 1:10 with endotoxin-free water. In contrast, in Example 2.1 the dilution 1:10 with Tris-buffer pH~7 (i.e. Tris/HCL buffer pH~7). By diluting the sample with endotoxin-free water at a ratio of 1:10 the pH value of the sample is adjusted to about pH 6.0.
4. In Example 2.2 the dialysis time is 4 h. In contrast, in Example 2.1 the dialysis time is 24 h.

In this Example rituximab and rituximab placebo were used as sample. However, for the same reasons as discussed with respect to Example 2.1, this protocol is useful for overcoming the LER in all typical antibody formulations.

In particular, the protocol used in Example 2.2 is detailed as follows.

Protocol Overview

Step 1: "Setting up the LER effect" (see also below "LER positive control"):
Rituximab and rituximab placebo samples were spiked with 5 EU/ml or 0.5 EU/ml (CSE; Lonza, *E. coli* 0055:B5) and the mixture was shaken for 60 min at room temperature at maximum speed [Shaker: Heidolph Multi Reax, high speed (2,037 rpm)] to obtain a "positive LER-effect" sample.

Step 2: Adding $MgCl_2$: Before dialysis, add 2 M $MgCl_2$ stock solution so that the final conc. is about 50 mM $MgCl_2$; 1 min shaking as in step 1.

Step 3: 1:10 Dilution [one sample without dilution (undiluted) as reference]; shaking for 1 min as in step 1.

Step 4: Dialysis for 4 h using a 500 Da membrane (30 min pre-incubated with 0.2% BSA; optionally but not mandatory), exchange of water after 2 h once. Transferring of the solution from the dialysis chamber into a glass vial and shaking as in step 1 for 20 min at RT (room temperature, i.e. 21±2° C.).

Step 5: kinetic LAL-assay measurement.

Detailed Protocol

Step 1: Preparation of the Samples
Preparation antibody solution (rituximab) for 50 mM $MgCl_2$: Fill 1 tube with 877.5 µl rituximab+97.5 µl CSE (stock solution of 50 (5) EU CSE/ml→5 (0.5) EU/ml final concentration).

Unspiked control: 877.5 µl rituximab placebo+97.5 µl water

Unspiked water control: 975 µl water (for blank subtraction)

used vials: clear flat bottom small opening 1.5 ml Macherey & Nagel, Ref. Nr. 70213

1 h shaking on Heidolph Multi Reax, high speed (2,037 rpm) at room temperature.

Step 2: Addition of $MgCl_2$ to a Final Concentration of 50 mM $MgCl_2$

Stock solution 1M $MgCl_2.6H_2O$: add 50 µl of a 1M $MgCl_2$-stock solution to the spiked sample as well as to the unspiked sample (blank).

Step 3: Dilution

Sample rituximab with 50 mM $MgCl_2$: prepare a 1:10 dilution by adding 900 µl endotoxin-free water (i.e. LAL water)+100 µl sample Water control is treated the same with endotoxin-free water (i.e. LAL water) instead of rituximab: dilute 1:10

Step 4: Dialysis 1 min shaking before dialysis [i.e. in a Heidolph Multi Reax shaker, high speed (2,037 rpm) at room temperature].

Put samples into the 1 ml dialyzer chambers (Harvard Spin Dialyzer) to which a membrane with MWCO 500 Da (optionally, 30 min pre-incubated with 0.2% BSA) is fixed.

Dialyze 4 h against 1 l Aqua Braun (i.e. sterile, pyrogen free water; as supplied by B. Braun, Melsungen) at 24° C.; change water after 2 h. Changing water has been tempered also to 24° C.

The Spin Dialyzers are distributed (depending on the number of dialysis chambers) over multiple 2 l beakers filled with 1 l Aqua Braun under stirring (magnetic Teflon stirrer).

There are at most 5 Dialyzer in one 2 l beaker.

Step 5: Preparation of the LER Positive Control

Also in this Example a LER positive control is used in the LAL assay. This LER positive control can be prepared at any time, provided that it is ready if the LAL assay starts. Advantageously, the LER positive control is prepared 1 h before the end of 4 h dialysis, so that all samples are ready for testing at the same time. For preparing the LER positive control the following protocol is used:

rituximab 900 µl+100 µl CSE→final conc. CSE: 5.0 EU/ml.

Shaking in a Heidolph Multi Reax, high speed (2,037 rpm) at RT for 1 h. Only under these conditions the max. LER effect (<1% recovery rate) will be obtained.

In parallel prepare the following blanks:

Water with 5.0 EU/ml CSE

Water with 5.0 EU/ml CSE; diluted 1:10 (0.5 EU/ml).

Step 6: LAL Assay

Start test after all samples are prepared.

From all samples two aliquots of 100 µl are used for repeat determination (2×, i.e. determination in duplicates) in a plate which is incubated 10 min at 37° C. in the Tecan Reader.

Add 100 µl LAL Reagent (Kinetic-QCL™ Assay; Lonza) to each sample in a well-defined sequence (according to the read-out of the machine).

Figure 4A:
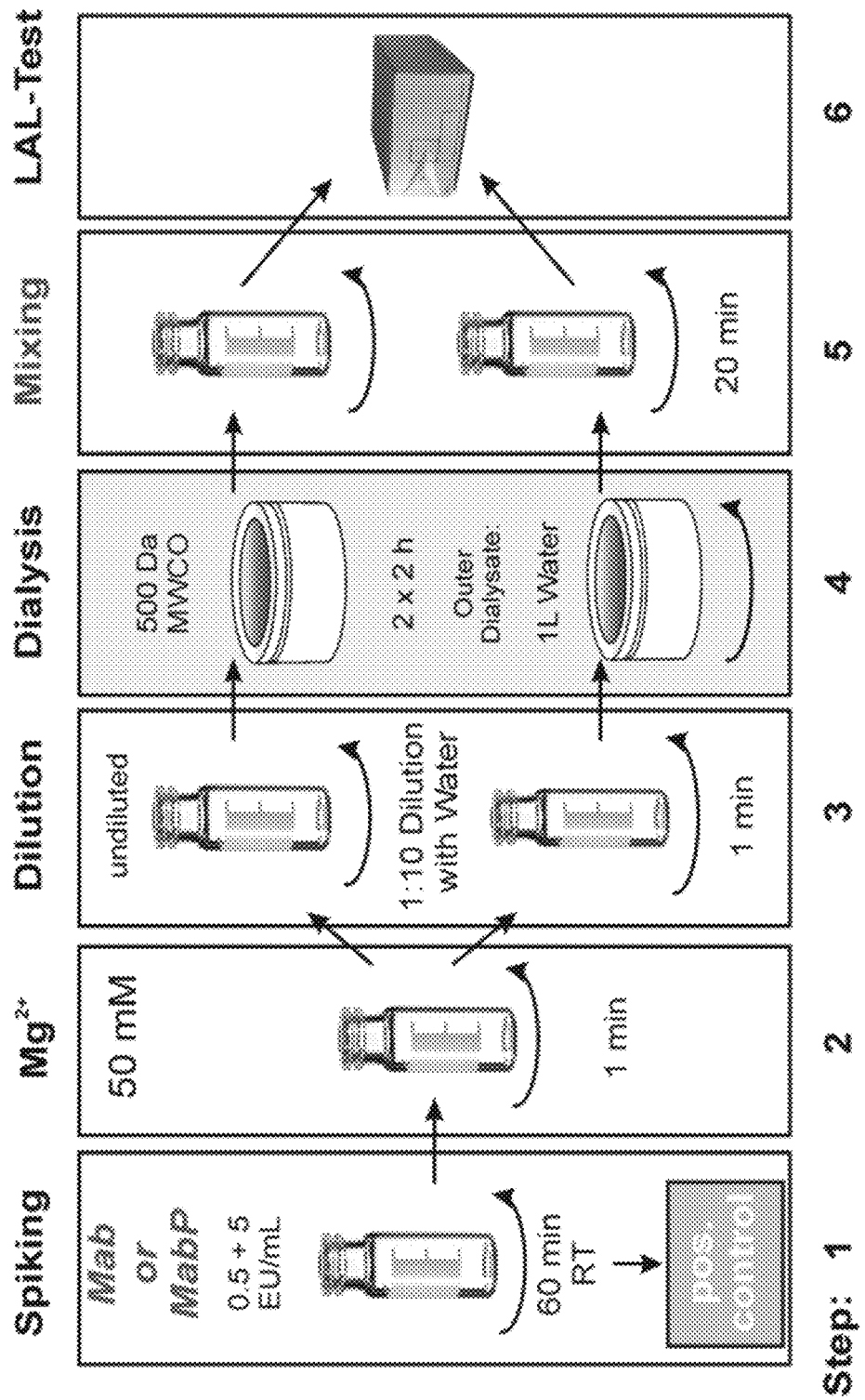
FIG. 4: Schematic representation of a modified protocol for overcoming the LER effect and recovery rates obtained by performing said protocol. (A) Schematic representation of a protocol according to the invention for overcoming the LER effect (e.g. in rituximab and rituximab placebo). The detailed protocol is described in Example 2.2. This exemplary protocol is also useful for routine quality control of other samples, preferably for specimen containing sodium citrate buffer and polysorbate 80 as detergent. (B) [rituximab 046] Recovery rate (%) of rituximab and rituximab placebo obtained by the LER assay after performing the protocol according to FIG. 4(A). For further details, see protocol described in Example 2.2.

Results and Discussion:

The protocol described in Example 2.1 resulted in best reproducible recovery rates (also with respect to the water controls). However, the protocol described in Example 2.2 resulted in a good CSE recovery-rate ranging from 50 to 95% for both CSE concentrations spiked (see FIG. 4(B) [rituximab 046]). Therefore, it can be concluded that the protocol used in Example 2.2 represents a functional equivalent to the protocol described in Example 2.1.

Reference Example 1: Time Dependency of the LER Effect

In the prior art it is assumed that the LER effect appears immediately after spiking of the sample with a defined amount of CSE (C. Platco, 2014, "Low lipopolysaccharide recovery versus low endotoxin recovery in common biological product matrices". American Pharmaceutical Review, Sep. 1, 2014, pp. 1-6). Therefore, first the samples were shaked after LPS spiking for a rather short time of about 2-10 min at room temperature. However, this kind of spiking turned out to be inefficient and some experiments indicated that the masking effect of the material spiked has not yet reached its maximum during this short time interval (<10 min). It was found that the mechanism of spiking is one of the fundamental processes in analyzing the LER effect in a correct way (see, e.g., FIG. 13 [rituximab 027]). According to these data, the LER effect is a kinetic phenomenon, which requires time to mask the CSE molecules e.g. by penetrating into the micelles of the formulation mixture. Thus, shaking for 2-10 min prior to the next step for analyzing the LER effect, as it represents the routine practice, are inappropriate and cannot be considered to be representative for the LER effect, because the conditions for its formation has not yet been reached. Therefore, an internal standard to test the "positive LER effect" (defined to be present in case the recovery rate of 0% by the LAL test has been reached) was included in the experiments. By performing a kinetic study on the LER effect in rituximab, the positive LER effect was demonstrated to need ≥60 min incubation time.

Figure 13:
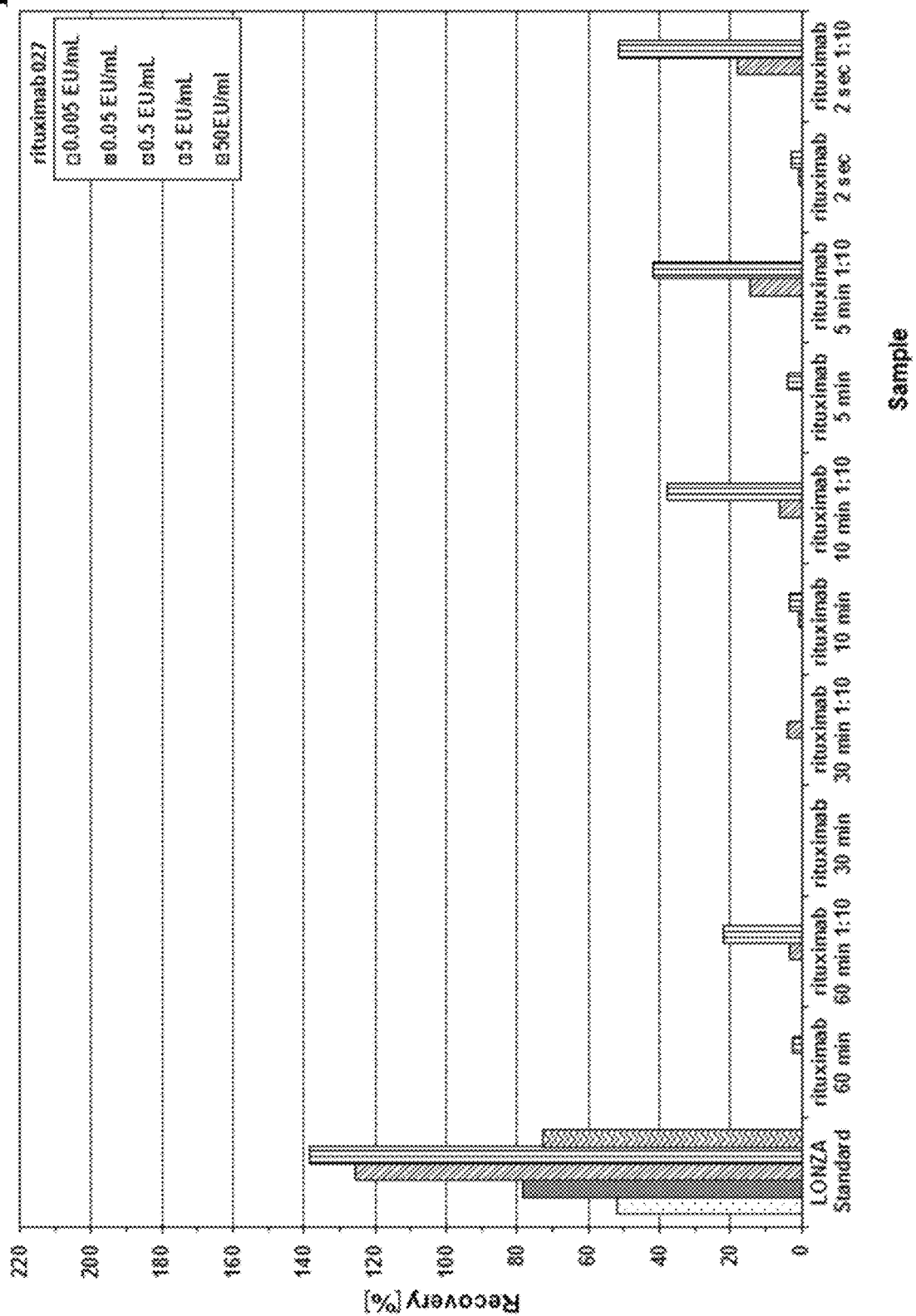
FIG. 13: Time dependency of the LER effect. The Figure shows recovery rates (%) obtained by performing spiking and the LAL assay as described in Reference Example 1 by using Rituximab as sample [rituximab 027]. The shaking time after spiking (i.e. 2 sec to 60 min) is indicated.

In particular, it was analyzed how long shaking has to be carried out [max. frequency (i.e. vortexing) in a Heidolph Multi Reax shaker, high speed (2,037 rpm) at room temperature in (21° C.±2° C.) a 1.5 ml clear glass, crimp neck, flat bottom vessel], in order to achieve the maximum LER effect. Therefore, rituximab samples were spiked with CSE in a vial, so as to obtain 0.5 and 5.0 EU/ml (vials by Macherey-Nagel, 1.5 ml). After spiking, the samples were shaked for 60 min, 30 min, 10 min, 5 min, or 2 sec, respectively. Afterwards, 1:10 dilutions were prepared by mixing 900 µl endotoxin-free water (i.e. LAL water) with 100 µl sample. After dilution, the samples were again shaked for 1 min. Subsequently, the samples were tested in the LAL assay in duplicates. In particular, 100 µl of each sample was applied onto a plate and incubated in the reader for 10 min at 37° C. Then, 100 µl chromogen was added to each sample and the measurement was carried out. In this experiment, all solutions had room temperature. As can be seen in FIG. 13 [rituximab 027], the LER effect is lower (i.e. the recovery rate is higher) if the sample is diluted at a ratio of 1:10 as compared to the corresponding undiluted sample. In addition, after 2 sec shaking the recovery values for the diluted samples with 5.0 EU/ml endotoxin were still at approximately 50%. However, increasing shaking (i.e. vortexing) time results in a constant decrease of the recovery rate (with exception of the 30-min value), see FIG. 13 [rituximab 027]. In contrast, the undiluted samples show the maximum LER effect already after 2 sec. However, also the diluted samples showed a significant LER effect in the samples which have been shaked (i.e. vortexed) for 60 min.

From this result it was concluded that spiking needs time to mask the LPS molecules into the detergent micelles. The "positive LER effect" is complete when about 100% masking or <0.5% recovery rates of CSE are obtained. This process requires a minimum of 1 h during shaking at room temperature [e.g., shaker: Heidolph Multi Reax, high speed (2,037 rpm) for 1 h at room temperature in a 1.5 to 5 ml clear glass, crimp neck, flat bottom] or alternatively storage at 4° C. for a longer time period >24 h. The resulting "positive LER control" is shown in all graphical plots as one bar in the graphical presentations at the right side of the diagram.

Figure 5:
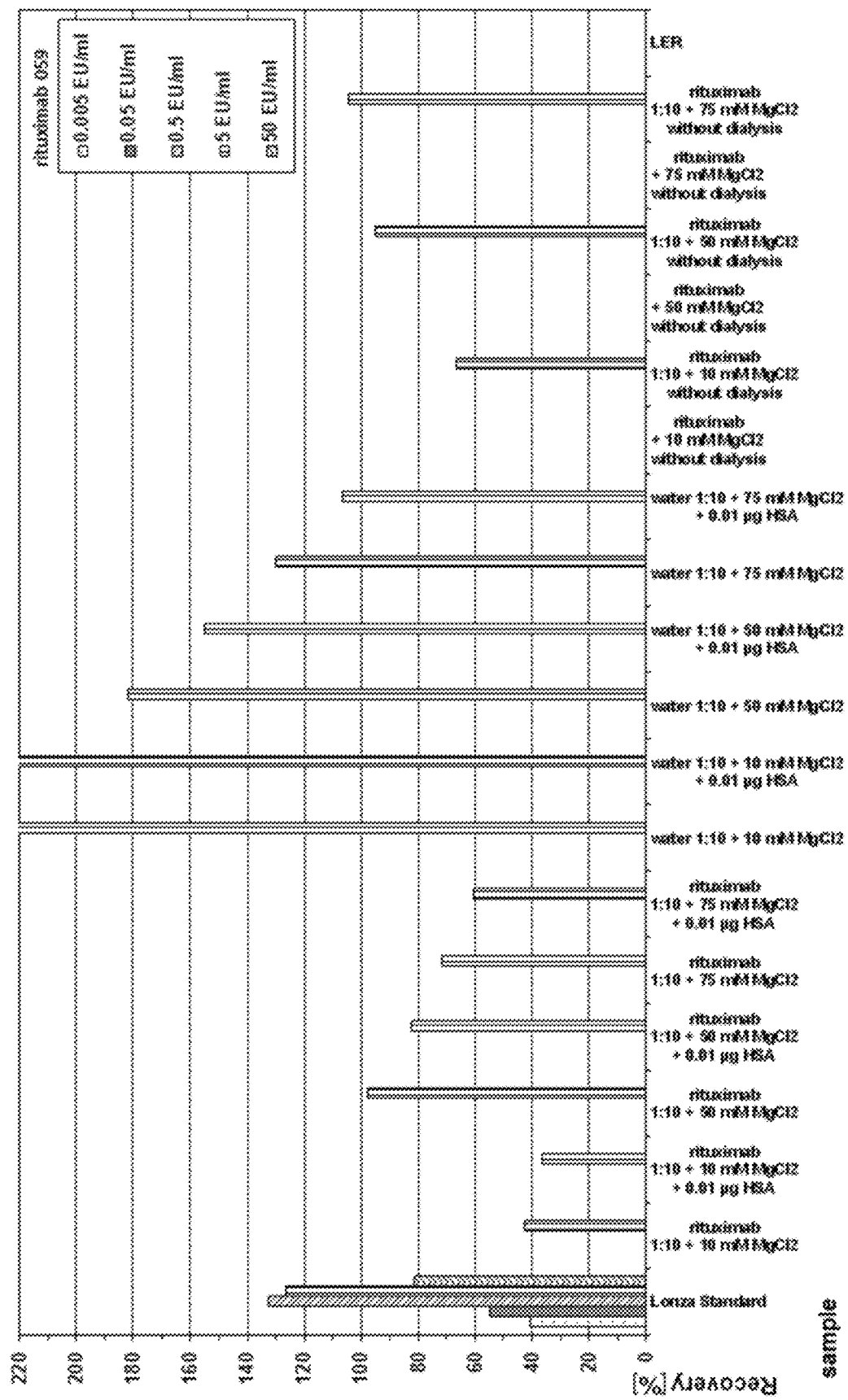
FIG. 5: [Rituximab 059] Recovery rates (%) obtained by performing the protocol as described in Reference Example 2 by using Rituximab as sample.

Reference Example 2: Influence of Human Serum Albumin (HAS) and Different $MgCl_2$ Concentrations on the Recovery Rate In order to determine the effect of HSA and different $MgCl_2$ concentrations on the recovery rate of endotoxin spiked rituximab samples, the following experiment has been performed. In addition, in this experiment the influence of dialysis on the recovery rate has been analyzed. More specifically, rituximab spiked samples were shaken for 60 min in order to obtain the "positive LER effect". Prior to the dialysis, 10-75 mM $MgCl_2$ were added, subsequently, a dilution was performed. No BSA-blocked membrane was used. After the dialysis, 0.01 μg/ml HSA is either added or not added. Subsequently, shaking for 20 min is performed. In addition, some samples were not dialyzed at all. In particular, the different samples which have been tested in the LAL assay are shown in FIG. 5 (i.e. [rituximab 059]). In this experiment, the LER effect could be overcome in some samples without dialysis. However, further experiments demonstrated that without dialysis the LER effect cannot reproducibly been overcome. Or, in other words, without dialysis, the LER effect is sometimes overcome and sometimes not. Thus, dialyzing the samples results in a more robust method for overcoming the LER effect.

The samples have been prepared in a 1.5 ml screw neck vial by Macherey-Nagel.
Step 1: Preparation of the Samples
  Preparation of spiked rituximab for 10 mM $MgCl_2$: 897 μl rituximab+99.8 μl CSE so that 5.0 EU/ml are obtained
  Preparation of spiked rituximab for 50 mM $MgCl_2$: 889 μl rituximab+98.8 μl CSE so that 5.0 EU/ml are obtained
  Preparation of spiked rituximab for 75 mM $MgCl_2$: 883 μl rituximab+98.1 μl CSE so that 5.0 EU/ml are obtained
  Preparation of spiked water for 10 mM $MgCl_2$: 897 μl water+99.8 μl CSE so that 5.0 EU/ml are obtained
  Preparation of spiked water for 50 mM $MgCl_2$: 889 μl water+98.8 μl CSE so that 5.0 EU/ml are obtained
  Preparation of spiked water for 75 mM $MgCl_2$: 883 μl water+98.1 μl CSE so that 5.0 EU/ml are obtained
  Shake for 60 min [Heidolph Multi Reax shaker, high speed (2,037 rpm) at room temperature]
Step 2: Addition of $MgCl_2$
  A 4 M $MgCl_2$ stock solution (i.e. 511.437 mg $MgCl_2.6H2O$ in 0.629 ml water) was used.
    For 10 mM $MgCl_2$ 2.5 μl of the 4 M solution are added to the spiked sample.
    For 50 mM $MgCl_2$ 12.5 μl of the 4 M solution are added to the spiked sample.
    For 75 mM $MgCl_2$ 19 μl of the 4 M solution are added to the spiked sample.
  Shake for 1 min [Heidolph Multi Reax shaker, high speed (2,037 rpm) at room temperature]
Step 3: Dilution
  Dilutions at a ratio of 1:10 were prepared as follows:
  Preparation rituximab 1:10: always 900 μl LAL water+100 μl sample
  The water was not diluted 1:10 since there are not enough dialyzers available.
  Shake for 1 min [Heidolph Multi Reax shaker, high speed (2,037 rpm) at room temperature]
Step 4: Dialysis
  The samples were put into a 1 mL dialyzer. A 500 Da membrane. However, the membrane was washed in LAL water.
  Dialysis was performed against 1 L Aqua Braun at 24° C. for 4 h, and after 2 h the water was changed. The new water also had a temperature of 24° C.
  The dialyzers were located in three 2 L beakers and rotated since there was a long stirrer (i.e. stir bar) in each beaker.
  There are always 4 dialyzers in each beaker.
Step 5: Addition of HSA after Dialysis
  After the dialysis, the samples were portioned. For the preparation of HSA-samples 396 μl of each sample were added to a separate vial. For the preparation of samples without HSA 400 μl were added to a separate vial.
  To obtain a HSA concentration of 0.01 μg/ml, 4 μl of a 1 μg/ml solution were added to the 396 μl samples
  The HSA stock solution was newly prepared.
  Shake for 20 min [Heidolph Multi Reax shaker, high speed (2,037 rpm) at room temperature]
Step 6: Preparation of the LER Positive Control
  The LER positive control is prepared 1 h before the end of the 4 h dialysis so that it is ready at the same time as the other samples.
  rituximab 900 μl+100 μl CSE of different CSE stock solutions so that 5.0 EU/ml are obtained]
  shaken at room temperature for 1 h [Heidolph Multi Reax shaker, high speed (2,037 rpm)]
Step 7: LAL Assay
  100 μl of each samples were applied onto a plate in double determination
  Incubation in the reader at 37° C. for 10 min.
  100 μl chromogen were applied to each sample.
  Starting the measurement in the reader.
Results and Discussion:
The results are shown in FIG. 5 [rituximab 059]. This experiment demonstrates that HSA treatment reduces the recovery rate and is therefore less useful in context of the herein provided methods. In addition, the results show that BSA treatment of the dialysis membrane is not necessary to obtain satisfactory recovery rates. In addition, this experiment also demonstrates that 50 mM $MgCl_2$ is the optimum value for recovery, 10 and 75 mM $MgCl_2$ result in lower recovery. However, also with 75 mM $MgCl_2$ a satisfactory recovery rate was obtained. Moreover, this experiment shows that addition of $MgCl_2$ leads to a recovery within a satisfactory range (70-100%) even without dialysis. However, as mentioned above, without dialysis the LER effect cannot reproducibly been overcome. Thus, dialyzing the samples results in a more robust method for overcoming the LER effect. It is indicated that in the experiment [rituximab 059] the water control values were high (part of the values >220%). The LER positive control is satisfactory; i.e. 0% recovery.

Reference Example 3: 4 Hours Incubation Time after Addition of $MgCl_2$

In this experiment rituximab samples were shaken for 60 min in order to achieve the "positive LER effect". After addition of $MgCl_2$ the undiluted samples were incubated for 4 h at room temperature). After this incubation, the samples were shaked for 2 min. The different samples which have been tested in the LAL assay are shown in FIG. 5(B) [rituximab 061].

The samples have been prepared in a 1.5 ml screw neck vial by Macherey-Nagel.

Step 1: Preparation of the Samples
   Preparation of spiked rituximab/water for 10 mM $MgCl_2$: 897 µl rituximab/water+99.8 µl CSE so that 5.0 EU/ml are obtained
   Preparation of spiked rituximab/water for 50 mM $MgCl_2$: 889 µl rituximab/water+98.8 µl CSE so that 5.0 EU/ml are obtained
   Preparation of spiked rituximab/water for 75 mM $MgCl_2$: 883 µl rituximab/water+98.1 µl CSE so that 5.0 EU/ml are obtained
   Preparation of spiked rituximab/water for 100 mM $MgCl_2$: 877 µl rituximab/water+97.5 µl CSE so that 5.0 EU/ml are obtained
   Preparation of spiked rituximab/water for 150 mM $MgCl_2$: 866 µl rituximab/water+96.3 µl CSE so that 5.0 EU/ml are obtained
   Shake for 60 min [Heidolph Multi Reax shaker, high speed (2,037 rpm) at room temperature]

Step 2: Addition of $MgCl_2$
   A 4 M $MgCl_2$ stock solution (i.e. 534.661 mg $MgCl_2.6H_2O$ in 0.657 ml water) was used.
   For 10 mM $MgCl_2$ 2.5 µl of the 4M solution are added to the spiked sample.
   For 50 mM $MgCl_2$ 12.5 µl of the 4M solution are added to the spiked sample.
   For 75 mM $MgCl_2$ 19 µl of the 4M solution are added to the spiked sample.
   For 100 mM $MgCl_2$ 25 µl of the 4M solution are added to the spiked sample.
   For 150 mM $MgCl_2$ 37 µl of the 4M solution are added to the spiked sample.
   Shake for 1 min [high speed (2,037 rpm) at room temperature]

Step 3: Dilution
   Dilutions at a ratio of 1:10 were prepared: 900 µl LAL water+100 µl sample (i.e. rituximab sample or water sample)
   Shake for 1 min [Heidolph Multi Reax shaker, high speed (2,037 rpm) at room temperature]

Step 4: Preparation of the LER Positive Control
   rituximab 900 µl+100 µl CSE so that 5.0 EU/ml are obtained
   Another LER positive control was prepared by mixing 900 µl rituximab+100 µl CSE so that 5.0 EU/ml are obtained; and subsequently diluting the sample 1:10 with endotoxin-free water Step 5: Shaking
   All samples as well as the LER positive controls were shaken at room temperature for 1 h [Heidolph Multi Reax shaker, high speed (2,037 rpm)]

Step 6: LAL Assay
   100 µl of each sample were applied onto a plate in double determination
   Incubation in the reader at 37° C. for 10 min.
   100 µl chromogen was applied to each sample.
   Starting the measurement in the reader.

Figure 6:
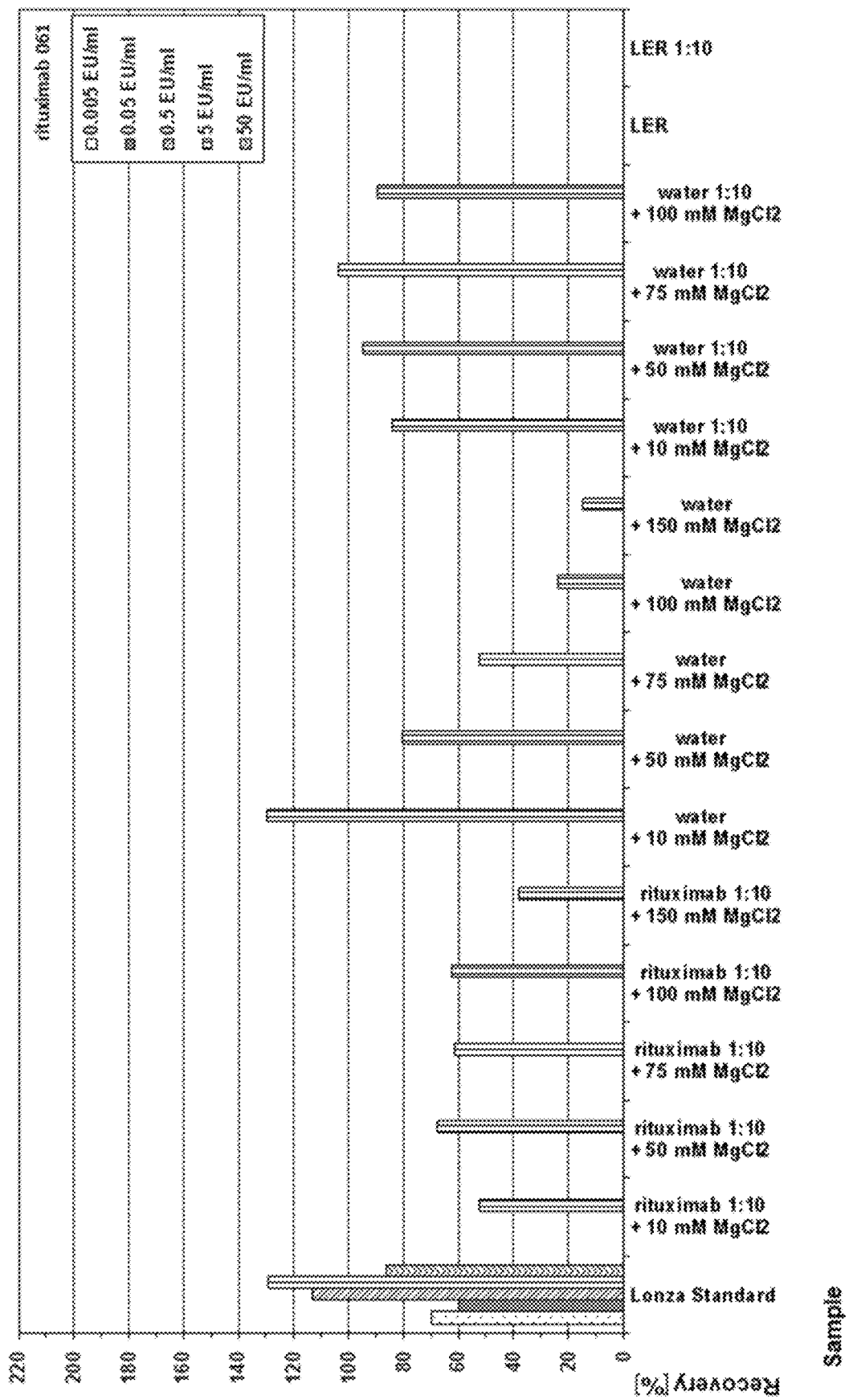
FIG. 6: Recovery rates (%) obtained by performing the protocol as described in Reference Example 3 by using Rituximab as sample. Recovery rates obtained by performing the protocol as described in Reference Example 2.2 [rituximab 061].

Results and Discussion:
The result of this experiment is shown in FIG. 6(B) (i.e. [rituximab 061]). This Figure demonstrates again that 50 mM $MgCl_2$ is the reproducible optimum value for CSE recovery; 10, 75 and 150 mM show slightly inferior results. When an incubation time after addition of $MgCl_2$ was performed, the undiluted rituximab samples did not lead to a CSE recovery at all, see FIG. 6(B) (i.e. [rituximab 061]). However, the 1:10 dilutions resulted in approximately 50-60% recovery (in particular when 10, 50, 75 or 100 mM $MgCl_2$ was added). The water control values as well as the LER positive control were satisfactory. In this experiment no dialysis was performed. However, several experiments showed that dialysis is necessary for reproducibly overcoming the LER effect.

Figure 7B:
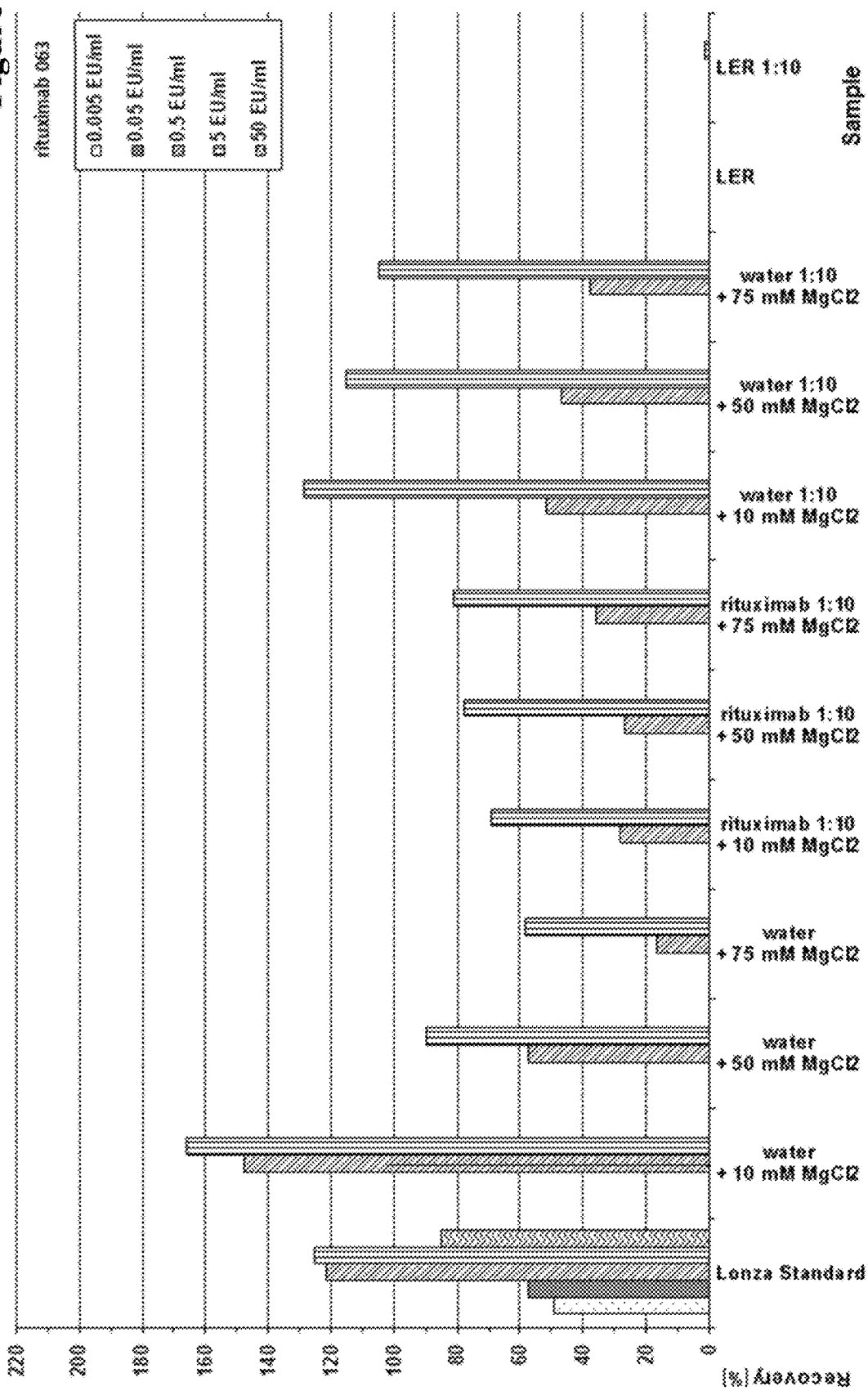
FIG. 7: Recovery rates (%) obtained by performing the protocol as described in Reference Example 4 by using Rituximab as sample. (A) Recovery rates obtained by performing the protocol as described in Reference Example 3.1 [rituximab 062]. (B) Recovery rates obtained by performing the protocol as described in Reference Example 3.2 [rituximab 063].

Reference Example 4: Comparison of 2 and 4 Hours Incubation Time after Addition of $MgCl_2$ The rituximab samples were shaken for 60 min in order to achieve the "positive LER effect". After addition of $MgCl_2$ the undiluted samples were incubated for 2 or 4 h, then 1:10 diluted and measured in the LAL assay. The different samples which have been tested in the LAL assay are shown in FIGS. 7(A) and 7(B) (i.e. [rituximab 062] and [rituximab 063], respectively).

The samples have been prepared in a 1.5 ml screw neck vial by Macherey-Nagel.

Step 1: Preparation of the Samples
   Preparation of rituximab/water for 10 mM $MgCl_2$: 897 µl rituximab/water+99.8 µl of different CSE stock solutions so that 0.5 and 5.0 EU/ml are obtained.
   Preparation of rituximab/water for 50 mM $MgCl_2$: 889 µl rituximab/water+98.8 µl of different CSE stock solutions so that 0.5 and 5.0 EU/ml are obtained.
   Preparation of rituximab/water for 75 mM $MgCl_2$: 883 µl rituximab/water+98.1 µl of different CSE stock solutions so that 0.5 and 5.0 EU/ml are obtained.

Step 2: Preparation of Two LER Positive Controls
   rituximab 900 µl+100 µl CSE so that 0.5 and 5.0 EU/ml are obtained.
   Dilution of one of the LER positive controls at a ratio of 1:10 with endotoxin-free water.

Step 3: Shaking
   All samples as well as the LER positive control are shaken for 1 h: [Heidolph Multi Reax shaker, high speed (2,037 rpm) at room temperature]

Step 4: Addition of $MgCl_2$
   A 4 M $MgCl_2$ stock solution was used.
   For 10 mM $MgCl_2$ 2.5 µl of the 4M solution are added to the spiked sample
   For 50 mM $MgCl_2$ 12.5 µl of the 4M solution are added to spiked sample
   For 75 mM $MgCl_2$ 19 µl of the 4M solution are added to spiked sample
   Shake for 1 min [Heidolph Multi Reax shaker, high speed (2,037 rpm) at room temperature]

Step 5: Incubation Time
   The (undiluted) samples (as well as the LER positive controls) are portioned. One half of each sample (about 500 µl) was incubated for 2 h and the other half was incubated for 4 h, respectively.

Step 6: Dilution
   Shake for 2 min [Heidolph Multi Reax shaker, high speed (2,037 rpm) at room temperature]
   Dilutions at a ratio of 1:10 were prepared: 900 µl LAL water+100 µl sample (i.e. rituximab sample or water sample).
   Shake for 1 min [Heidolph Multi Reax shaker, high speed (2,037 rpm) at room temperature]

Step 7: LAL Assay
- 100 µl of each samples were applied onto a plate in double determination
- Incubation in the reader at 37° C. for 10 min.
- 100 µl chromogen were applied to each sample.
- Starting the measurement in the reader Results and Discussion:

The results are shown in FIGS. 7(A) and 7(B) (i.e. [rituximab 062] and [rituximab 063], respectively). Here the recovery rates of 0.5 and 5.0 EU/ml endotoxin was measured. When 10-75 mM $MgCl_2$ was added to the samples, the recovery was the same in the samples which were incubated for 2 h (FIG. 7(A), i.e. [rituximab 062]) and in the samples which were incubated for 4 h (FIG. 7(B), i.e. [rituximab 063]). In both experiments the recovery rates are very similar. In addition, in the samples which were spiked with 5.0 EU/ml endotoxin satisfactory recovery rates (80-90%) were obtained, even without dialysis. In the samples which were spiked with 0.5 EU/ml endotoxin the recovery rates were approximately 35-45%. Importantly, without dilution (at a ratio of 1:10), complete LER is observed, i. e. 0% recovery, also in the presence of 10-75 mM $MgCl_2$. The water controls as well as the LER positive controls were satisfactory. In these experiments no dialysis has been performed. However, further experiments demonstrated that without dialysis, the LER effect is sometimes overcome and sometimes not. Thus, dialyzing the samples results in a more robust method for overcoming the LER effect.

Figure 8A:
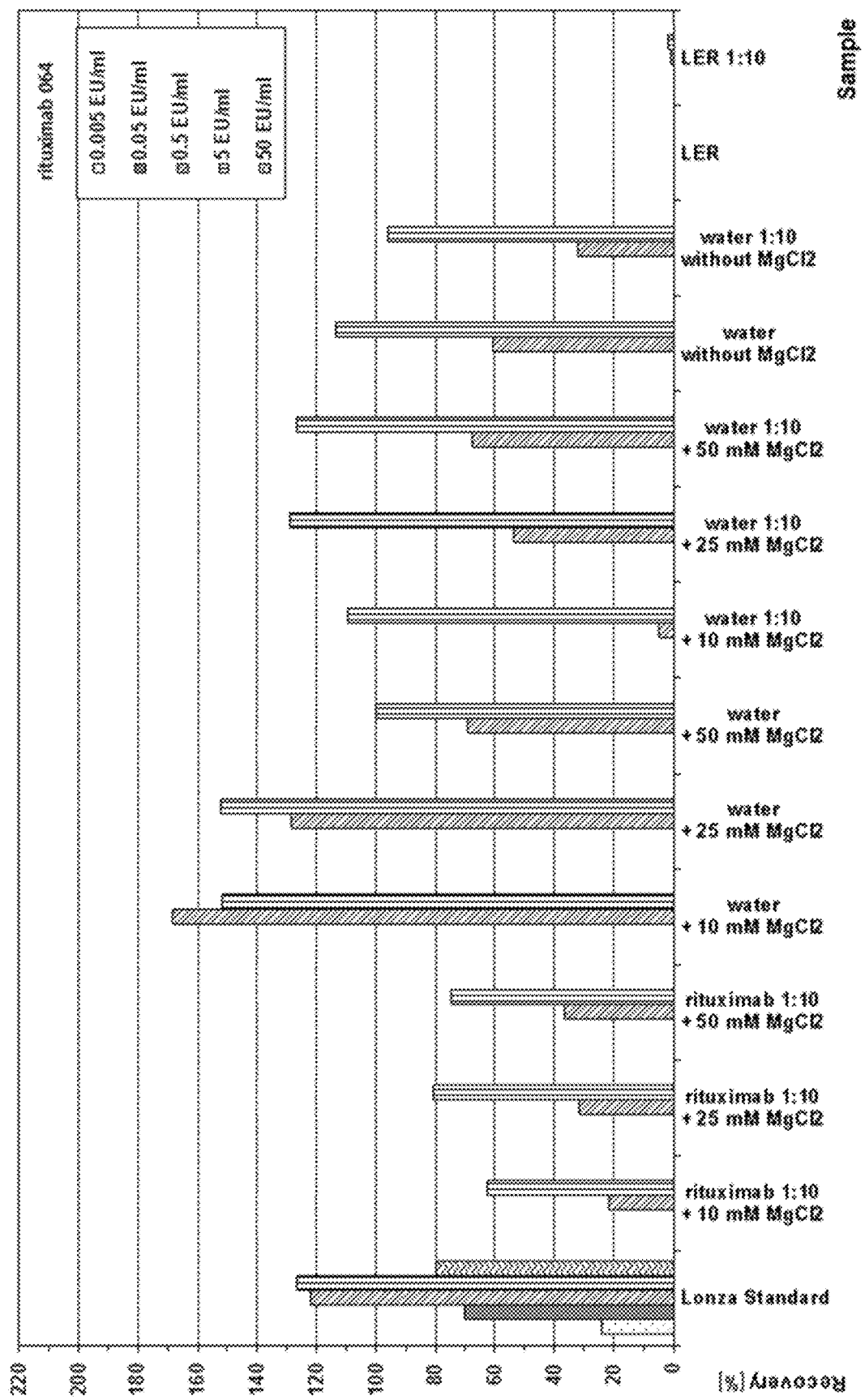
FIG. 8: Recovery rates (%) obtained by performing the protocol as described in Reference Example 5 by using Rituximab as sample. (A) Recovery rates obtained by performing the protocol as described in Reference Example 4.1 [rituximab 064]. (B) Recovery rates obtained by performing the protocol as described in Reference Example 4.2 [rituximab 065].
Figure 8B:
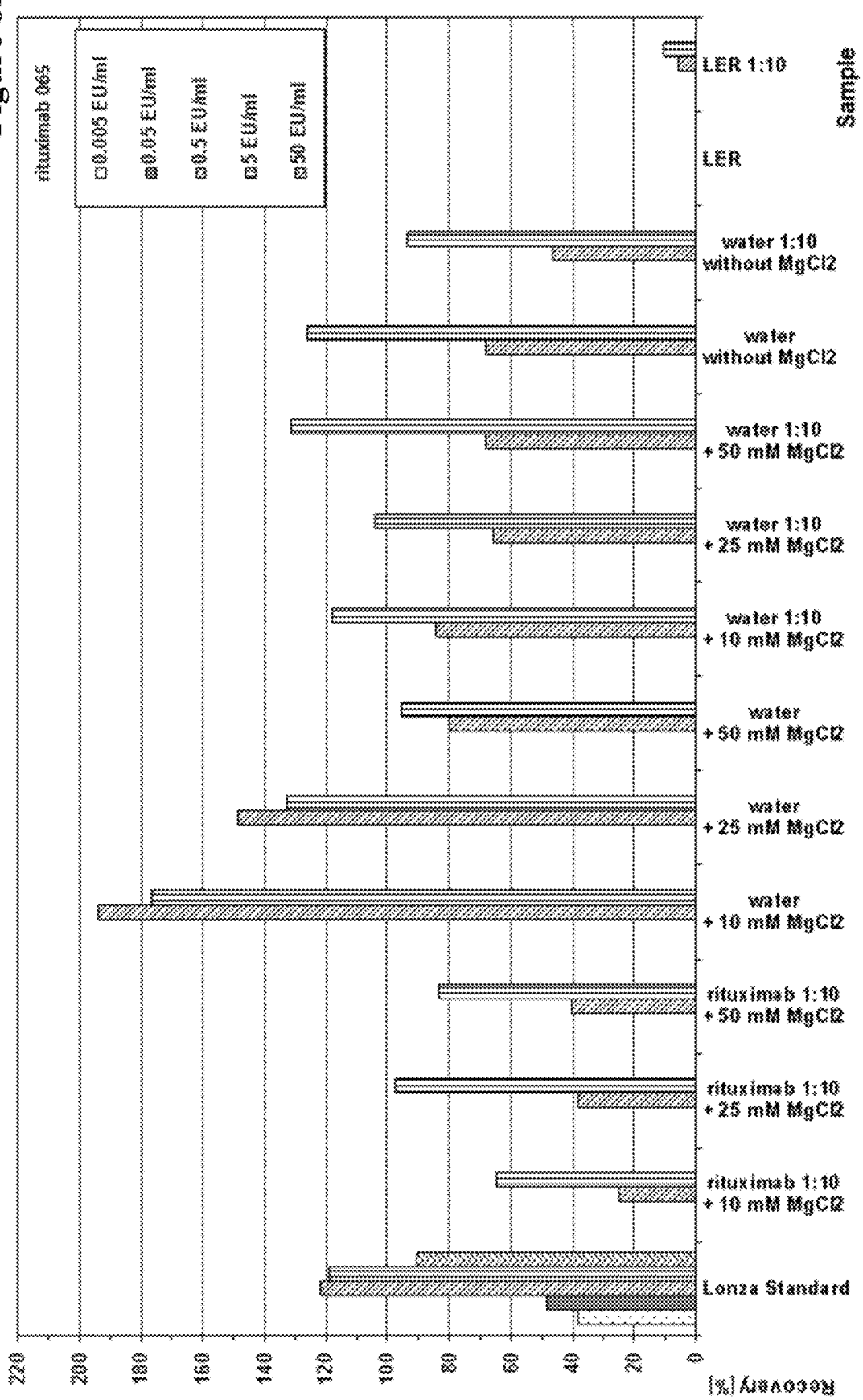

Reference Example 5: Comparison of 2 Hours Incubation Time after Addition of Different Amounts of $MgCl_2$ with No Incubation Time after Addition of Different Amounts of $MgCl_2$ The rituximab samples were shaken for 60 min in order to achieve the "positive LER effect". After addition of $MgCl_2$ the undiluted samples were either not incubated or incubated for 2 h. Then 1:10 diluted and measured in the LAL assay. The different samples which have been tested in the LAL assay are shown in FIGS. 8(A) and 8(B) (i.e. [rituximab 064] and [rituximab 065], respectively).

Reference Example 5.1: No Incubation Time after Addition of $MgCl_2$

In this experiment, no incubation was performed after addition of $MgCl_2$ to the samples.

The samples have been prepared in a 1.5 ml screw neck vial by Macherey-Nagel.

Step 1: Preparation of the Samples
- Preparation of rituximab/water for 10 mM $MgCl_2$: 897 µl rituximab/water+99.8 µl of different CSE stock solutions so that 0.5 and 5.0 EU/ml are obtained
- Preparation of rituximab/water for 25 mM $MgCl_2$: 895 µl rituximab/water+99.4 µl of different CSE stock solutions so that 0.5 and 5.0 EU/ml are obtained.
- Preparation of rituximab/water for 50 mM $MgCl_2$: 889 µl rituximab/water+98.8 µl of different CSE stock solutions so that 0.5 and 5.0 EU/ml are obtained.

Step 2: Preparation of Two LER Positive Controls
- rituximab 900 µl+100 µl CSE so that 0.5 and 5.0 EU/ml are obtained.
- Dilution of one of the LER positive controls at a ratio of 1:10 with endotoxin-free water Step 3: Shaking
- All samples as well as the LER positive control were shaken (i.e. vortexed) for 60 min [Heidolph Multi Reax shaker, high speed (2,037 rpm) at room temperature]

Step 4: Addition of $MgCl_2$
- A 4 M $MgCl_2$ stock solution was used.
  - For 10 mM $MgCl_2$ 2.5 µl of the 4M solution are added to the spiked sample
  - For 25 mM $MgCl_2$ 6.25 µl of the 4M solution are added to spiked sample
  - For 50 mM $MgCl_2$ 12.5 µl of the 4M solution are added to spiked sample
- Shake for 1 min [Heidolph Multi Reax shaker, high speed (2,037 rpm) at room temperature]

Step 5: Dilution
- Shake for 1 min [Heidolph Multi Reax shaker, high speed (2,037 rpm) at room temperature]
- Dilutions at a ratio of 1:10 were prepared.
- Shake for 1 min [Heidolph Multi Reax shaker, high speed (2,037 rpm) at room temperature]

Step 6: LAL Assay
- 100 µl of each samples were applied onto a plate in double determination
- Incubation in the reader at 37° C. for 10 min.
- 100 µl chromogen were applied to each sample.
- Starting the measurement in the reader.

Results and Discussion:

The results are shown in FIG. 8(A) (i.e. [rituximab 064]). For the discussion of the results see Reference Example 4.2.

Reference Example 5.2: Incubation of 2 h after Addition of $MgCl_2$

In this experiment, the samples were incubated for 2 h after addition of $MgCl_2$. Steps 1 to 4 were performed as described above under Reference Example 4.1. However, after addition of $MgCl_2$ the undiluted samples were incubated for 2 h at room temperature (21° C.)). After the incubation, the following steps 5 and 6 were performed. The different samples which have been tested in the LAL assay are shown in FIG. 8(B) (i.e. [rituximab 065]).

Step 5: Dilution
- Shake for 2 min [Heidolph Multi Reax shaker, high speed (2,037 rpm) at room temperature]
- Dilutions at a ratio of 1:10 were prepared: 900 µl LAL water+100 µl sample (i.e. rituximab sample or water sample)
- Shake for 1 min [Heidolph Multi Reax shaker, high speed (2,037 rpm) at room temperature]

Step 6: Preparation of Two LER Positive Controls
- rituximab 900 µl+100 µl CSE so that 0.5 and 5.0 EU/ml are obtained.
- Dilution of one of the LER positive controls at a ratio of 1:10 with endotoxin-free water Step 7: Shaking
- All samples as well as the LER positive control were shaken for 1 h [Heidolph Multi Reax shaker, high speed (2,037 rpm) at room temperature]

Step 8: LAL Assay
- 100 µl of each samples were applied onto a plate in double determination
- Incubation in the reader at 37° C. for 10 min.
- 100 µl chromogen were applied to each sample.
- Starting the measurement in the reader.

Results and Discussion:

The results of Reference Example 4.1 are shown in FIG. 8(A) (i.e. [rituximab 064]); the results of Reference Example 4.2 are shown in FIG. 8(B) (i.e. [rituximab 065]). In these two experiments, dilution and LAL measurement was either carried out immediately after addition of $MgCl_2$ (FIG. 8(A), [rituximab 064]) or after leaving the sample to rest for 2 h after addition of $MgCl_2$ (FIG. 8(B), [rituximab 065]). All recovery values were very similar and in the samples which were spiked with 5.0 EU/ml CSE, satisfactory (60-80%) recovery rates have been obtained even without dialysis. Interestingly, after an incubation time of 2 h, the 25 mM $MgCl_2$ concentration resulted in 100% recovery. Thus, an incubation time after addition of $MgCl_2$ seems to be a valuable measure to decrease the LER effect. However, the recovery values for the samples which were spiked with 0.5 EU/ml CSE were low with approximately 20-35%. This indicates that beside addition of $Mg^{2+}$ and dilution, dialysis represents a necessary step for reliably overcoming the LER effect. In these experiments the water control values were satisfactory. The undiluted LER positive control was also satisfactory, i.e. 0%.

Figure 9:
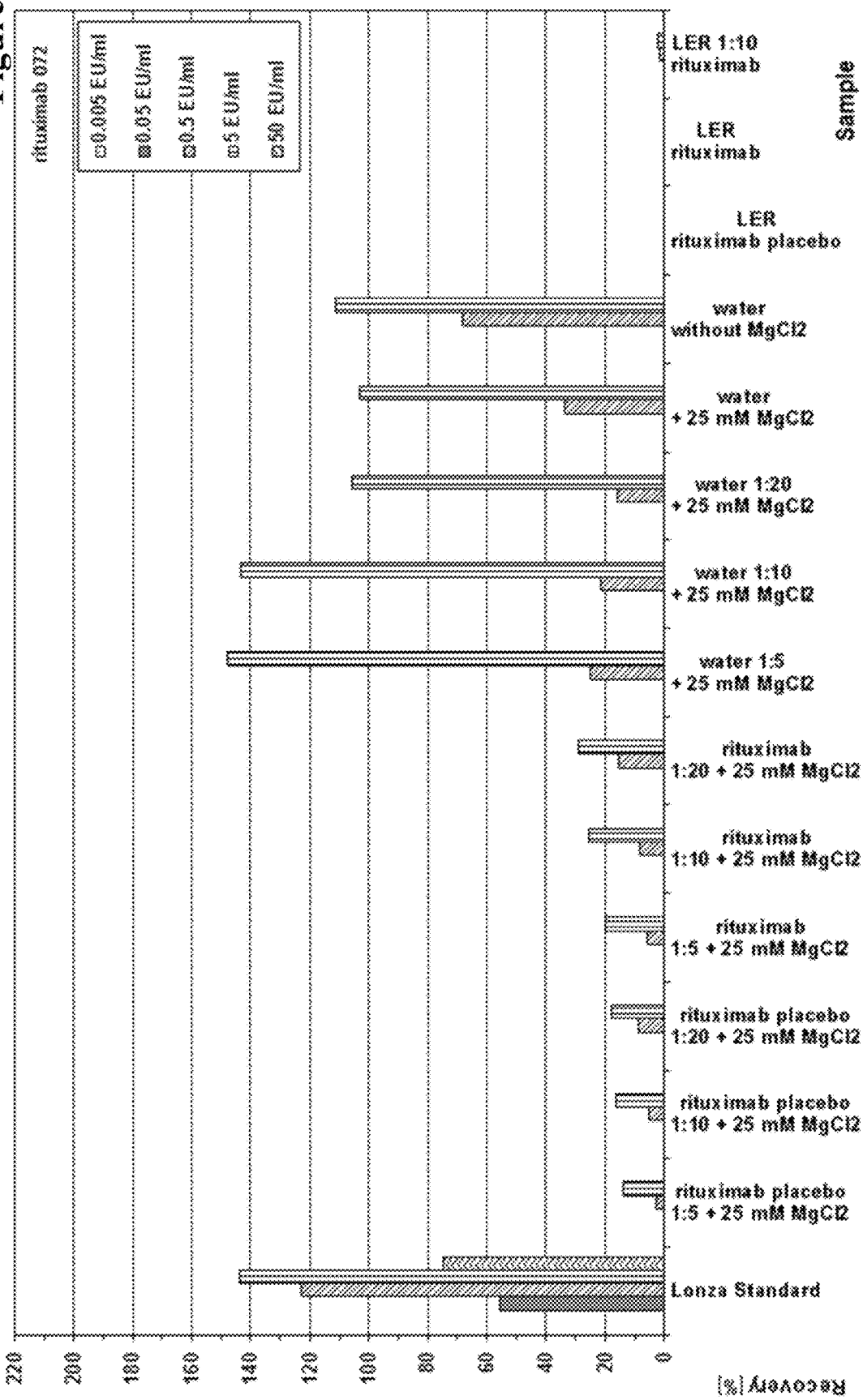
FIG. 9: Recovery rates (%) obtained by performing the protocol as described in Reference Example 6 by using rituximab and rituximab placebo as sample. [rituximab 072].

Reference Example 6: Comparison of Different Dilutions with Rituximab and Rituximab Placebo Samples After spiking, rituximab and rituximab placebo samples were shaken for 60 min in order to achieve the "positive LER effect". After addition of $MgCl_2$ the undiluted samples were shaked for 1 h and diluted at a ratio of 1:2, 1:5, 1:10 or 1:20 Afterwards the LAL assay was performed. The different samples which have been tested in the LAL assay are shown in FIG. 9 (i.e. [rituximab 072]).

In particular, the following experiment has been performed:

Step 1: Preparation of the Samples
  Preparation of rituximab/rituximab placebo/water for 25 mM $MgCl_2$: 895 μl rituximab/rituximab placebo/water+99.4 μl of different CSE stock solutions so that 0.5 and 5.0 EU/ml are obtained.

Step 2: Preparation of Three LER Positive Controls
  rituximab placebo 450 μl+50 μl CSE so that 0.5 und 5.0 EU/ml are obtained (first LER positive control).
  rituximab 450 μl+50 μl CSE so that 0.5 und 5.0 EU/ml are obtained (second LER positive control).
  rituximab 450 μl+50 μl CSE so that 0.5 und 5.0 EU/ml are obtained. Afterwards, this sample was diluted at a ratio of 1:10 (third LER positive control).

Step 3: Shaking
  All samples as well as the LER positive controls were shaken (i.e. vortexed) for 60 min [Heidolph Multi Reax shaker, high speed (2,037 rpm) at room temperature]

Step 4: Addition of $MgCl_2$
  A 4 M $MgCl_2$ stock solution was used.
  For 25 mM $MgCl_2$ 6.25 μl of the 4M solution are added to spiked sample
  Shake for 1 min [Heidolph Multi Reax shaker, high speed (2,037 rpm) at room temperature]

Step 5: Dilution
  The samples were diluted as follows:
    Dilution at a ratio of 1:5: 400 μl water+100 μl sample
    Dilution at a ratio of 1:10: 450 μl water+50 μl sample
    Dilution at a ratio of 1:20: 475 μl water+25 μl sample
  One of the three LER positive controls was diluted at a ratio of 1:10.
  The water without $MgCl_2$ was not diluted.
  Shake for 1 min [Heidolph Multi Reax shaker, high speed (2,037 rpm) at room temperature]

Step 6: LAL Assay
  100 μl of each samples were applied onto a plate in double determination
  Incubation in the reader at 37° C. for 10 min.
  100 μl chromogen was applied to each sample.
  Starting the measurement in the reader.

Results and Discussion:
The results are shown in FIG. 9 (i.e. [rituximab 072]). Importantly, the results for rituximab and rituximab placebo show no significant differences. This indicates that the LER effect in rituximab is mainly based on the buffer system (i.e. citrate buffer with polysorbate 80) and that the antibody (i.e. rituximab) does not have a significant impact on the LER effect. However, in this experiment the recovery rates are unsatisfactory for both rituximab and rituximab placebo. In the experiment described above, the water control values were satisfactory. The undiluted LER positive controls were satisfactory, too, with recovery rates of 0%.

Reference Example 7: Influence of Incubation Time Before Addition of $MgCl_2$ on the Recovery Rate in Rituximab and Rituximab Placebo Samples In the following experiment it was tested whether incubation times before addition of $MgCl_2$ have an influence on the recovery rate of rituximab and rituximab placebo samples. In particular, rituximab and rituximab placebo samples were shaken for 60 min in order to achieve the "positive LER effect". Then the samples were incubated at 4° C. for 0 h to 3 days. Afterwards, $MgCl_2$ was added to a concentration of 50 mM and the samples were diluted. Then, dialysis was performed with a dialysis membrane which was not BSA-blocked. The different samples which have been tested in the LAL assay are shown in FIG. 10 (i.e. [rituximab 079], and [rituximab 082]).

The samples have been prepared in a 1.5 ml screw neck vial by Macherey-Nagel.

Step 1: Preparation of the Samples
  Preparation rituximab/rituximab placebo/water for 50 mM $MgCl_2$: 5,346 μl rituximab/rituximab placebo/water+596 μl of different CSE stock solutions so that 0.5 or 5.0 EU/ml were obtained.
  Vortex for 60 min [Heidolph Multi Reax shaker, high speed (2,037 rpm) at room temperature]
  For the further procedure 1 ml of each sample was transferred into new vials Step 2: Incubation Time
  The samples were put into the refrigerator at 4° C. for 0 h, 4 h, 1 day, 3 days, or 7 days.
  After the incubation time of 1 day, 3 days or 7 days the samples were shaken for 2 min [Heidolph Multi Reax shaker, high speed (2,037 rpm) at room temperature]. After 0 h and 4 h incubation time the samples were not shaked.

Step 3: Addition of $MgCl_2$
  A 5 M $MgCl_2$ stock solution (i.e. 0.9055 g $MgCl_2$ in 0.891 ml water) was used
  For 50 mM $MgCl_2$ 10 μl of the 5 M solution were added to the spiked samples
  Shake for 1 min [Heidolph Multi Reax shaker, high speed (2,037 rpm) at room temperature Step 4: Dilution
  Dilutions at a ratio of 1:10 were prepared: 900 μl LAL water+100 μl sample (i.e. rituximab sample, rituximab placebo sample or water sample)
  The water without $MgCl_2$ was not diluted.

Shake for 1 min [Heidolph Multi Reax shaker, high speed (2,037 rpm) at room temperature Step 5: Dialysis The samples were added into a 1 ml dialyzer. Dialysis was performed against 1 l Aqua Braun at 24° C. for 4 h, and after 2 h the water was changed. The new water also had a temperature of 24° C. A 500 Da membrane was used which has not been incubated with BSA before.

The dialyzers were located in three 2 l beakers and rotated since there was a long stirrer (i.e. stir bar) in each beaker.

After dialysis the samples have been transferred into new 1.5 ml vials.

Step 6: Shaking

Shake for 20 min [Heidolph Multi Reax shaker, high speed (2,037 rpm) at room temperature]

Step 7: Preparation of the LER Positive Control

The LER control was prepared 1 h before the end of the 4 h dialysis so that it is ready at the same time as the other samples.

rituximab or rituximab placebo 900 µl+100 µl CSE to obtain 5.0 EU/mL CSE

Shake at room temperature for 1 h [Heidolph Multi Reax shaker, high speed (2,037 rpm)]

Step 8: LAL Assay

100 µl of each samples were applied onto a plate in double determination

Incubation in the reader at 37° C. for 10 min.

100 µl chromogen were applied to each sample.

Starting the measurement in the reader.

Figure 10A:
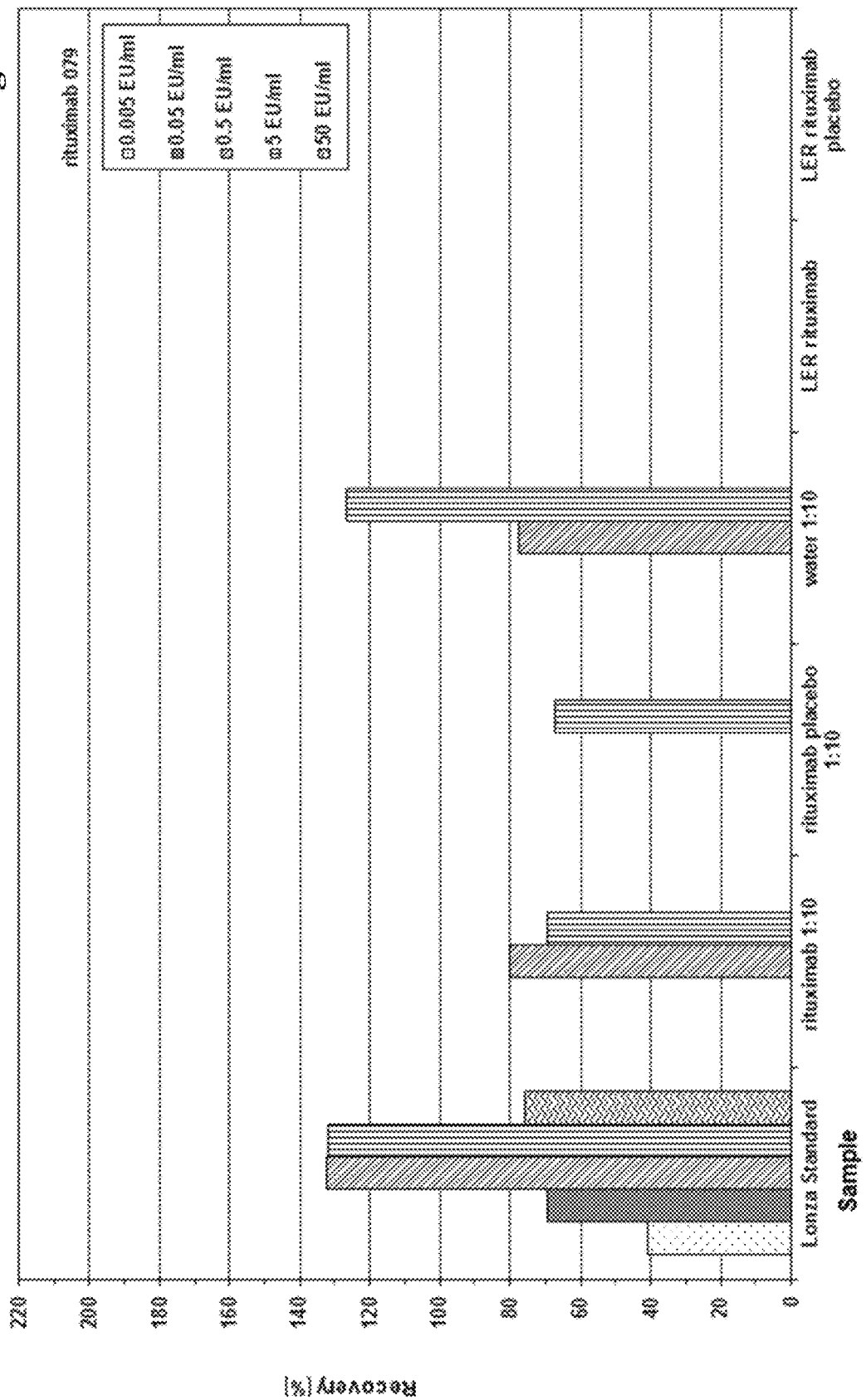
FIG. 10: Recovery rates (%) obtained by performing the protocol as described in Reference Example 7 by using rituximab and rituximab placebo as sample. (A) [rituximab 079] no incubation; (B) [rituximab 080] 4 h incubation; (C) [rituximab 081] 1 day incubation; (D) [rituximab 082] 3 days incubation.
Figure 10B:
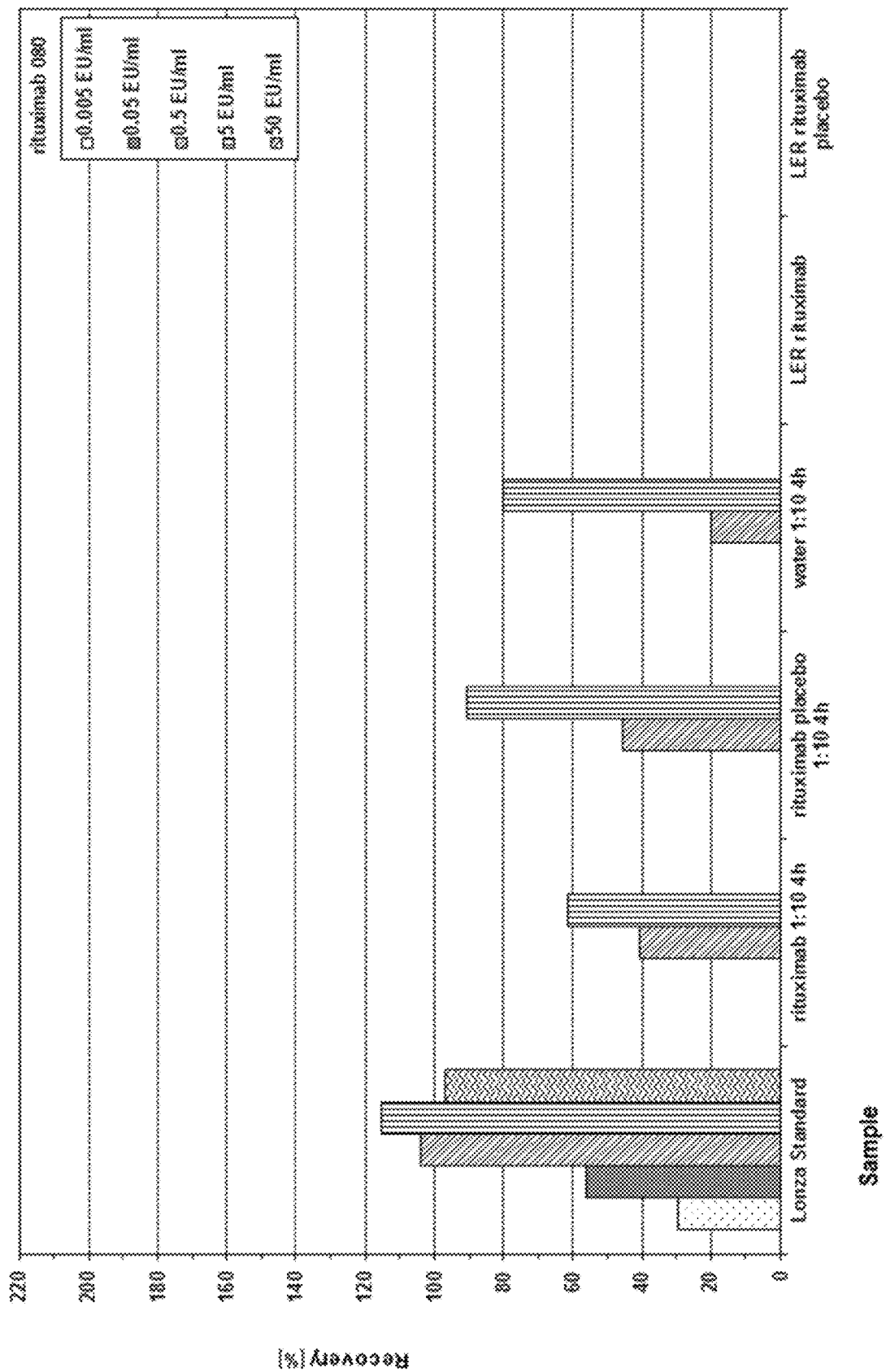
Figure 10C:
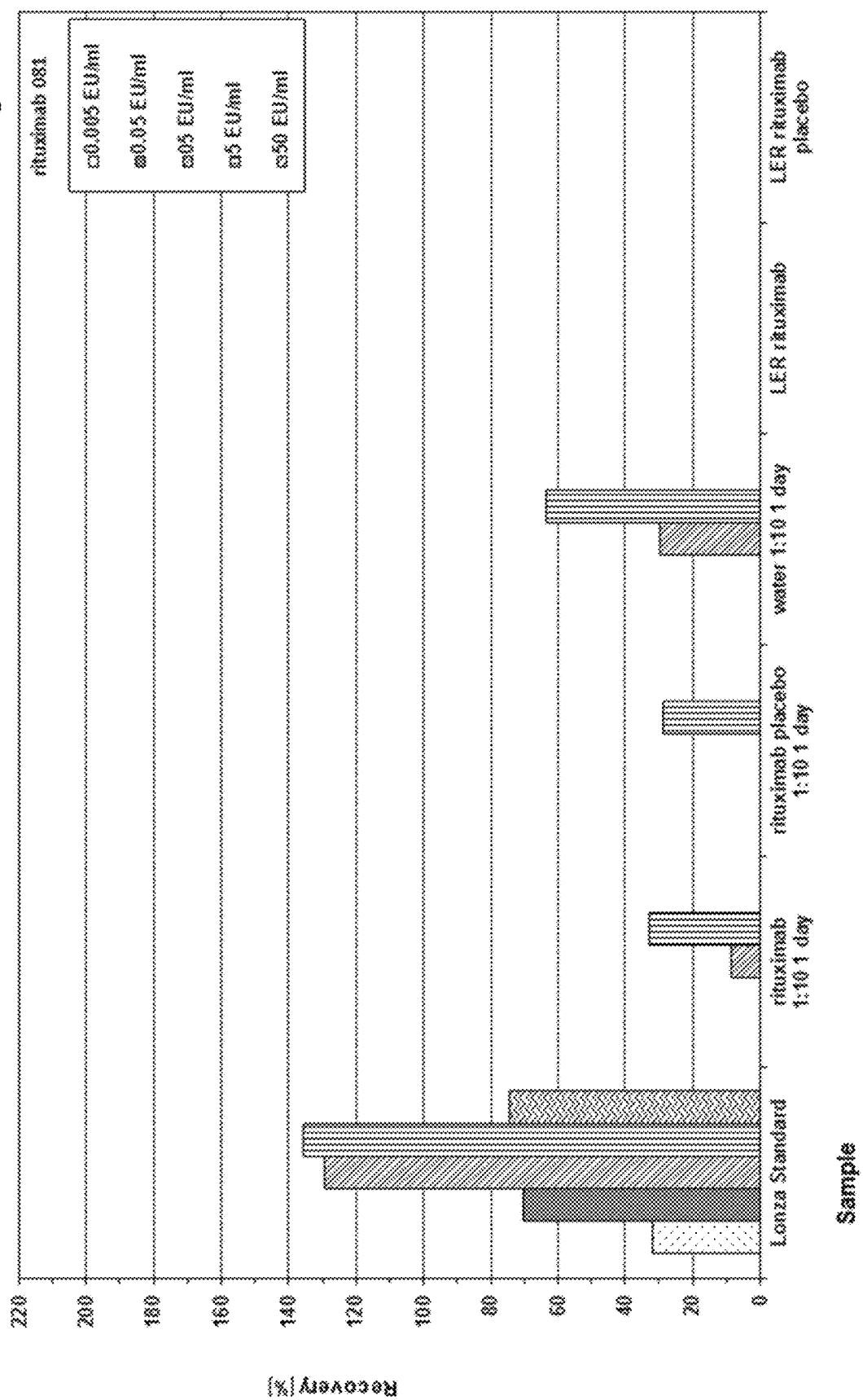
Figure 10D:
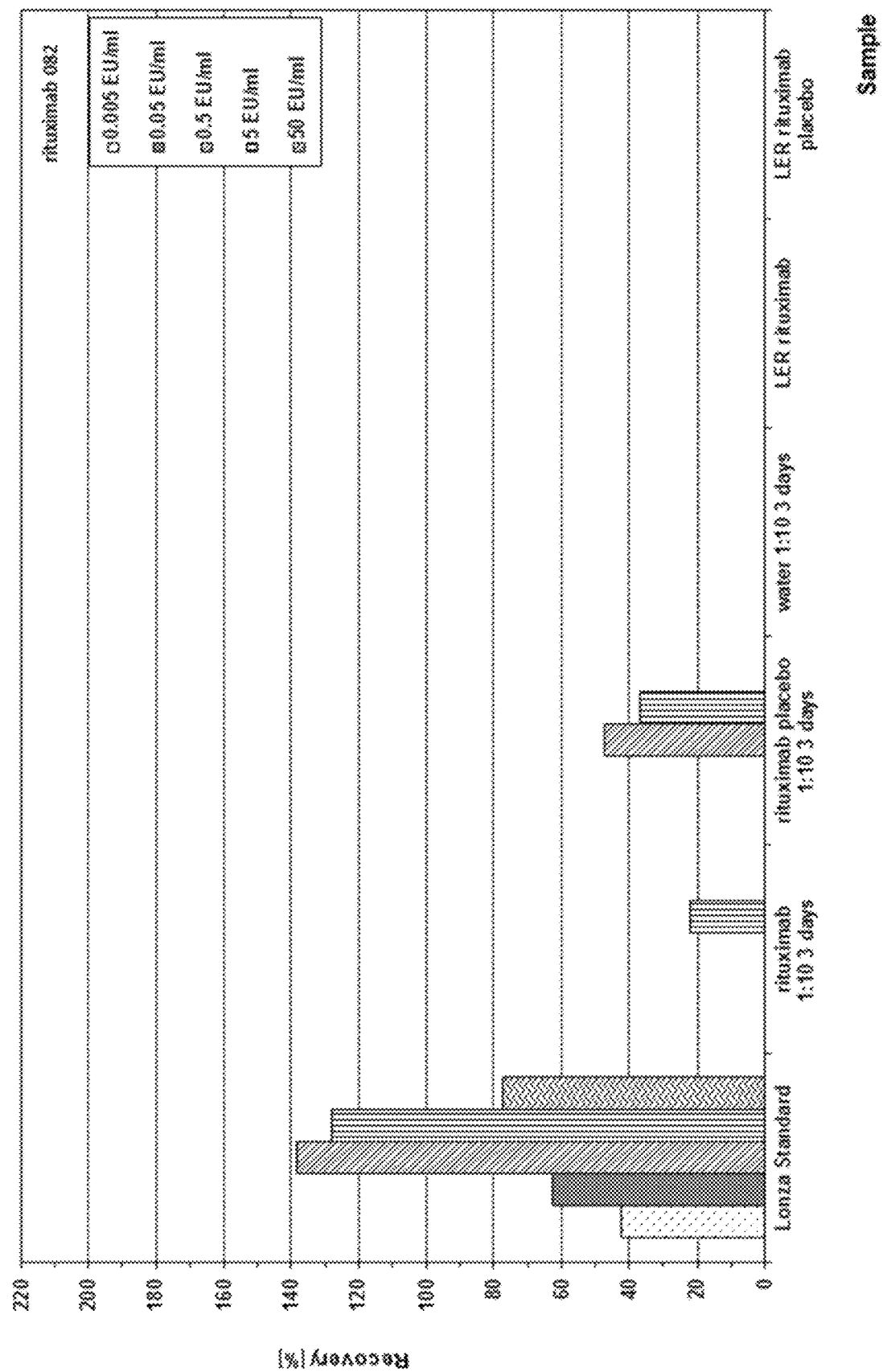

Results and Discussion:

The results are shown in FIG. 10(A) (i.e. [rituximab 079], no incubation), FIG. 10(B) (i.e. [rituximab 080], 4 h incubation), FIG. 10(C) (i.e. [rituximab 081], 1 day incubation), and FIG. 10(D) (i.e. [rituximab 082], 3 days incubation). The results for the 7 days incubation are not shown. The results again demonstrate that by using the herein described protocols good recovery rates can be obtained for rituximab as well as for rituximab placebo samples. In addition, this experiment demonstrates that an incubation time before addition of $MgCl_2$ does not improve the recovery rates. In particular, while the incubation time of 0-4 h led to recovery rates which are within the desired range (50-200%), the incubation times of 1 day and 3 days led to lower recovery rates (approximately 20-30%). If no (i.e. 0 h) incubation was performed, very good recovery rates were obtained for rituximab (70-80%). Also for rituximab placebo which was spiked with 5.0 EU/ml CSE, the recovery rate was satisfactory. The recovery rate for rituximab placebo which was spiked with 0.5 EU/ml CSE was negative since the blank was very high. This may indicate that this blank sample was contaminated with endotoxin. In this experiment also recovery rates of the water control (80-120%) as well as of the LER positive control (~0%) were satisfactory.

Reference Example 8: The Protocol of the State of the Art ("LAL Assay") and Modifications Thereof Cannot Overcome the LER Effect in Rituximab or Rituximab Placebo In this Example it was determined whether the commonly known LAL assay is able to detect endotoxins in rituximab and rituximab placebo preparations. Therefore, the following materials have been used:

[rituximab 002]: Lonza CSE+Lonza reagent (i.e. Lonza kit)
[rituximab 004]: ACC CSE or Lonza CSE, respectively+ACC reagent (i.e. ACC kit)
[rituximab 005]: Lonza CSE+ACC reagent (i.e. ACC kit)

The LAL assays have been precisely been performed as described by the manufacturer.

Figure 11A:
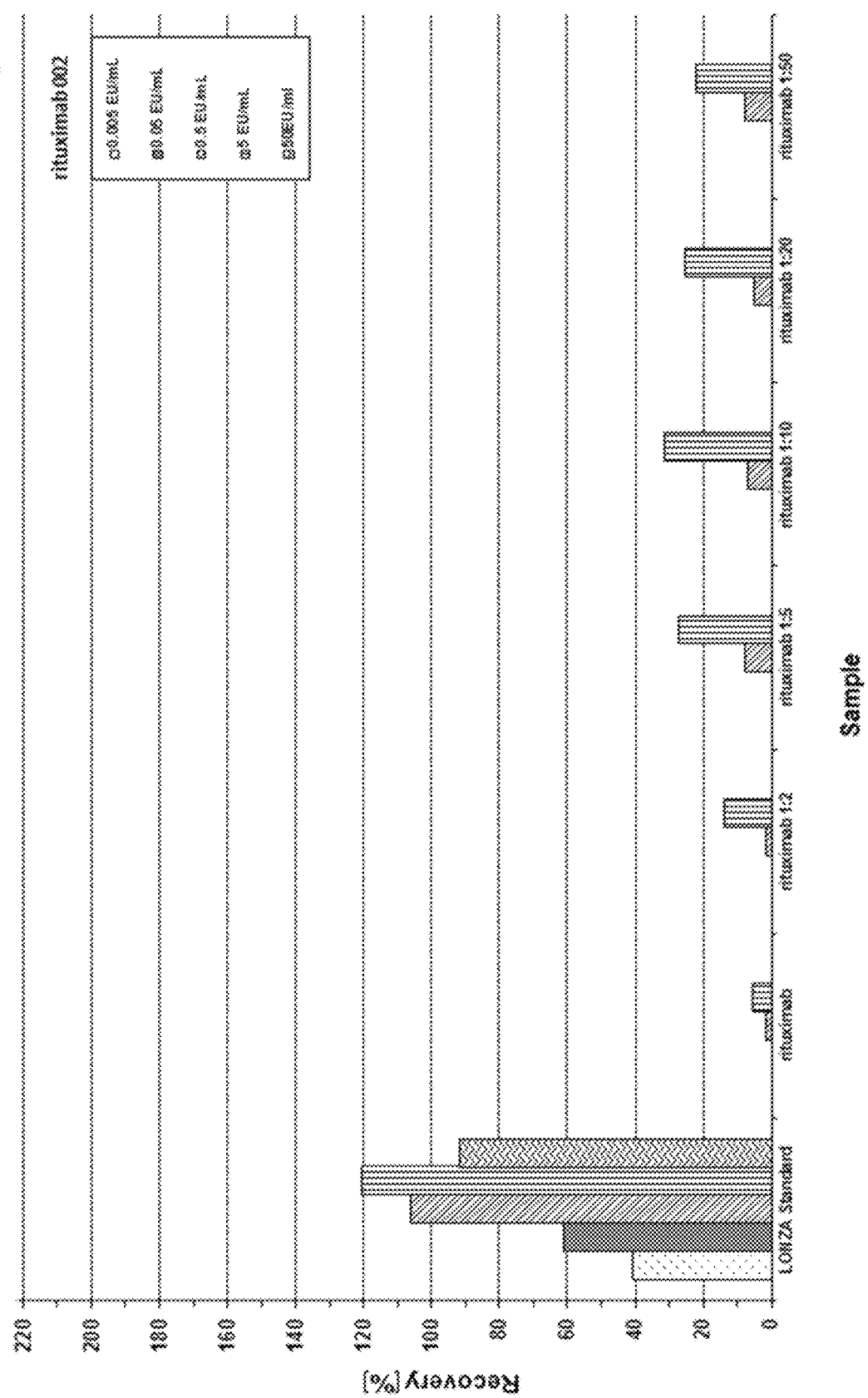
FIG. 11: Recovery rates (%) obtained by performing the LAL assay as described in Reference Example 8 by using Rituximab as sample. (A) [rituximab 002] LAL assay with different dilutions; (B) [rituximab 004] comparison of Lonza and ACC CSE spiking; (C) [rituximab 005] LAL assay with different dilutions and pH adjustment.
Figure 11B:
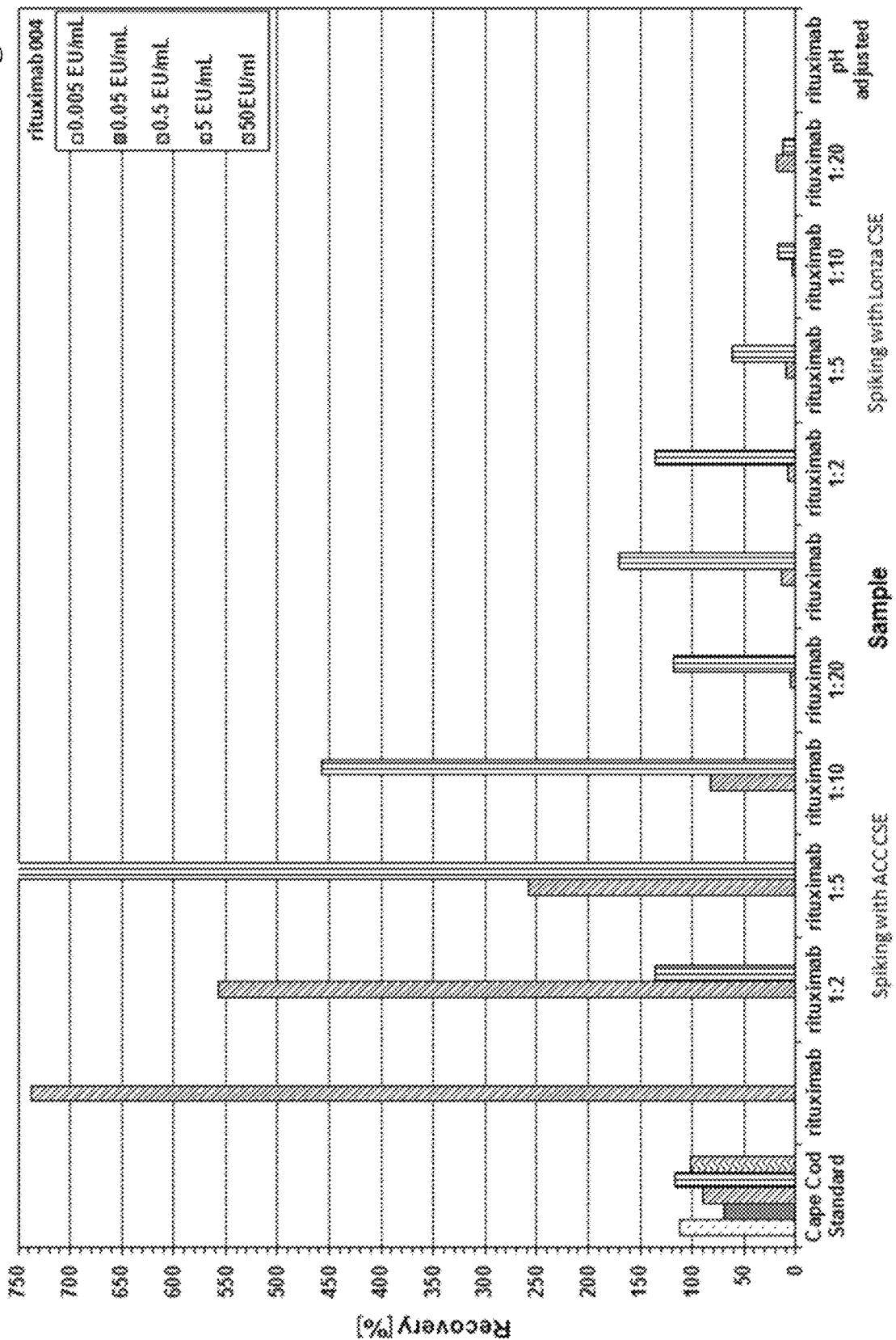
Figure 11C:
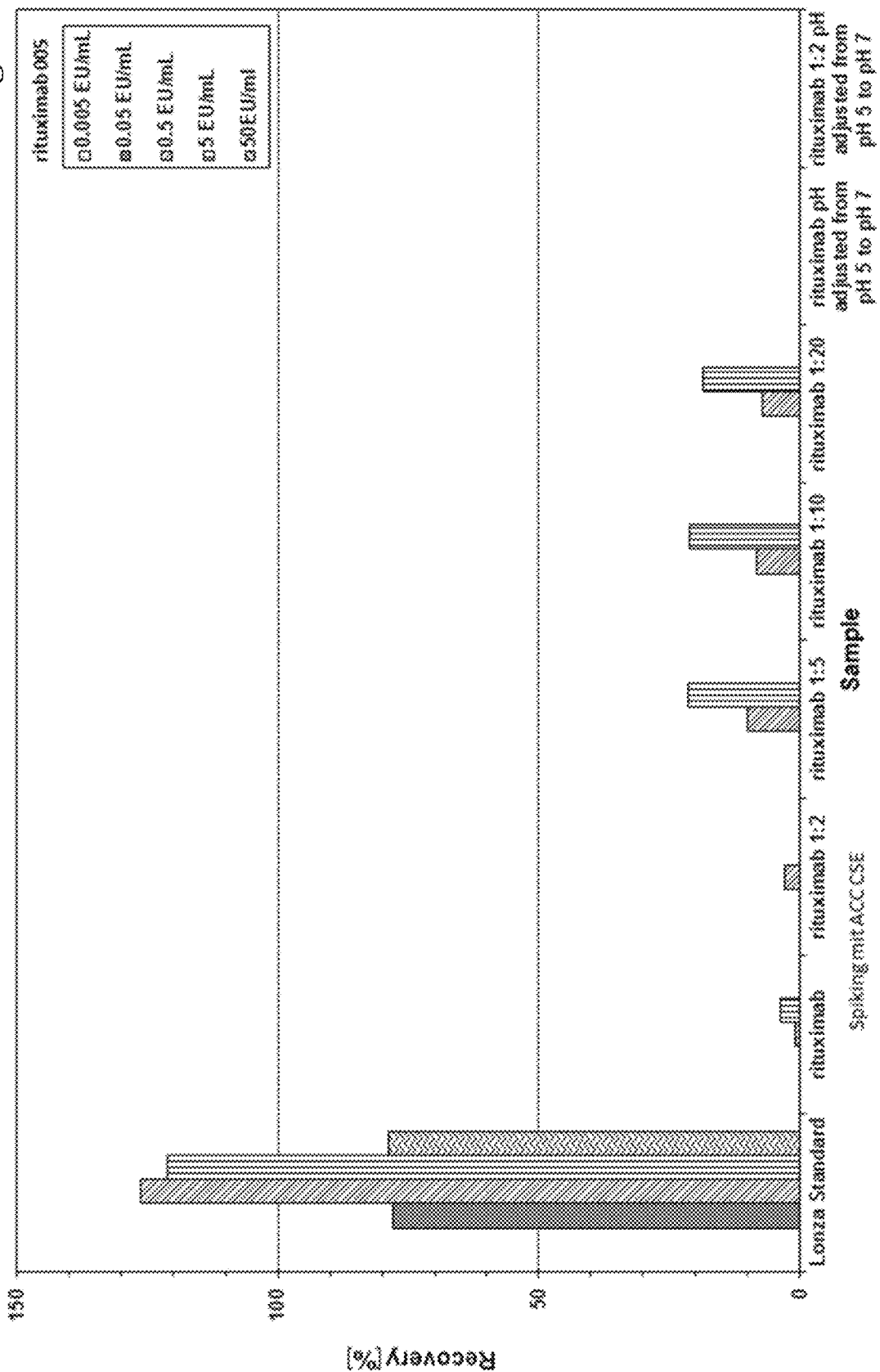

As can be seen from FIGS. 11(A)-(C) (i.e. [rituximab 002], [rituximab 004] and [rituximab 005], respectively), the standard LAL assay did not lead to satisfactory recovery rates, even if several different dilutions are tested. In particular, in one experiment (i.e. [rituximab 002]), rituximab was pipetted into a 96-well plate (i.e. a microtiter plate) and spiked with Lonza CSE to a final concentration of 0.5 EU/ml or 5.0 EU/ml. Subsequently, dilutions with water as shown in FIG. 11(A) (i.e. [rituximab 002]) were carried out in the 96-well plate. Then a LAL assay was performed. However, as can be seen in FIG. 11(A) (i.e. [rituximab 002]), 50% recovery was not reached.

In a similar experiment (i.e. [rituximab 004]) rituximab was pipetted into the wells of a microtiter plate and spiked with Lonza CSE and ACC CSE to a final concentration of 0.5 EU/ml or 5.0 EU/ml. Subsequently, dilutions with water as shown in FIG. 11(B) (i.e. [rituximab 004]) were carried out in the 96-well plate. Afterwards, measurement was performed. However, as can be seen in FIG. 11(B), with ACC CSE a recovery which is more than 200% was obtained and also the Lonza CSE spiking did not result to satisfactory recovery rates.

In further experiments, the effect of pH adjustment on the LAL assay was analyzed. In particular, in one experiment [rituximab 005] rituximab was pipetted into a microtiter plate and Lonza CSE spiking was performed in the plate. Subsequently, the dilutions with water or the pH adjustment as indicated in FIG. 11(C) [rituximab 005] were performed. However, neither the dilution nor the pH adjustment resulted in a recovery of 50% (see FIG. 11(C)[rituximab 005]).

Figure 12:
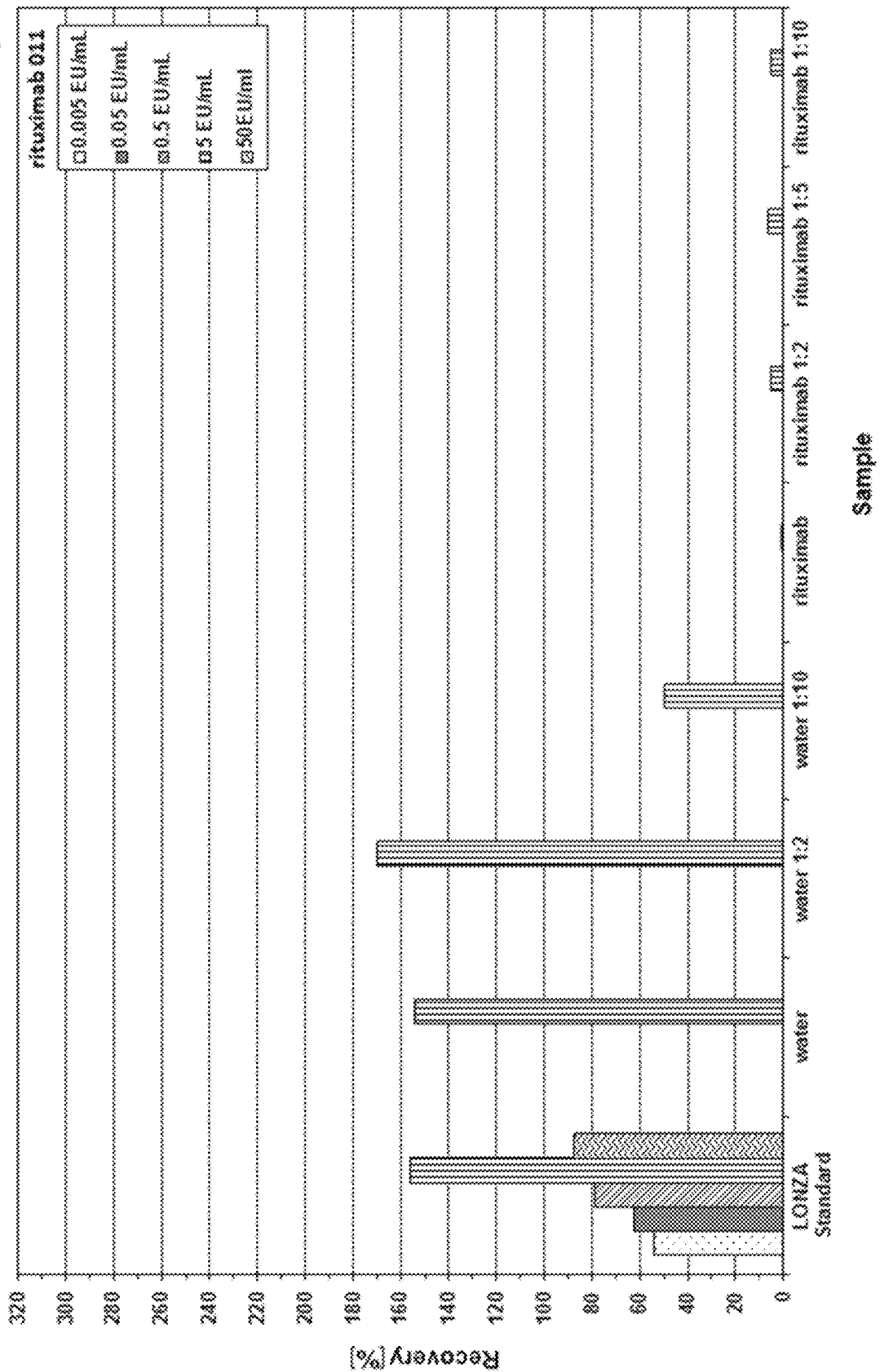
FIG. 12: Recovery rates (%) obtained by performing the LAL assay as described in Reference Example 8 by using Rituximab as sample. Dialysis and dilution alone does not overcome the LER effect [rituximab 011].

Also dialysis alone does not result in a satisfactory recovery rate. More specifically, in a further experiment, rituximab was spiked with CSE to result in a final concentration of 0.5 and 5.0 EU/ml (i.e. 900 µl rituximab solution was mixed with 100 µl CSE). Subsequently, the samples were dialysed in a 1 ml Spin Dialyser (in 1 ml Teflon chambers) for 4 hours at 4° C. with one change of water after 2 h. The dialysis membrane had a MWCO of 100 Da. Then, dilutions as shown in FIG. 12 (i.e. [rituximab 011]) were performed in the plate. Subsequently, endotoxin recovery was measured by using the LAL assay. However, good recovery rates could only be obtained for the water controls. In the case of rituximab the maximum recovery was <5% (see FIG. 12, [rituximab 011]). Thus, only dialysis and dilution does not overcome the LER effect.

Reference Example 9: Hold Time Studies

To identify and monitor the LER effect, endotoxin contents have been monitored over time in an endotoxin hold time study. Therefore, an undiluted sample of various buffers has been spiked with endotoxin and stored over time (up to 28 days). Acceptable endotoxin values recovered in the PPC after spiking with the appropriate sample mixture are defined to be in the range of 50-200% of the theoretical spike value (100%). The LER effect is indicated by a significant loss of endotoxins over time. In particular, an adverse trend of endotoxin values <50% of the theoretical spike value are indicative for the LER effect.

Several formulation buffer components were studied in an endotoxin hold time study (for results see the following table).

TABLE 1

Hold time studies

| excipient | endotoxin spike [EU/ml] | endotoxin recovery [EU/ml] at time | | | | |
|---|---|---|---|---|---|---|
| | | start ($T_0$) | day 7 | day 14 | day 21 | day 28 |
| α,α-trehalose | 5 | 4.85 | 4.65 | 3.48 | 4.32 | 4.51 |
| $NaH_2PO_4$ | 5 | 5.27 | 4.64 | 3.3 | 3.4 | 3.37 |
| $Na_2HPO_4$ | 5 | 5.99 | 5.72 | 5.07 | 5.63 | 5.06 |
| Polysorbate 20 | 5 | 4.04 | 4.03 | 4.23 | 3.94 | 4.16 |
| Polysorbate 20 + $Na_2HPO_4$ | 5 | 0.13 | 0.18 | n.d. | n.d. | n.d. |
| Polysorbate 20 + $NaH_2PO_4$ | 5 | 0.37 | 0.77 | n.d. | n.d. | n.d. |
| $Na_2HPO_4$ + $NaH_2PO_4$ | 5 | 5.12 | 4.64 | n.d. | n.d. | n.d. |
| Polysorbate 20 + $Na_2HPO_4$ + $NaH_2PO_4$ | 5 | 0.91 | <0.1 | n.d. | n.d. | n.d. |
| sodium citrate-dihydrate | 5 | 5.2 | 4.7 | 4 | 3.72 | 4.28 |
| Polysorbate 80 | 5 | 3.25 | 3.15 | 3.27 | 3.05 | 3.17 |
| NaCl | 5 | 5.76 | 5.72 | 5.45 | 4.74 | 6.49 |
| Na citrate + polysorbate 80 + NaCl | 5 | 1.33 | 0.16 | n.d. | n.d. | n.d. |
| Na citrate + polysorbate 80 | 5 | 0.8 | <0.1 | n.d. | n.d. | n.d. |
| polysorbate 80 + NaCl | 5 | 2.94 | 2.45 | n.d. | n.d. | n.d. |
| Urea | 5 | 5.14 | 6.21 | 5.66 | 5.28 | 5.29 |
| L-Leu | 5 | 5.72 | 5.61 | 5.87 | 5.01 | 5.88 |
| L-Ile | 5 | 5.70 | 5.82 | 6.24 | 5.17 | 6.17 |
| L-Thr | 5 | 5.54 | 5.65 | 5.66 | 4.76 | 5.88 |
| L-Glu | 5 | 5.28 | 5.03 | 5.50 | 4.43 | 4.24 |
| L-Phe | 5 | 5.49 | 5.50 | 5.96 | 4.98 | 6.34 |
| Gly | 5 | 4.64 | 4.57 | 4.75 | 4.27 | 5.00 | n.d. = not determined

As can be seen from the above table, the buffers comprising polysorbate 20 and $Na_2HPO_4$; polysorbate 20 and $NaH_2PO_4$; Polysorbate 20, $Na_2HPO_4^+$ and $NaH_2PO_4$; Na citrate, polysorbate 80 and NaCl; Na citrate and polysorbate 80; as well as polysorbate 80 and NaCl exhibit a LER effect.

Reference Example 10: Influence of Buffer and Detergent on the LER Effect

Figure 14A:
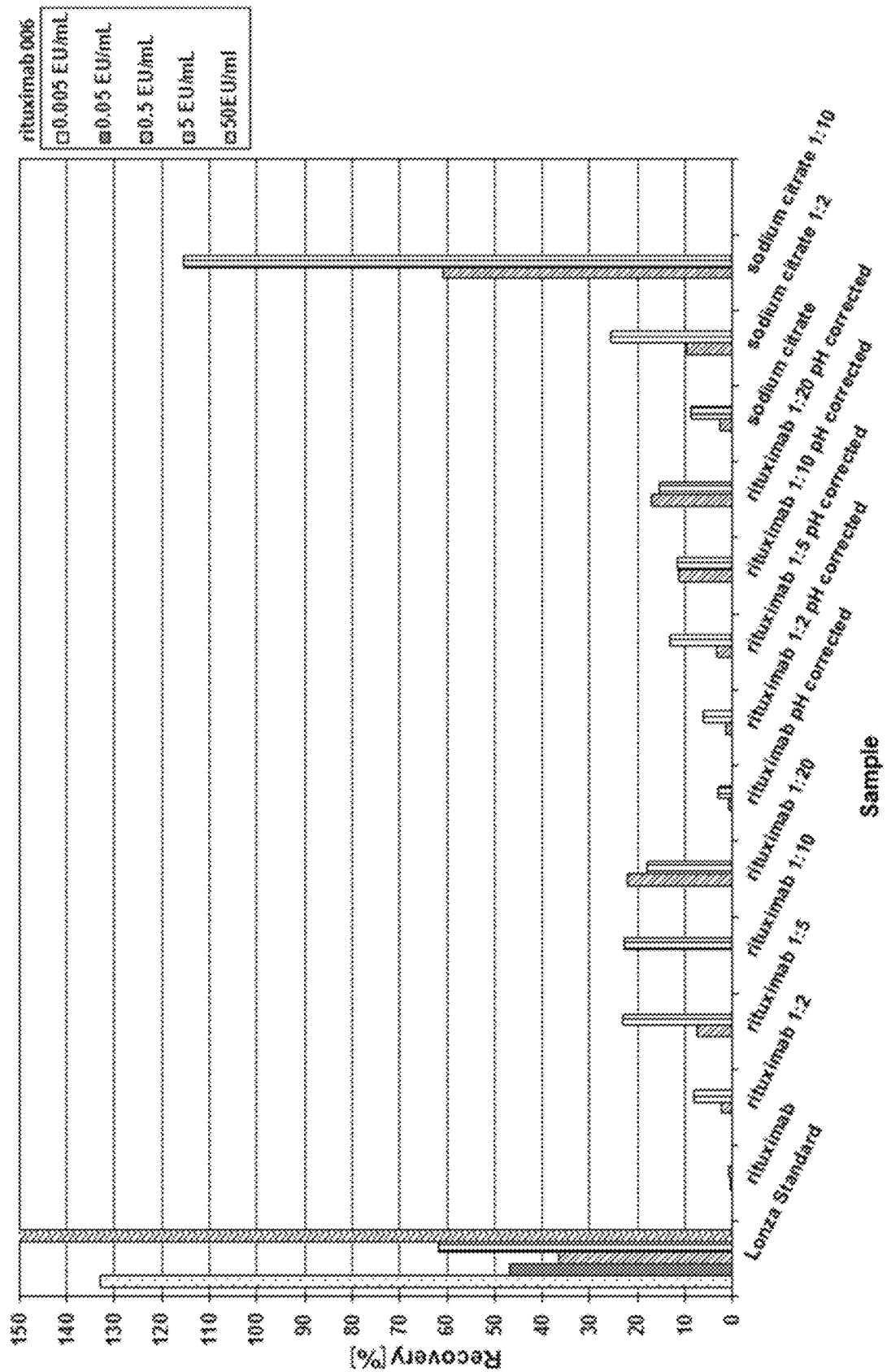
FIG. 14: Importance of the buffer system on the LER effect. Recovery rates (%) obtained by performing the LAL assay as described in Reference Example 10 are shown. (A) LAL assay when Rituximab or sodium citrate are used as sample and diluted at a ratio of 1:2, 1:5, 1:10, or 1:20 [rituximab 006]; (B) LAL assay when sodium citrate; polysorbate 80 or sodium citrate and polysorbate 80 are used as sample and diluted at a ratio of 1:2, 1:5 or 1:10 [rituximab 029].

In several experiments the effect of citrate and/or polysorbate 80 on the LER effect was analyzed. In particular, in one experiment rituximab and 25 mM sodium citrate buffer were used as samples. Before spiking, the pH was adjusted to pH 7. Subsequently, CSE spiking was performed in the plate, and the samples were diluted with water. As can be seen from FIG. 14(A) (i.e. [rituximab 006]), a satisfactory recovery rate could be obtained for sodium citrate by using a dilution of 1:10. However, in the case of rituximab a recovery of 50% could not be reached.

In another experiment 25 mM sodium citrate buffer, polysorbate 80 and a combination of both were used as samples. In particular, the concentrations as present in Rituximab were used (i.e. polysorbate 80: 0.7 mg/ml; sodium citrate: 9 mg/ml). These buffer systems were spiked with 0.5 and 5.0 EU/ml of Lonza CSE or with Cape cod CSE (except of sodium citrate, which was spiked with Lonza only, as ACC spiking of sodium citrate buffer was already performed in experiment described above and shown in FIG. 14(A) (i.e. [rituximab 006]). After spiking, a 1:2 or 1:5 dilution with water was performed in the plate. In the case of polysorbate 80, several samples led to a satisfactory recovery rate between 50% and 200%. In contrast, in the case of sodium citrate buffer, only the 1:10 dilution led to a recovery rate between 50% and 200%. This indicates that the citrate buffer has a more significant impact on the LER effect as compared to polysorbate 80. Moreover, the LER effect could not be overcome in this experiment if a combination of sodium citrate and polysorbate 80 was used as a sample. This experiment indicates that in monoclonal antibody formulations the LER effect is caused by the buffer formulation (i.e. by the combination of sodium citrate buffer and polysorbate 80.

Figure 14B:
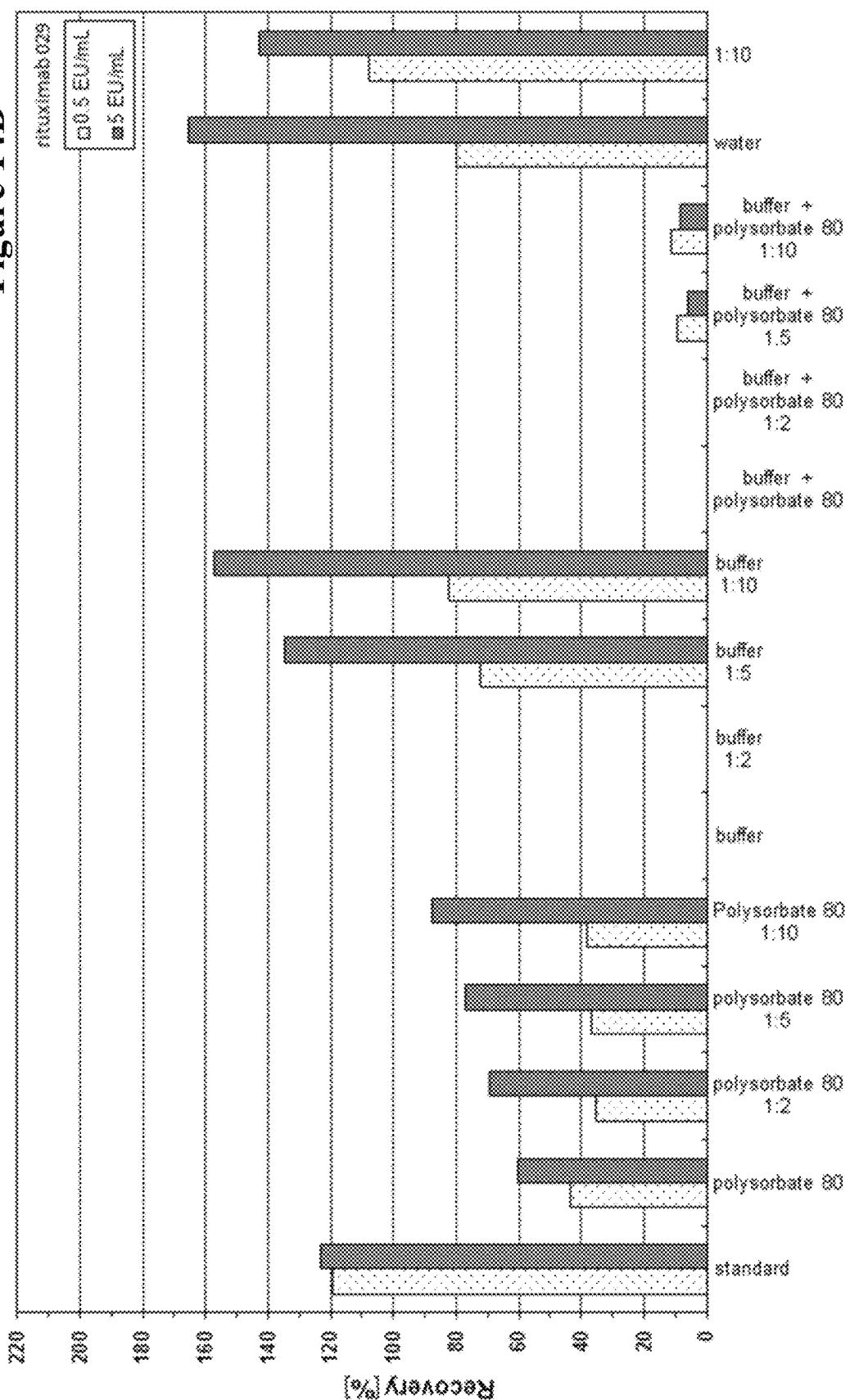

These results have been verified by another experiment wherein several different dilutions were tested. In particular, samples comprising either 25 mM sodium citrate buffer (pH 6.5), 700 mg/L polysorbate 80 or both (i.e. the formulation of rituximab) were prepared. These preparations as well as water controls were spiked with Lonza CSE to a final concentration of 0.5 or 5.0 EU/ml. All samples were shaken for 1 hour at room temperature in the vortex machine [shaker: Heidolph Multi Reax, high speed (2,037 rpm) in a 1.5 clear glass, crimp neck, flat bottom vessel Subsequently, the dilutions as indicated in FIG. 14(B) (i.e. [rituximab 029]) were performed with endotoxin-free water in 1.5 ml vials and are shaken (as before) for 1 min. After shaking, the LAL assay was performed. In particular, 100 μl of each of the samples were added to a 96-well plate and incubated in the reader for 10 min at 37° C. Then, 100 μl chromogen added to each of the samples and the measurement was carried out. As can be seen in FIG. 14(B) (i.e. [rituximab 029]) the LER effect of the buffer (i.e. the sodium citrate buffer) is stronger as compared to the LER effect of the detergent (i.e. polysorbate 80). While polysorbate 80 shows a relatively constant recovery rate (~40-90%, see FIG. 14(B), [rituximab 029], columns 2-5 from the right), in citrate-buffer the LER effect is dependent on the dilution. Most importantly, a strong and reproducible LER effect is expressed if polysorbate 80 is combined with citrate buffer (as it is the case in monoclonal antibody formulations), see FIG. 14(B) (i.e. [rituximab 029]).

In these samples, also with high dilution, the recovery rate is only 5-10%. Accordingly, this experiment demonstrates how a positive LER effect can be obtained. This result is pioneering in the field of endotoxin determination, as it allows for testing of several means and methods for their ability to overcome the LER effect.

When analyzing the effect of buffer and detergent separately, the effect of the buffer on the LER effect was more pronounced in both NeoRecormon® and Rituximab (see, e.g. FIG. 14(B), i.e. [rituximab 029]). These data surprisingly indicate that the removal of the buffer is more critical than removal of the detergent. Taking into account that the concentrations of buffers in both formulations is comparable (rituximab: 25 mM sodium citrate and NeoRecormon: 27.8 mM for sodium phosphate), the reason for this effect has to be found in the structure of the buffer and/or its physicochemical properties. Sodium citrate is a well-known chelating anion, whereas in phosphate this effect is less pronounced. Therefore, these observations may also explain why the addition of $Mg^{2+}$ is important for overcoming the LER effect, since $Mg^{2+}$ is complexed by the chelating buffer reducing its concentration in the LAL test.

Reference Example 11: Standard Physical and Biochemical Methods do not Recover Endotoxins Masked by the LER Effect In order to overcome the LER effect (in the buffers identified as having the LER effect in Reference Example 9), different physical and biochemical methods were tested:

Freezing of endotoxin spiked samples at −30° C. This study is based on the initial finding that LER is more pronounced at room temperature as compared to 2-8° C. Result: freezing of endotoxin spiked samples does not overcome LER.

Heating of endotoxin spiked samples for 30 minutes at 70° C. This study was conducted because heating has shown to overcome endotoxin masking effects for some products (Dawson, 2005, LAL update. 22:1-6). Result: Heat treatment of endotoxin spiked samples does not overcome LER.

Dilution of endotoxin spiked samples to maximum valid dilution (MVD). This study was conducted since sample dilution is the standard method to overcome LAL inhibition. Result: As can be seen from FIG. 11 (i.e. [rituximab 002], [rituximab 004], [rituximab 005]), dilution alone does not overcome the LER effect.

Use of Endo Trap Columns for endotoxin spiked samples. These columns serve to remove endotoxins from solutions via affinity chromatography. A test was carried out with an aqueous endotoxin solution. Result: Endotoxins could not be recovered from the column.

Reference Example 12: Removal of Detergents by Dialysis

Several dialysis chambers and membranes (including different sizes of the molecular weight cut-off, MWCO) available on the market have been tested as detailed below.

Suitable membranes for dialysis chambers are commercially available are, e.g., cellulose acetate (MWCO 100 to 300,000 Da), regenerated cellulose (MWCO 1,000 to 50,000 Da), or cellulose ester (MWCO of 100 to 500 Da). Herein cellulose acetate and cellulose ester are preferred, cellulose acetate is most preferred.

The test samples (i.e. rituximab) were diluted prior to the dialysis, this way approaching the CMC and creating increasing levels of monomers of the detergent which were expected to diffuse through the dialysis membrane. Investigations on the recovery rate of the CSE spiked revealed that in case of rituximab the regenerated cellulose was not so efficient as compared to the cellulose acetate. In a series of experiments with rituximab it was identified that the MWCO is preferably ~10 kDa. This size is preferred because this size is thought to i) speed up the dialysis process and ii) allow also higher oligomeric aggregates (but not micelles) of the detergent to pass through the membrane, in case the hydrophobic character of the cellulose acetate (acetyl esters on the glucose polymers) will not inhibit such kind of transportation process.

The experiment to determine the optimum for dialysis has been performed to mimic the situation in NeoRecormon®. As outlined earlier, buffer and detergent were those compounds in the sample formulation which mostly influenced the LER effect. In order to mimic the formulation of NeoRecormon® a defined amount of phosphate buffer in a total volume of 0.5 ml (2.7 mg) in the presence of 0.1 mg/ml poysorbate 20 was prepared and subjected to dialysis (in a spin dialyzer). In FIG. 1 is shown a very simple example of such experiment using a dialysis membrane of cellulose acetate with a MWCO of 12-16 kDa. Here the material remaining in the inner dialysate after a given time is shown, this way demonstrating the efficiency of the dialysis. In particular, the weight of material remaining in the inner dialysis chamber over a period of 72 h (3d) was analyzed. The result is rather surprising as it shows that complete and effective dialysis of NeoRecormon® is only achieved after a longer dialysis period at room temperature (>24-48 h). Based on this experiment the preferred dialysis time is 20 h to overnight (e.g. 24 h). In addition, this result indicates that Harvard Fast Dialyzer is preferred over the Harvard Spin Dialyzer, the former having the double area of dialysis membrane, and thus leads to a quicker dialysis.

Figure 2:
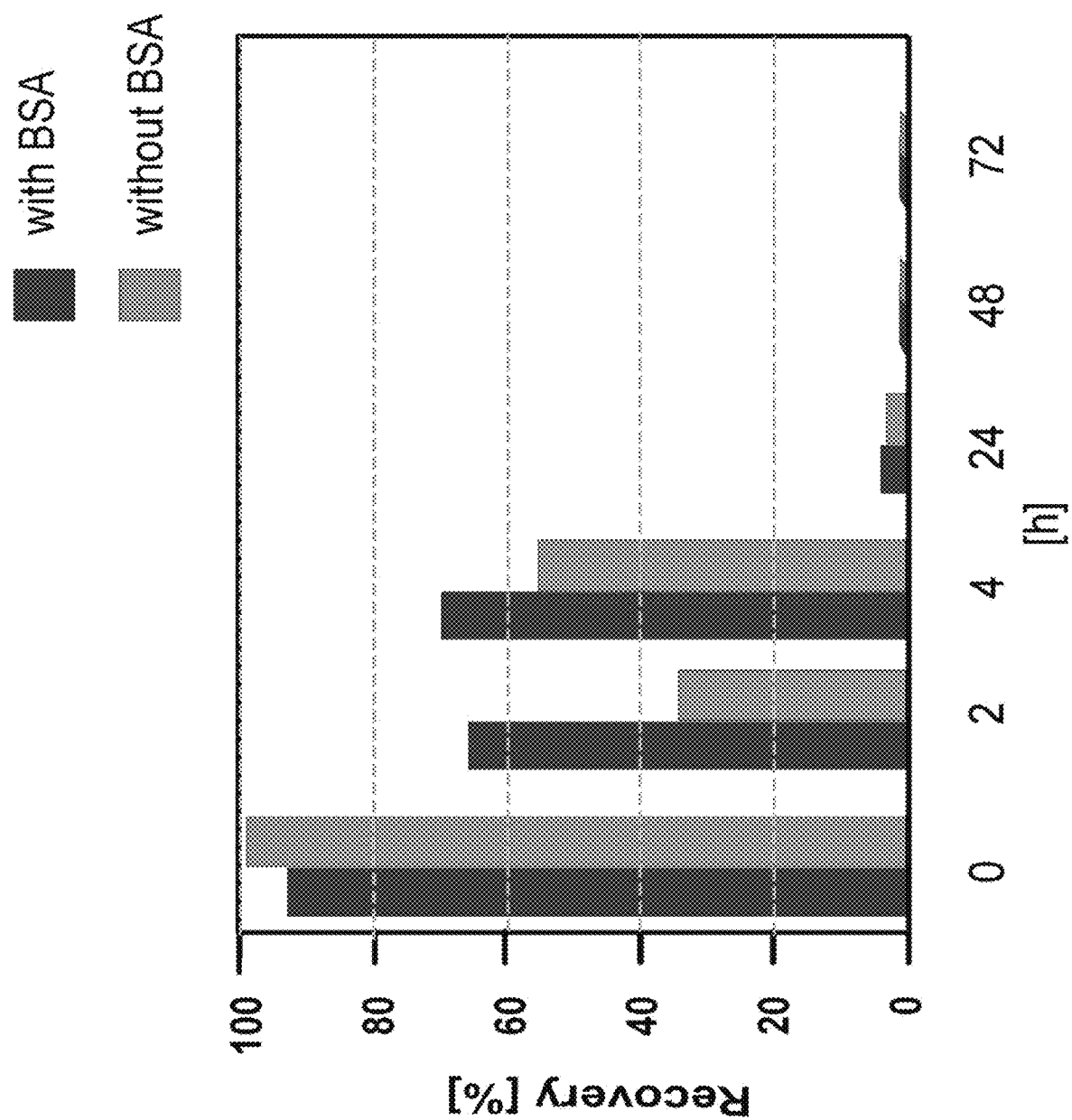
FIG. 2 Dialysis of NeoRecormon® containing phosphate and polysorbate 20 by using a membrane MWCO of 12-16 kDa treated with or without (w/o) bovine serum albumin (BSA) prior to dialysis. Shown is the content of phosphate (P) in the inner dialyzate obtained after the time indicated. Left bars show the amount of P when the membrane was treated with 0.2% BSA before dialysis. Right bars correspond to the amount of P without BSA-treatment. The photometric test of the phosphate recovered from the inner dialyzate was performed according to Strominger (1959, J. Biol. Chem. 234: 3263-3267).

In FIG. 2, there is shown the efficiency of dialysis in case phosphate is placed into the inner dialysate compartment of the dialysis. In this experiment, the dialysis membrane (MWCO 12-16 kDa) was washed with 0.2% BSA (30 min) prior to its use, in order to avoid unspecific absorbance of the CSE spiked to the sample. However, in the herein provided inventive methods a dilution (e.g. a dilution at a ratio of 1:10) of the samples reduces the concentration of the detergent.

Reference Example 13: Influence of $MgCl_2$ on the LER Effect

It has been found that the LER effect could be reduced by addition of $MgCl_2$ to the sample (see, e.g., FIG. 15 (i.e. [rituximab 031]). In particular, best results were observed when the concentration of $Mg^{2+}$ was twice the concentration of the sodium citrate (i.e. 50 mM $Mg^{2+}$).

Figure 15A:
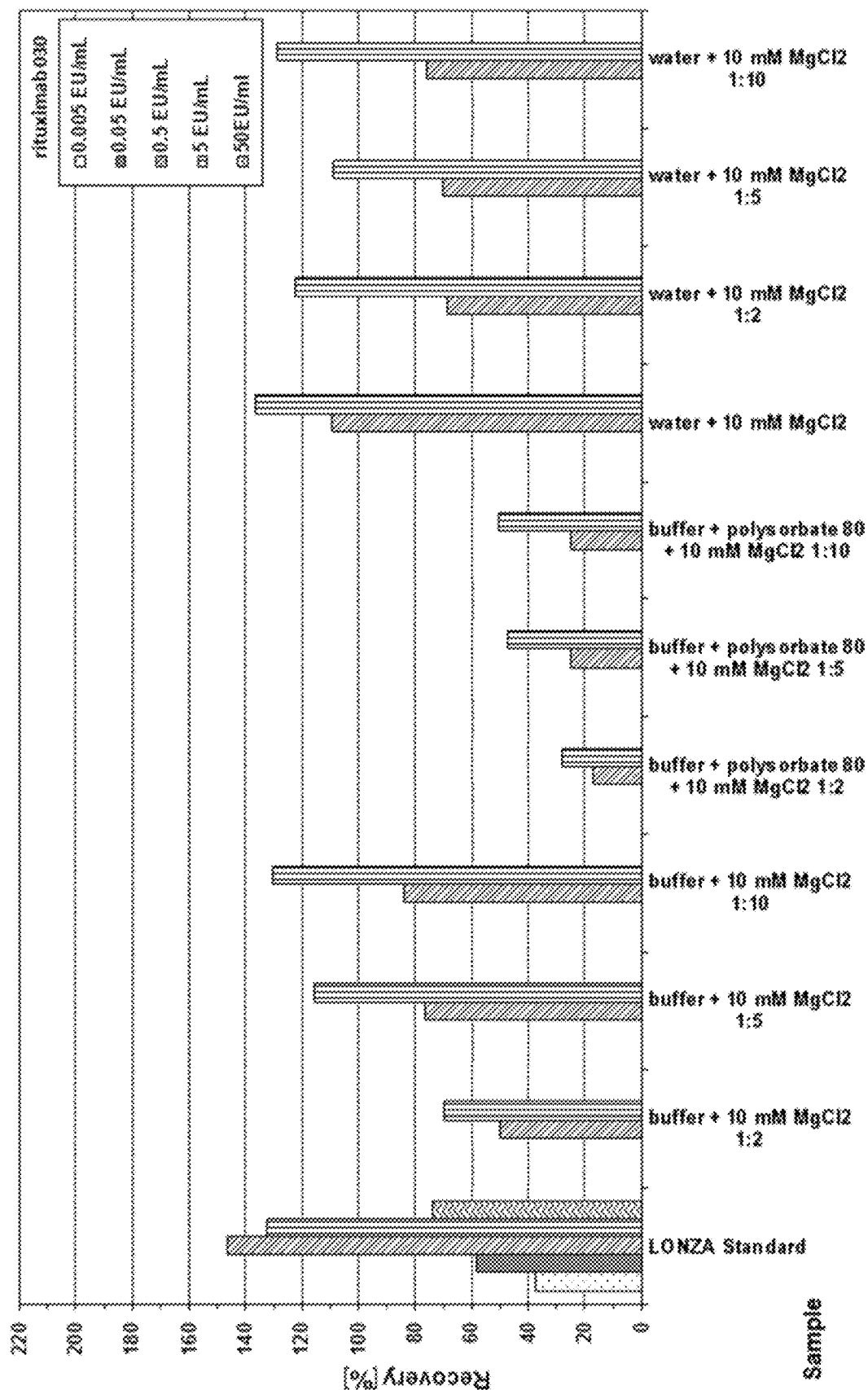
FIG. 15: Effect of $MgCl_2$ on the LER effect. Recovery rates (%) obtained by performing the LAL assay as described in Reference Example 13 are shown. (A) Addition of $MgCl_2$ to a concentration of 10 mM [rituximab 030]; (B) Addition of $MgCl_2$ to a concentration of 50 mM [rituximab 031]; (C) Addition of $MgCl_2$ to a concentration of 25 mM [rituximab 032]; (D) Addition of $MgCl_2$ to a concentration of 75 mM [rituximab 033].
Figure 15C:
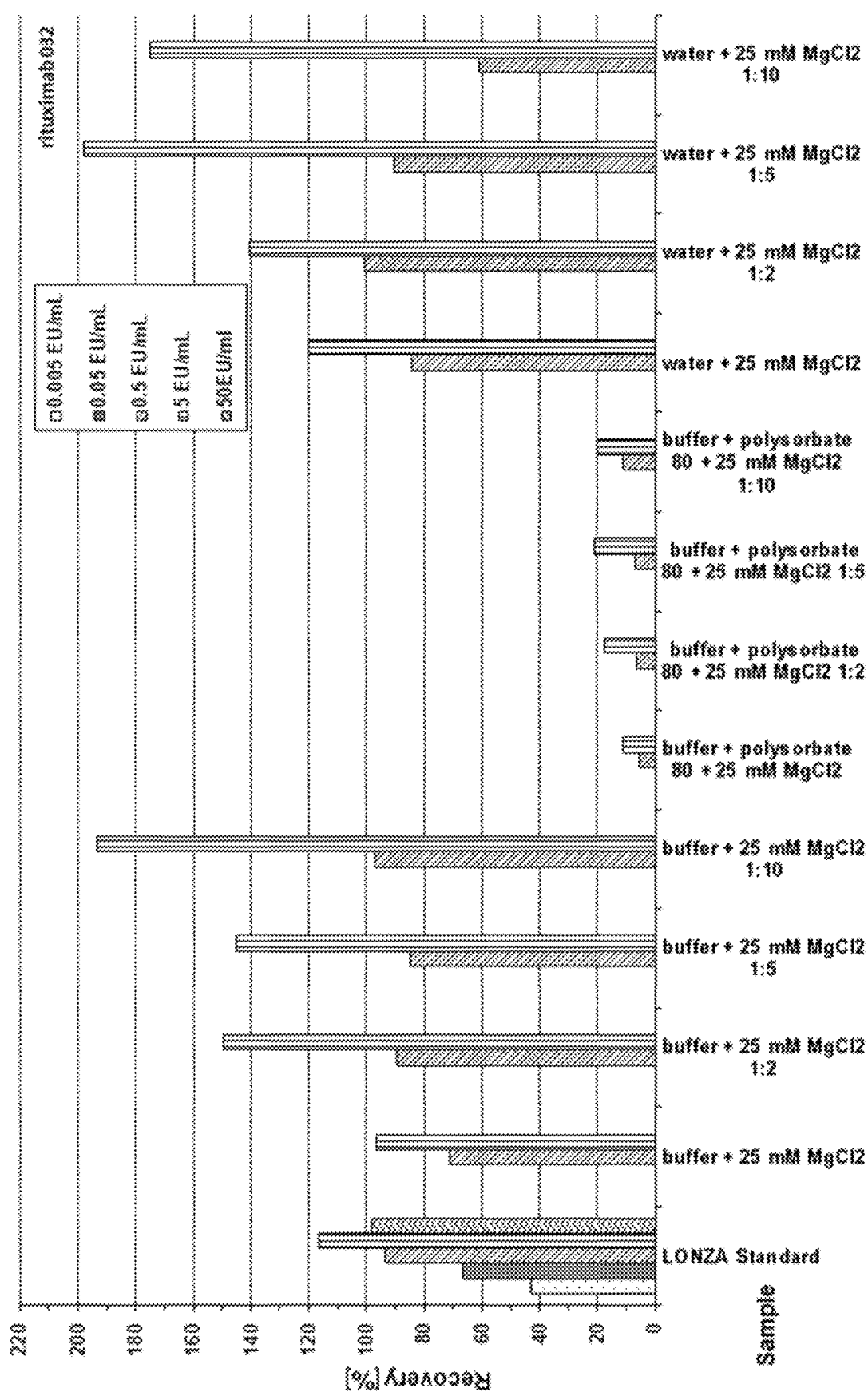

In particular, samples comprising either 25 mM sodium citrate buffer, pH 6.5 (i.e. sodium citrate buffer, pH 6.5), 0.7 mg/ml polysorbate 80, or both (with pH 6.5, i.e. the formulation of rituximab) were prepared. These preparations as well as water controls were spiked with Lonza CSE to a final concentration of 0.5 or 5.0 EU/ml. All samples were shaken for 1 hour at room temperature [shaker: Heidolph Multi Reax, high speed (2,037 rpm) in a 1.5 clear glass, crimp neck, flat bottom vessel]. Then, $MgCl_2$ to reach a concentration of 10 mM, 25 mM, 50 mM or 75 mM was added to the samples. Subsequently, the dilutions as indicated in FIGS. 15(A), 18(B), 18(C), and 18(D) (i.e. [rituximab 030-rituximab 033]) were performed with endotoxin-free water in a 1.5 ml vial and shaken (i.e. vortexed as before) for 1 min. After shaking, the LAL assay was performed. In particular, 100 µl of each of the samples was added in a 96-well plate and incubated in the reader for 10 min at 37° C. Afterwards, 100 µl chromogen was added to each of the samples and the measurement was carried out. As can be seen in FIG. 15(A) (i.e. [rituximab 030]), in all diluted samples, $MgCl_2$ (10 mM) can neutralize the complexing effect of citrate. Magnesium ions reduce the LER effect in samples which comprise polysorbate 80 as well as citrate buffer. In this case, a recovery of approximately 50% with 5.0 EU/ml and 25% with 0.5 EU/ml was achieved. The control values of water range around the theoretically expected value (i.e. 70-130%). Moreover, a comparison of FIGS. 15(A), 15(B), 15(C), and 15(D) (i.e. [rituximab 030], [rituximab 031], [rituximab 032] and [rituximab 033]) shows that a $MgCl_2$ concentration which is twice the concentration of the citrate buffer (i.e. 50 mM $MgCl_2$) leads to best recovery rates. Although 25 mM and 75 mM $MgCl_2$ are not the optimal concentration of $MgCl_2$, these concentrations nevertheless overcome the LER of the citrate buffer (recovery: 75-190%). In a similar experiment wherein rituximab was used as a sample, it was demonstrated that only the addition of $MgCl_2$ to a concentration of 10 mM, 50 mM, or 75 mM $MgCl_2$ and a subsequent dilution at a ratio of 1:10 (without dialysis) was able to lead to a satisfactory recovery of endotoxin which was spiked to a final concentration of 5.0 EU/ml (see FIG. 5, i.e. [rituximab 059]).

Reference Example 14: Effects of Mechanical Treatments on the LER Effect

It was tested whether mechanical treatments (such as shaking and ultrasonification) are useful for dispersing the micelles, and thus for reducing the LER effect.

Figure 3B:
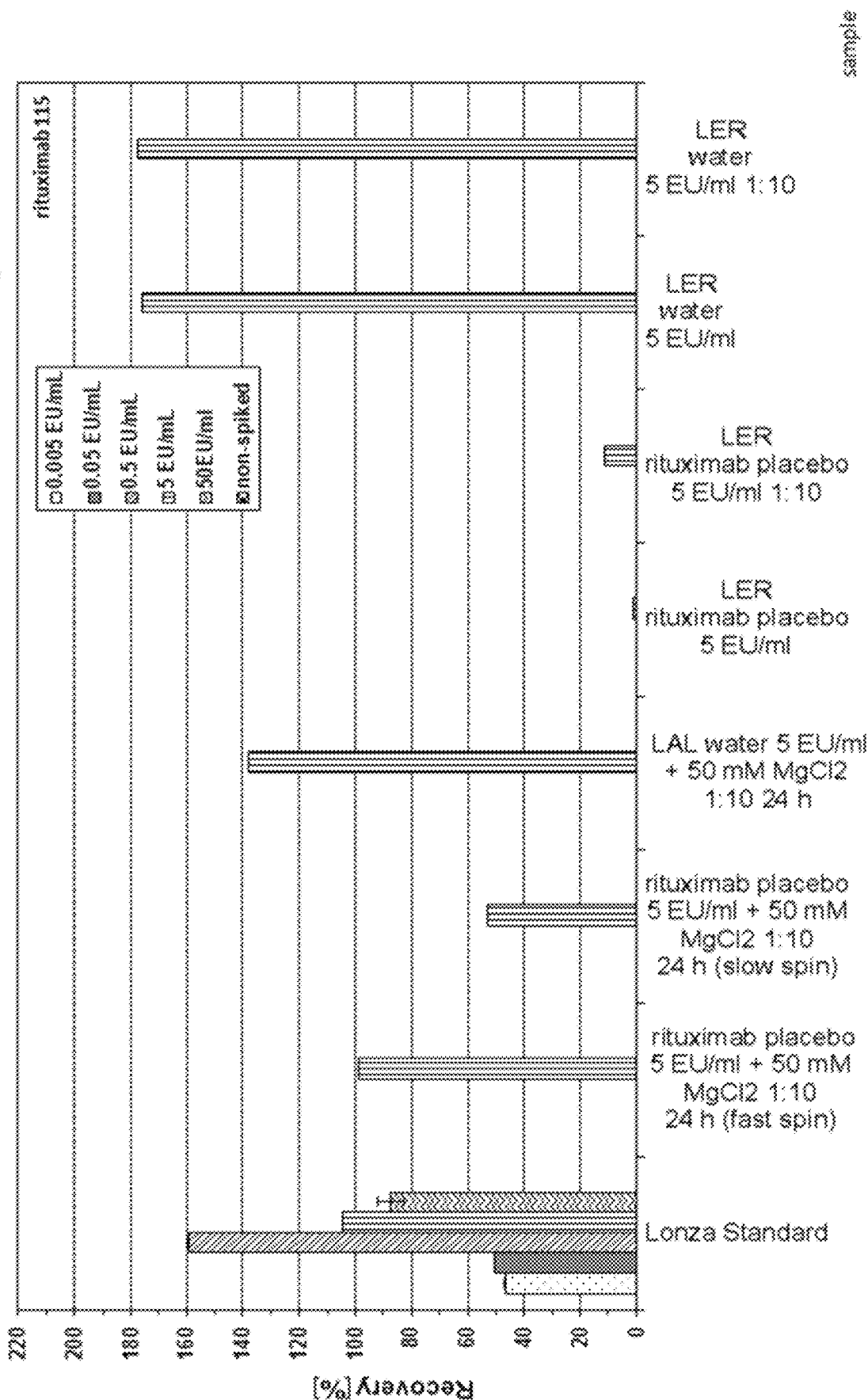
Figure 16:
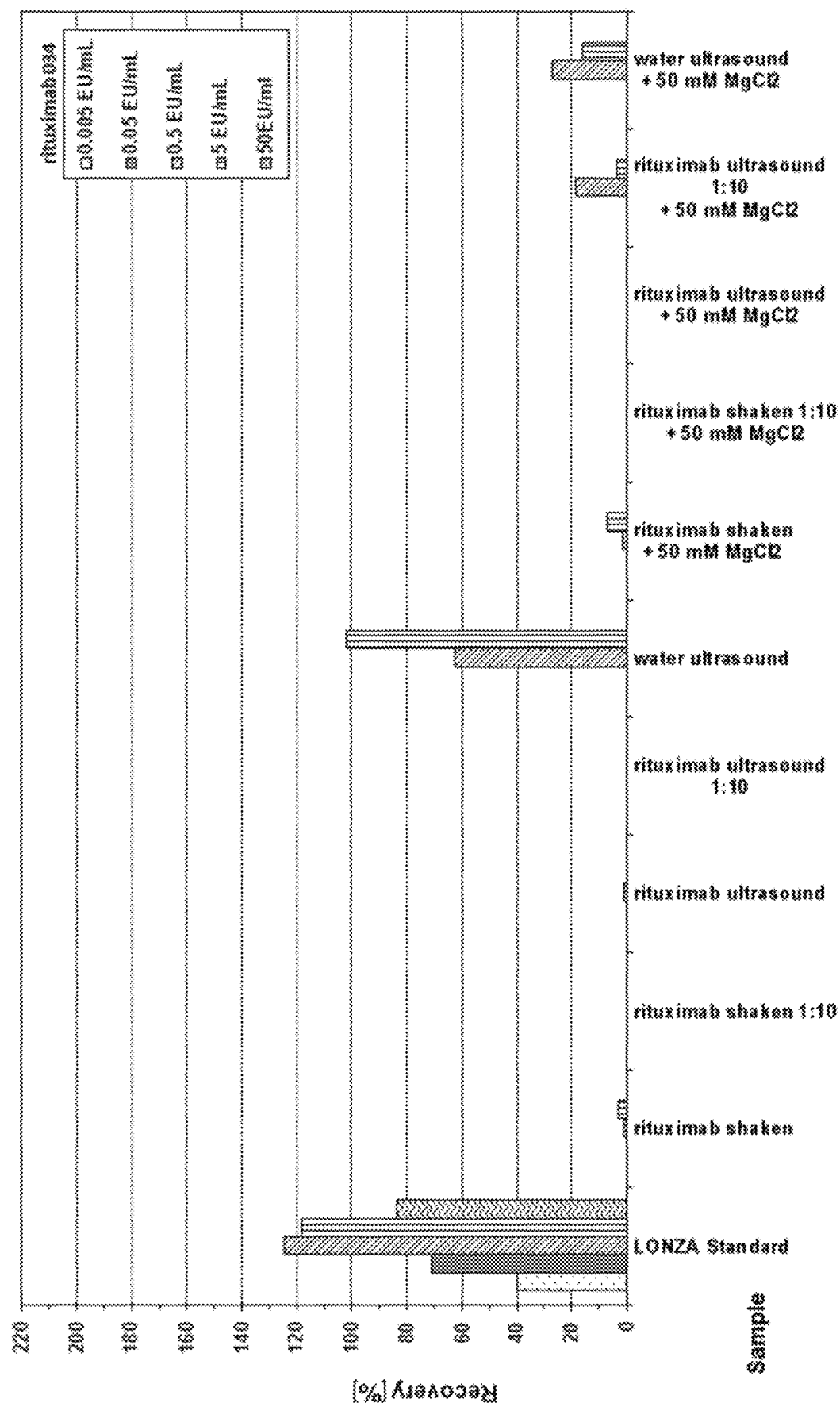
FIG. 16: Effect of mechanical treatments on the LER effect. Recovery rates (%) obtained by performing the LAL assay as described in Reference Example 14 are shown [rituximab 034]. In the Figure, "shaken" means shaken for 60 min.

In particular, endotoxin-free water (i.e. LAL water) and rituximab were spiked with Lonza CSE to achieve a final concentration of 0.5 and 5.0 EU/ml. Then, the samples were either sonicated for 1 hour or shaked for 1 hour [i.e. vortexed in the Heidolph Multi Reax shaker at high speed (2,037 rpm) at room temperature in a 1.5 ml clear glass, crimp neck, flat bottom vessels]. Then 1:10 (sample:water) dilutions were prepared with endotoxin-free water. Subsequently, the diluted samples were dialyzed by using a 12-16 kD membrane (which, before dialysis, had been incubated in 0.2% BSA for 30 min). The dialysis took place in two 2 l beakers for 4 hours. The external dialysate was 1 l Aqua Braun and the water was changed after 2 hours of dialysis. After dialysis $MgCl_2$ was added to some of the samples (as indicated in FIG. 16, i.e. [rituximab 034]) so as to result in a final concentration of $MgCl_2$ of 50 mM. After addition of $MgCl_2$, all samples (also the samples without $MgCl_2$) were shaken for 20 min (e.g. vortexed as before). Subsequently, the LAL assay was performed. In particular, 100 µl of each of the samples was added to a 96-well plate and incubated in the reader for 10 min at 37° C. Then, 100 µl chromogen was added to each of the samples and the measurement was carried out. As can be seen in FIG. 16 (i.e. [rituximab 034], the recovery rates are neither improved by shaking nor by ultrasound. Therefore, it can be concluded that mechanically dispersing the LER causing micelles by shaking or ultrasonification is compared thereto inefficient. However, addition $MgCl_2$ (50 mM) reduced the LER effect as it resulted in improved recovery values of up to 5-20%. In addition, this experiment also demonstrates that the order of the different performed steps is important for overcoming the LER effect. In particular, in the experiment described above (and shown in FIG. 16, i.e. [rituximab 034]), the order of the steps was (a) dilution, (b) dialysis, and (c) addition of $MgCl_2$. This order did not result in satisfactory recovery rates (see FIG. 16, i.e. [rituximab 034]). However, as demonstrated in FIGS. 3 and 4 (i.e. [rituximab 046], [rituximab 115] and [rituximab 117]), the order (a) addition of $MgCl_2$, (b) dilution, and (c) dialysis results in recovery rates which fulfill the requirements of the FDA (i.e. 50%-200%).

The present invention refers to the following nucleotide and amino acid sequences:

SEQ ID NO: 1: Rituximab heavy chain,
amino acid sequence
QVQLQQPGAELVKPGASVKMSCKASGYTFTSYNMHWVKQTPGRGLEWIGA

IYPGNGDTSYNQKFKGKATLTADKSSSTAYMQLSSLTSEDSAVYYCARST

YYGGDWYFNVWGAGTTVTVSAASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

K

SEQ ID NO: 2: Rituximab light chain,
amino acid sequence
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

The invention claimed is:

1. A method for preparation of a sample, wherein the sample comprises an antibody, for a *limulus* amoebocyte lysate (LAL) assay, wherein the method comprises the following steps in the following order:
   (a) adding magnesium ions,
   (b) diluting the sample, and
   (c) dialyzing the sample having a pH-value of 5.7-8.0 against an endotoxin-free aqueous solution,
wherein the antibody is a monoclonal therapeutic antibody.

2. A method for determining bacterial endotoxin in a sample comprising an antibody exhibiting the LER effect, wherein the method comprises the following steps in the following order:
   (a) adding magnesium ions to the sample,
   (b) diluting the sample,
   (c) dialyzing the sample having a pH-value of 5.7-8.0 against an endotoxin-free aqueous solution, and
   (d) determining bacterial endotoxin in the sample by using a LAL assay.

3. The method of claim 1, wherein the antibody is formulated with polysorbate 80.

4. The method of claim 1, wherein the antibody is formulated with a citrate buffer.

5. The method of claim 1, wherein the antibody is formulated with 25 mM sodium citrate buffer and 700 mg/l polysorbate 80 and has a pH value of 6.5.

6. The method of claim 1, wherein the antibody is the anti-CD20 antibody rituximab.

7. The method of claim 1, wherein in step (a) magnesium ions are added to a final concentration of 2.5 to 75 mM.

8. The method of claim 1, wherein in step (b) the pH-value of the sample is adjusted by diluting the sample with 10-50 mM Tris/HCl buffer pH 6.0-9.0.

9. The method of claim 1, wherein in step (b) the sample is diluted at a ratio of 1:10.

10. The method of claim 1, wherein during dialysis in step (c) the sample has a pH-value of 6.0-8.0.

11. The method of claim 1, wherein in step (c) the dialysis takes 24 hours at room temperature.

12. The method of claim 1, wherein for the dialysis in step (c) a membrane with a molecular-weight cut-off of 10 kDa is used.

13. The method of claim 1, wherein for the dialysis in step (c) a cellulose acetate membrane is used.

14. The method of claim 1, wherein for the dialysis in step (c) the aqueous solution is changed twice.

15. The method of claim 1, further comprising the step of producing a low endotoxin recovery (LER) positive control by spiking a known amount of endotoxin into an aliquot of the sample and shaking the endotoxin spiked aliquot of the sample for 60 min to 2 hours.

16. A method for rendering a sample comprising an antibody reactive to factor C in a LAL enzymatic cascade, comprising the steps of:

(a) adding magnesium ions to the sample,
(b) diluting the sample, and
(c) dialyzing the sample having a pH-value of 5.7-8.0 against an endotoxin-free aqueous solution, wherein the antibody is a monoclonal therapeutic antibody.

17. The method of claim 2, wherein the antibody is a therapeutic antibody.

18. The method of claim 2, wherein the antibody is formulated with polysorbate 80.

19. The method of claim 2, wherein the antibody is formulated with a citrate buffer.

20. The method of claim 2, wherein the antibody is formulated with 25 mM sodium citrate buffer and 700 mg/l polysorbate 80 and has a pH value of 6.5.

21. The method of claim 2, wherein the antibody is the anti-CD20 antibody rituximab.

22. The method of claim 2, wherein in step (a) magnesium ions are added to a final concentration of 25 to 75 mM.

23. The method of claim 2, wherein in step (b) the pH-value of the sample is adjusted by diluting the sample with 10-50 mM Tris/HCl buffer pH 6.0-9.0.

24. The method of claim 2, wherein in step (b) the sample is diluted at a ratio of 1:10.

25. The method of claim 2, wherein during dialysis in step (c) the sample has a pH-value of 6.0-8.0.

26. The method of claim 2, wherein in step (c) the dialysis takes 24 hours at room temperature.

27. The method of claim 2, wherein for the dialysis in step (c) a membrane with a molecular-weight cut-off of 10 kDa is used.

28. The method of claim 2, wherein for the dialysis in step (c) a cellulose acetate membrane is used.

29. The method of claim 2, wherein for the dialysis in step (c) the aqueous solution is changed twice.

30. A method for rendering a sample comprising an antibody reactive to factor C in a LAL enzymatic cascade, comprising the steps of:
(a) adding magnesium ions to the sample,
(b) diluting the sample,
(c) dialyzing the sample having a pH-value of 5.7-8.0 against an endotoxin-free aqueous solution, and
(d) determining bacterial endotoxin in the sample by using a LAL assay, wherein the antibody is a monoclonal therapeutic antibody.

31. The method according to claim 1, wherein said magnesium ions are $MgCl_2$.

32. The method according to claim 2, wherein said magnesium ions are $MgCl_2$.

33. The method according to claim 8, the pH-value of the sample is adjusted by diluting the sample with 10-50 mM Tris/HCl buffer 6.0-8.0.

34. The method according to claim 16, wherein said magnesium ions are $MgCl_2$.

35. The method according to claim 23, wherein the pH-value of the sample is adjusted by diluting the sample with 10-50 mM Tris/HCl buffer pH 6.0-8.0.

36. The method according to claim 30, wherein said magnesium ions are $MgCl_2$.

37. A method for preparation of a sample, Wherein the sample comprises an antibody, for a *limulus* amoebocyte lysate (LAL) assay, wherein the method comprises the following steps in the following order:
(a) adding magnesium ions,
(b) diluting the sample,
(c) dialyzing the sample having a pH-value of 5.7-8.0 against an endotoxin-free aqueous solution, and
(d) determining bacterial endotoxin in the sample by using a LAL assay, wherein the antibody is a therapeutic antibody.

38. The method of claim 37, wherein the antibody is formulated with polysorbate 80.

39. The method of claim 37, wherein the antibody is formulated with a citrate buffer.

40. The method of claim 37, wherein the antibody is formulated with 25 mM sodium citrate buffer and 700 mg/l polysorbate 80 and has a pH value of 6.5.

41. The method of claim 37, wherein the antibody is the anti-CD20 antibody rituximab.

42. The method of claim 37, wherein in step (a) magnesium ions are added to a final concentration of 25 to 75 mM.

43. The method of claim 37, wherein in step (b) the pH-value of the sample is adjusted by diluting the sample with 10-50 mM Tris/HCl buffer pH 6.0-9.0.

44. The method of claim 37, wherein in step (b) the sample is diluted at a ratio of 1:10.

45. The method of claim 37, wherein during dialysis in step (c) the sample has a pH-value of 6.0-8.0.

46. The method of claim 37, wherein in step (c) the dialysis takes 24 hours at room temperature.

47. The method of claim 37, wherein for the dialysis in step (c) a membrane with a molecular-weight cut-off of 10 kDa is used.

48. The method of claim 37, wherein for the dialysis in step (c) a cellulose acetate membrane is used.

49. The method of claim 37, wherein for the dialysis in step (c) the aqueous solution is changed twice.

50. The method of claim 37, further comprising the step of producing a low endotoxin recovery (LER) positive control by spiking a known amount of endotoxin into an aliquot of the sample and shaking the endotoxin spiked aliquot of the sample for 60 min to 2 hours.

51. The method according to claim 37, wherein said magnesium ions are $MgCl_2$.

52. The method according to claim 43, the pH-value of the sample is adjusted by diluting the sample with 10-50 mM Tris/HCl buffer 6.0-8.0.

* * * * *

SEQUENCE LISTING

<160> NUMBER OF SEQ ID NOS: 2

<210> SEQ ID NO 1
<211> LENGTH: 451
<212> TYPE: PRT
<213> ORGANISM: Artificial Sequence
<220> FEATURE:
<223> OTHER INFORMATION: Rituximab heavy chain

<400> SEQUENCE: 1

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

```
Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 2
<211> LENGTH: 213
<212> TYPE: PRT
<213> ORGANISM: Artificial Sequence
<220> FEATURE:
<223> OTHER INFORMATION: Rituximab Light Chain
```

```
<400> SEQUENCE: 2

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
210
```